(12) United States Patent
Wortz et al.

(10) Patent No.: US 11,364,107 B2
(45) Date of Patent: Jun. 21, 2022

(54) PROSTHETIC CAPSULAR DEVICES, SYSTEMS, AND METHODS

(71) Applicant: Omega Ophthalmics LLC, Versailles, KY (US)

(72) Inventors: Gary N. Wortz, Nicholasville, KY (US); Rick William Ifland, Versailles, KY (US)

(73) Assignee: Omega Ophthalmics LLC, Versailles, KY (US)

( * ) Notice: Subject to any disclaimer, the term of this patent is extended or adjusted under 35 U.S.C. 154(b) by 0 days.

(21) Appl. No.: 17/499,692

(22) Filed: Oct. 12, 2021

(65) Prior Publication Data

US 2022/0110739 A1    Apr. 14, 2022

Related U.S. Application Data

(60) Provisional application No. 63/149,153, filed on Feb. 12, 2021, provisional application No. 63/091,183, (Continued)

(51) Int. Cl.
*A61F 2/16* (2006.01)
*A61F 2/00* (2006.01)

(52) U.S. Cl.
CPC .............. *A61F 2/16* (2013.01); *A61F 2/0077* (2013.01); *A61F 2002/0081* (2013.01); (Continued)

(58) Field of Classification Search
CPC ....................... A61F 2/16; A61F 2/0077; A61F 2002/16901; A61F 2002/0081; A61F 2230/0006; A61F 2240/001
See application file for complete search history.

(56) References Cited

U.S. PATENT DOCUMENTS

| 4,073,014 A | 2/1978 | Poler |
| 4,373,218 A | 2/1983 | Schachar |

(Continued)

FOREIGN PATENT DOCUMENTS

| DE | 202013009162 | 2/2014 |
| EP | 0 337 390 | 2/1993 |

(Continued)

OTHER PUBLICATIONS

Allergan, "Postive Phase I/II Interim Data of Bimatoprost Sustained-Release Implant for IOP Therapy in Glaucoma", Nov. 16, 2015, http://www.allergan.com/NEWS/News/Thomson-Reuters/Positive-Phase-I-II-Interim-Data-of-Bimatoprost-Su in 4 pages.

(Continued)

*Primary Examiner* — Jennifer Dieterle
*Assistant Examiner* — Tiffany P Shipmon
(74) *Attorney, Agent, or Firm* — Knobbe, Martens, Olson & Bear, LLP

(57) ABSTRACT

A prosthetic capsular device configured to be inserted in an eye after removal of a lens, in some embodiments, can comprise a housing structure comprising capable of containing an intraocular device. The housing structure can comprise an anterior portion comprising an anterior opening, a posterior portion comprising a posterior opening, and a continuous lateral portion between the anterior portion and the posterior portion.

20 Claims, 41 Drawing Sheets

Related U.S. Application Data filed on Oct. 13, 2020, provisional application No. 63/090,426, filed on Oct. 12, 2020.

(52) U.S. Cl.
CPC ............... *A61F 2002/16901* (2015.04); *A61F 2230/0006* (2013.01); *A61F 2240/001* (2013.01)

(56) References Cited

U.S. PATENT DOCUMENTS

| | | |
|---|---|---|
| 4,402,579 A | 10/1983 | Poler |
| 4,423,856 A | 1/1984 | Takahashi et al. |
| 4,435,856 A | 3/1984 | L'Esperance |
| 4,575,373 A | 3/1986 | Johnson |
| 4,585,456 A | 4/1986 | Blackmore |
| 4,629,461 A | 12/1986 | Clayman et al. |
| 4,685,921 A | 8/1987 | Peyman |
| 4,704,124 A | 11/1987 | Shearing |
| 4,731,078 A | 3/1988 | Stoy et al. |
| 4,816,031 A | 3/1989 | Pfoff |
| 4,833,890 A | 5/1989 | Kelman |
| 4,842,601 A | 6/1989 | Smith |
| 4,888,012 A | 12/1989 | Horn et al. |
| 4,888,016 A | 12/1989 | Langerman |
| 4,892,543 A | 1/1990 | Turley |
| 4,932,966 A | 6/1990 | Christie et al. |
| 5,147,395 A | 9/1992 | Willis |
| 5,171,266 A | 12/1992 | Wiley et al. |
| 5,180,390 A | 1/1993 | Drews |
| 5,203,788 A | 4/1993 | Wiley |
| 5,222,981 A | 6/1993 | Werblin |
| 5,275,623 A | 1/1994 | Sarfarazi |
| 5,326,347 A | 7/1994 | Cumming |
| 5,358,520 A | 10/1994 | Patel |
| 5,522,891 A | 6/1996 | Klaas |
| 5,562,731 A | 10/1996 | Cumming |
| 5,628,795 A | 5/1997 | Langerman |
| 5,628,798 A | 5/1997 | Eggleston et al. |
| 5,653,751 A | 8/1997 | Samiy et al. |
| 5,674,282 A | 10/1997 | Cumming |
| 5,676,669 A | 10/1997 | Colvard |
| 5,697,973 A | 12/1997 | Peyman et al. |
| 5,702,402 A | 12/1997 | Brady |
| 5,800,533 A | 9/1998 | Eggleston et al. |
| 5,964,802 A | 10/1999 | Anello et al. |
| 5,968,094 A | 10/1999 | Werblin et al. |
| 5,984,962 A | 11/1999 | Anello et al. |
| 6,015,435 A | 1/2000 | Valunin |
| 6,027,531 A | 2/2000 | Tassignon |
| 6,113,633 A | 9/2000 | Portney |
| 6,117,171 A | 9/2000 | Skottun |
| 6,136,026 A | 10/2000 | Israel |
| 6,143,244 A | 11/2000 | Xia et al. |
| 6,217,612 B1 | 4/2001 | Woods |
| 6,235,055 B1 | 5/2001 | Chu |
| 6,280,471 B1 | 8/2001 | Peyman et al. |
| 6,299,641 B1 | 10/2001 | Woods |
| 6,322,589 B1 | 11/2001 | Cumming |
| 6,413,276 B1 | 7/2002 | Werblin |
| 6,428,574 B1 | 8/2002 | Valunin |
| 6,443,985 B1 | 9/2002 | Woods |
| 6,450,642 B1 | 9/2002 | Jethmalani et al. |
| 6,454,801 B1 | 9/2002 | Portney |
| 6,464,725 B2 | 10/2002 | Skotton |
| 6,488,708 B2 | 12/2002 | Sarfarazi |
| 6,503,276 B2 | 1/2003 | Lang et al. |
| 6,506,212 B2 | 1/2003 | Zhou et al. |
| 6,524,340 B2 | 2/2003 | Israel |
| 6,533,813 B1 | 3/2003 | Lin et al. |
| 6,537,281 B1 | 3/2003 | Portney |
| 6,537,317 B1 | 3/2003 | Steinert |
| 6,576,012 B2 | 6/2003 | Lang |
| 6,596,026 B1 | 7/2003 | Gross |
| 6,645,246 B1 | 11/2003 | Weinschenk |
| 6,695,881 B2 | 2/2004 | Peng et al. |
| 6,721,043 B2 | 4/2004 | Platt et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,786,934 B2 | 9/2004 | Zadno-Azizi et al. |
| 6,797,004 B1 | 9/2004 | Brady et al. |
| 6,813,097 B2 | 11/2004 | Jethmalani et al. |
| 6,818,158 B2 | 11/2004 | Pham et al. |
| 6,824,266 B2 | 11/2004 | Jethmalani et al. |
| 6,827,738 B2 | 12/2004 | Willis et al. |
| 6,846,326 B2 | 1/2005 | Zadno-Azizi et al. |
| 6,851,804 B2 | 2/2005 | Jethmalani et al. |
| 6,858,040 B2 | 2/2005 | Nguyen et al. |
| 6,881,225 B2 | 4/2005 | Okada |
| 6,884,261 B2 | 4/2005 | Zadno-Azizi et al. |
| 6,884,263 B2 | 4/2005 | Valyunin et al. |
| 6,899,732 B2 | 5/2005 | Zadno-Azizi et al. |
| 6,905,641 B2 | 6/2005 | Platt et al. |
| 6,917,416 B2 | 7/2005 | Platt et al. |
| 6,921,416 B2 | 7/2005 | Khoury |
| 6,926,736 B2 | 8/2005 | Peng et al. |
| 6,960,230 B2 | 11/2005 | Haefliger |
| 6,960,231 B2 | 11/2005 | Tran |
| 6,972,033 B2 | 12/2005 | McNicholas |
| 6,986,900 B2 | 1/2006 | Yaacobi |
| 7,001,374 B2 | 2/2006 | Peyman |
| 7,001,427 B2 | 2/2006 | Aharoni et al. |
| 7,025,783 B2 | 4/2006 | Brady et al. |
| 7,029,497 B2 | 4/2006 | Zhang et al. |
| 7,041,134 B2 | 5/2006 | Nguyen et al. |
| 7,074,840 B2 | 7/2006 | Chang et al. |
| 7,087,080 B2 | 8/2006 | Zadno-Azizi et al. |
| 7,105,110 B2 | 9/2006 | Platt et al. |
| 7,118,596 B2 | 10/2006 | Zadno-Azizi et al. |
| 7,119,894 B2 | 10/2006 | Platt et al. |
| 7,122,053 B2 | 10/2006 | Esch |
| 7,125,422 B2 | 10/2006 | Woods |
| 7,134,755 B2 | 11/2006 | Jethmalani et al. |
| 7,144,423 B2 | 12/2006 | McDonald |
| 7,150,760 B2 | 12/2006 | Zhang |
| 7,198,640 B2 | 4/2007 | Nguyen |
| 7,210,783 B2 | 5/2007 | Jethmalani et al. |
| 7,223,288 B2 | 5/2007 | Zhang et al. |
| 7,226,478 B2 | 6/2007 | Ting et al. |
| 7,237,893 B2 | 7/2007 | Chang et al. |
| 7,241,009 B2 | 7/2007 | Kornfield et al. |
| 7,281,795 B2 | 10/2007 | Sandstedt et al. |
| 7,300,464 B2 | 11/2007 | Tran |
| 7,414,714 B2 | 8/2008 | Platt et al. |
| 7,452,362 B2 | 11/2008 | Zadno-Azizi et al. |
| 7,452,378 B2 | 11/2008 | Zadno-Azizi et al. |
| 7,462,193 B2 | 12/2008 | Nagamoto |
| 7,560,499 B2 | 7/2009 | Jethmalani et al. |
| 7,658,364 B2 | 2/2010 | Robinson et al. |
| 7,662,179 B2 | 2/2010 | Sarfarazi |
| 7,713,299 B2 | 5/2010 | Brady et al. |
| 7,744,603 B2 | 6/2010 | Zadno-Azizi et al. |
| 7,744,646 B2 | 6/2010 | Zadno-Azizi et al. |
| 7,771,471 B2 | 8/2010 | Dell |
| 7,780,729 B2 | 8/2010 | Nguyen et al. |
| 7,798,644 B2 | 9/2010 | Jethmalani et al. |
| 7,806,929 B2 | 10/2010 | Brown |
| 7,811,320 B2 | 10/2010 | Werblin et al. |
| 7,837,326 B2 | 11/2010 | Jethmalani et al. |
| 7,871,437 B2 | 1/2011 | Hermans et al. |
| 7,988,285 B2 | 8/2011 | Sandstedt et al. |
| 7,988,291 B2 | 8/2011 | Ianchulev |
| 8,025,823 B2 | 9/2011 | Pham et al. |
| 8,034,107 B2 | 10/2011 | Stenger |
| 8,048,155 B2 | 11/2011 | Shadduck |
| 8,052,752 B2 | 11/2011 | Woods et al. |
| 8,062,361 B2 | 11/2011 | Nguyen et al. |
| 8,088,161 B2 | 1/2012 | Aharoni et al. |
| 8,100,965 B2 | 1/2012 | Cumming |
| 8,128,693 B2 | 3/2012 | Tran et al. |
| 8,162,927 B2 | 4/2012 | Peyman et al. |
| 8,187,325 B2 | 5/2012 | Zadno-Azizi et al. |
| 8,197,539 B2 | 6/2012 | Nasiatka et al. |

(56) References Cited

U.S. PATENT DOCUMENTS

| | | |
|---|---|---|
| 8,246,679 B2 | 8/2012 | Nguyen et al. |
| 8,273,123 B2 | 9/2012 | Nun |
| 8,343,216 B2 | 1/2013 | Brady et al. |
| 8,361,353 B2 | 1/2013 | Brait et al. |
| 8,398,709 B2 | 3/2013 | Nun et al. |
| 8,486,142 B2 | 7/2013 | Bumbalough et al. |
| 8,505,822 B2 | 8/2013 | Wang et al. |
| 8,506,074 B2 | 8/2013 | Gerbaud |
| 8,545,556 B2 | 10/2013 | Woods et al. |
| 8,556,967 B2 | 10/2013 | Sarfarazi et al. |
| 8,574,295 B2 | 11/2013 | Roholt |
| 8,579,971 B2 | 11/2013 | Webb |
| 8,585,556 B2 | 11/2013 | Woods et al. |
| 8,585,758 B2 | 11/2013 | Woods |
| 8,608,799 B2 | 12/2013 | Blake et al. |
| 8,663,235 B2 | 3/2014 | Tassignon |
| 8,728,158 B2 | 5/2014 | Whitsett |
| 8,778,022 B2 | 7/2014 | Blum et al. |
| 8,821,166 B2 | 9/2014 | Akura et al. |
| 8,834,565 B2 | 9/2014 | Nun |
| 8,900,300 B1 | 12/2014 | Wortz |
| 8,915,588 B2 | 12/2014 | Blum et al. |
| 8,931,896 B2 | 1/2015 | Blum et al. |
| 9,005,282 B2 | 4/2015 | Chang et al. |
| 9,005,283 B2 | 4/2015 | Nguyen et al. |
| 9,039,760 B2 | 5/2015 | Brady et al. |
| 9,072,600 B2 | 7/2015 | Tran |
| 9,078,744 B2 | 7/2015 | Van Noy |
| 9,095,424 B2 | 8/2015 | Kahook et al. |
| 9,119,710 B2 | 9/2015 | Grubbs et al. |
| 9,124,796 B2 | 9/2015 | Blum et al. |
| 9,125,736 B2 | 9/2015 | Kahook et al. |
| 9,149,356 B2 | 10/2015 | Sarfarazi |
| 9,173,527 B2 | 11/2015 | Ulrich et al. |
| 9,186,243 B2 | 11/2015 | Van Noy |
| 9,198,752 B2 | 12/2015 | Woods |
| 9,289,287 B2 | 3/2016 | Kahook et al. |
| 9,339,375 B2 | 5/2016 | Lee et al. |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,439,754 B2 | 9/2016 | Wortz |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,554,890 B2 | 1/2017 | Wortz et al. |
| 9,597,176 B2 | 3/2017 | Wortz et al. |
| 9,629,712 B2 | 4/2017 | Stenger |
| 9,642,699 B2 | 5/2017 | Wortz et al. |
| 9,681,946 B2 | 6/2017 | Kahook et al. |
| 9,763,771 B1 | 9/2017 | Wortz et al. |
| 9,925,037 B2 | 3/2018 | Wortz et al. |
| 9,993,336 B2 | 6/2018 | Wortz et al. |
| 10,004,594 B2 | 6/2018 | Wortz et al. |
| 10,111,746 B2 | 10/2018 | Wortz et al. |
| 10,136,989 B2 | 11/2018 | Wortz et al. |
| 10,271,945 B2 | 4/2019 | Wortz et al. |
| 10,492,903 B1 | 12/2019 | Wortz et al. |
| 10,603,162 B2 | 3/2020 | Wortz et al. |
| 10,743,983 B2 | 8/2020 | Wortz et al. |
| 10,813,745 B2 | 10/2020 | Wortz |
| 10,820,985 B2 | 11/2020 | Wortz |
| 10,842,615 B2 | 11/2020 | Wortz et al. |
| 10,898,315 B2 | 1/2021 | Wortz et al. |
| 11,007,050 B1 | 5/2021 | Wortz |
| 11,013,592 B1 | 5/2021 | Wortz |
| 11,033,381 B2 | 6/2021 | Wortz |
| 11,213,381 B2 | 1/2022 | Wortz |
| 11,278,394 B2 | 3/2022 | Wortz et al. |
| 2001/0047204 A1 | 11/2001 | Zhou et al. |
| 2001/0051825 A1 | 12/2001 | Peterson |
| 2002/0128719 A1 | 9/2002 | Eggleston |
| 2002/0143395 A1 | 10/2002 | Skottun |
| 2002/0173846 A1 | 11/2002 | Blake et al. |
| 2003/0004569 A1 | 1/2003 | Haefliger |
| 2003/0050695 A1 | 3/2003 | Lin et al. |
| 2003/0090624 A1 | 5/2003 | Jethmalani et al. |
| 2003/0149479 A1 | 8/2003 | Snyder et al. |
| 2003/0149480 A1 | 8/2003 | Shadduck |
| 2003/0151831 A1 | 8/2003 | Sandstedt et al. |
| 2003/0176521 A1 | 9/2003 | Jethmalani et al. |
| 2003/0187505 A1 | 10/2003 | Liao |
| 2004/0064182 A1 | 4/2004 | Kelman |
| 2004/0082993 A1 | 4/2004 | Woods |
| 2004/0082995 A1 | 4/2004 | Woods |
| 2004/0106993 A1 | 6/2004 | Portney |
| 2004/0117011 A1 | 6/2004 | Aharoni et al. |
| 2004/0148022 A1 | 7/2004 | Eggleston |
| 2004/0158322 A1 | 8/2004 | Shen et al. |
| 2004/0167622 A1 | 8/2004 | Sunlap et al. |
| 2004/0208910 A1 | 10/2004 | Ashton et al. |
| 2004/0254438 A1 | 12/2004 | Chuck et al. |
| 2005/0021138 A1 | 1/2005 | Woods |
| 2005/0085907 A1 | 4/2005 | Hanna |
| 2005/0099597 A1 | 5/2005 | Sandstedt et al. |
| 2005/0107875 A1 | 5/2005 | Cumming |
| 2005/0113911 A1 | 5/2005 | Peyman |
| 2005/0113913 A1 | 5/2005 | Duvert et al. |
| 2005/0137703 A1 | 6/2005 | Chen |
| 2005/0154457 A1 | 7/2005 | Aharoni et al. |
| 2005/0187623 A1 | 8/2005 | Tassignon |
| 2005/0222577 A1 | 10/2005 | Vaquero |
| 2005/0234285 A1 | 10/2005 | Khoury |
| 2005/0246018 A1 | 11/2005 | Grubbs et al. |
| 2006/0027939 A1 | 2/2006 | Brait et al. |
| 2006/0047339 A1 | 3/2006 | Brown |
| 2006/0064161 A1 | 3/2006 | Blake |
| 2006/0095128 A1 | 5/2006 | Blum et al. |
| 2006/0212116 A1 | 9/2006 | Woods |
| 2006/0253196 A1 | 11/2006 | Woods |
| 2006/0259139 A1 | 11/2006 | Zadno-Azizi et al. |
| 2006/0261502 A1 | 11/2006 | Platt et al. |
| 2007/0027538 A1 | 2/2007 | Aharoni et al. |
| 2007/0027541 A1 | 2/2007 | Aharoni et al. |
| 2007/0032868 A1 | 2/2007 | Woods |
| 2007/0083261 A1 | 4/2007 | Colvard |
| 2007/0093892 A1 | 4/2007 | MacKool |
| 2007/0100444 A1 | 5/2007 | Brady et al. |
| 2007/0118216 A1 | 5/2007 | Pynson |
| 2007/0123767 A1 | 5/2007 | Montegrande et al. |
| 2007/0123981 A1 | 5/2007 | Tassignon |
| 2007/0162118 A1 | 7/2007 | Rozakis et al. |
| 2007/0213816 A1 | 9/2007 | Sarfarazi |
| 2007/0244560 A1 | 10/2007 | Ossipov et al. |
| 2007/0260308 A1 | 11/2007 | Tran |
| 2008/0086206 A1 | 4/2008 | Nasiatka et al. |
| 2008/0097599 A1 | 4/2008 | Rozakis et al. |
| 2008/0221676 A1 | 9/2008 | Coleman et al. |
| 2008/0300680 A1 | 12/2008 | Joshua |
| 2009/0005864 A1 | 1/2009 | Eggleston |
| 2009/0182423 A1 | 7/2009 | Zheng |
| 2010/0022945 A1 | 1/2010 | Rodstrom |
| 2010/0030225 A1 | 2/2010 | Ianchulev |
| 2010/0204788 A1 | 8/2010 | Van Noy |
| 2010/0211171 A1 | 8/2010 | Sarfarazi |
| 2010/0228344 A1 | 9/2010 | Shadduck |
| 2010/0280609 A1 | 11/2010 | Simonov et al. |
| 2011/0015541 A1 | 1/2011 | Padrick et al. |
| 2011/0040378 A1 | 2/2011 | Werblin |
| 2011/0153014 A1 | 6/2011 | Zhang et al. |
| 2011/0181834 A1 | 7/2011 | Gerbaud |
| 2011/0224788 A1 | 9/2011 | Webb |
| 2011/0288638 A1 | 11/2011 | Smiley et al. |
| 2011/0295367 A1 | 12/2011 | Cuevas |
| 2011/0313521 A1 | 12/2011 | Angelopoulos |
| 2012/0078363 A1 | 3/2012 | Lu et al. |
| 2012/0078364 A1* | 3/2012 | Stenger ............... A61F 2/1629 623/6.39 |
| 2012/0179249 A1 | 7/2012 | Coleman |
| 2012/0226351 A1 | 9/2012 | Peyman |
| 2012/0238857 A1 | 9/2012 | Wong et al. |

(56) References Cited

U.S. PATENT DOCUMENTS

| | | |
|---|---|---|
| 2012/0253458 A1 | 10/2012 | Geraghty et al. |
| 2013/0072591 A1 | 3/2013 | Sandstedt et al. |
| 2013/0110233 A1 | 5/2013 | Ghabra |
| 2013/0116781 A1 | 5/2013 | Nun |
| 2013/0184815 A1 | 7/2013 | Roholt |
| 2013/0190868 A1 | 7/2013 | Kahook et al. |
| 2013/0197637 A1 | 8/2013 | Brait et al. |
| 2013/0245754 A1 | 9/2013 | Blum et al. |
| 2013/0289153 A1 | 10/2013 | Sandstedt et al. |
| 2013/0304206 A1 | 11/2013 | Pallikaris et al. |
| 2013/0310931 A1 | 11/2013 | Kahook et al. |
| 2013/0317458 A1 | 11/2013 | Kopczynski et al. |
| 2014/0052246 A1 | 2/2014 | Kahook et al. |
| 2014/0067059 A1 | 3/2014 | Webb |
| 2014/0172089 A1 | 6/2014 | Lee et al. |
| 2014/0228949 A1 | 8/2014 | Argento et al. |
| 2014/0343379 A1 | 11/2014 | Pugh |
| 2014/0371852 A1 | 12/2014 | Aharoni et al. |
| 2014/0379079 A1 | 12/2014 | Ben Nun |
| 2015/0061990 A1 | 3/2015 | Toner et al. |
| 2015/0088253 A1 | 3/2015 | Doll et al. |
| 2015/0100046 A1 | 4/2015 | Ambati et al. |
| 2015/0157452 A1 | 6/2015 | Maliarov et al. |
| 2015/0182330 A1 | 7/2015 | Grant |
| 2015/0223930 A1* | 8/2015 | Shiuey ............... A61F 2/1451 623/5.14 |
| 2015/0230981 A1 | 8/2015 | Kahook et al. |
| 2015/0238309 A1 | 8/2015 | Jansen et al. |
| 2015/0272727 A1 | 10/2015 | Humayun et al. |
| 2015/0289970 A1 | 10/2015 | Akura |
| 2015/0335420 A1 | 11/2015 | Blum et al. |
| 2015/0366660 A1 | 12/2015 | Martinez et al. |
| 2016/0000558 A1 | 1/2016 | Honigsbaum |
| 2016/0008126 A1 | 1/2016 | Salahieh et al. |
| 2016/0030161 A1 | 2/2016 | Brady et al. |
| 2016/0030163 A1 | 2/2016 | Akahoshi |
| 2016/0058552 A1 | 3/2016 | Argal et al. |
| 2016/0058553 A1 | 3/2016 | Salahieh et al. |
| 2016/0074154 A1 | 3/2016 | Woods |
| 2016/0113760 A1 | 4/2016 | Conrad |
| 2016/0113761 A1 | 4/2016 | Nishi et al. |
| 2016/0278912 A1 | 9/2016 | Kahook et al. |
| 2016/0310263 A1 | 10/2016 | Akura |
| 2016/0317287 A1 | 11/2016 | Silvestrini et al. |
| 2016/0324629 A1 | 11/2016 | Sandstedt et al. |
| 2016/0331519 A1 | 11/2016 | Kahook et al. |
| 2016/0339657 A1 | 11/2016 | Grubbs et al. |
| 2017/0000602 A1 | 1/2017 | Sohn et al. |
| 2017/0020658 A1 | 1/2017 | Grubbs et al. |
| 2017/0042667 A1 | 2/2017 | Collins et al. |
| 2017/0049560 A1 | 2/2017 | Cherne |
| 2017/0119521 A1 | 5/2017 | Kahook et al. |
| 2017/0172732 A1 | 6/2017 | Lu et al. |
| 2017/0319332 A1 | 11/2017 | Kahook et al. |
| 2017/0348094 A1 | 12/2017 | Sohn |
| 2018/0147049 A1 | 5/2018 | Park |
| 2018/0271645 A1* | 9/2018 | Brady ............... B29D 11/026 |
| 2019/0105152 A1* | 4/2019 | Pallikaris ............ A61F 2/1645 |
| 2019/0307552 A1* | 10/2019 | Wortz ............... A61F 2/1694 |
| 2019/0374334 A1* | 12/2019 | Brady ............... A61F 2/1618 |
| 2020/0261216 A1 | 8/2020 | Wortz |
| 2021/0113326 A1 | 4/2021 | Wortz |
| 2021/0128295 A1 | 5/2021 | Wortz |
| 2021/0275203 A1 | 9/2021 | Wortz |

FOREIGN PATENT DOCUMENTS

| | | |
|---|---|---|
| EP | 0 294 039 | 7/1993 |
| EP | 0 528 325 | 12/1996 |
| EP | 1 653 886 | 5/2006 |
| EP | 1 499 264 | 8/2006 |
| EP | 1 100 411 | 11/2006 |
| EP | 1 694 253 | 8/2007 |
| EP | 1 852 090 | 11/2007 |
| EP | 1 562 521 | 12/2009 |
| EP | 1 475 055 | 4/2010 |
| EP | 1 933 768 | 10/2010 |
| EP | 2 315 559 | 5/2011 |
| EP | 1 438 930 | 9/2011 |
| EP | 2 412 337 | 2/2012 |
| EP | 1 296 616 | 5/2012 |
| EP | 1 906 881 | 8/2012 |
| EP | 2 512 374 | 10/2012 |
| EP | 2 851 038 | 3/2015 |
| EP | 2 620 130 | 7/2016 |
| FR | 2 799 637 | 4/2001 |
| FR | 2 804 860 | 8/2001 |
| FR | 2 966 340 | 4/2012 |
| JP | S63-89154 | 4/1988 |
| JP | H09-173363 | 7/1997 |
| JP | 2005-143886 | 6/2005 |
| JP | 2013-544116 | 12/2013 |
| JP | 2017-519221 | 7/2017 |
| WO | WO 98/017205 | 4/1998 |
| WO | WO 99/024541 | 5/1999 |
| WO | WO 99/062433 | 12/1999 |
| WO | WO 01/64136 | 9/2001 |
| WO | WO 02/026121 | 4/2002 |
| WO | WO 02/071983 | 9/2002 |
| WO | WO 03/058296 | 7/2003 |
| WO | WO 05/016191 | 2/2005 |
| WO | WO 05/094727 | 10/2005 |
| WO | WO 05/107649 | 11/2005 |
| WO | WO 06/002201 | 1/2006 |
| WO | WO 06/050171 | 5/2006 |
| WO | WO 06/124016 | 11/2006 |
| WO | WO 06/135572 | 12/2006 |
| WO | WO 07/030799 | 3/2007 |
| WO | WO 06/015315 | 4/2007 |
| WO | WO 07/121296 | 10/2007 |
| WO | WO 10/002215 | 4/2010 |
| WO | WO 11/163080 | 12/2011 |
| WO | WO 12/067994 | 5/2012 |
| WO | WO 12/161749 | 11/2012 |
| WO | WO 13/039707 | 3/2013 |
| WO | WO 13/112589 | 8/2013 |
| WO | WO 14/167425 | 10/2014 |
| WO | WO 14/197170 | 12/2014 |
| WO | WO 14/201956 | 12/2014 |
| WO | WO 15/044235 | 4/2015 |
| WO | WO 15/066532 | 5/2015 |
| WO | WO 15/126604 | 8/2015 |
| WO | WO 15/198236 | 12/2015 |
| WO | WO 15/200056 | 12/2015 |
| WO | WO 16/122805 | 8/2016 |
| WO | WO 16/187497 | 11/2016 |
| WO | WO 17/030582 | 2/2017 |
| WO | WO 17/079449 | 5/2017 |
| WO | WO 17/192855 | 11/2017 |
| WO | WO 18/075932 | 4/2018 |
| WO | WO 19/236908 | 12/2019 |

OTHER PUBLICATIONS

Becker et al., "Accuracy of Lens Power Calculation and Centration of an Aspheric Intraocular Lens", Der Ophthalmologe: Zeitschrift der Deutschen Ophthalmologischen Gesellschaft, Oct. 2006, 103(10):873-876.

Guttman-Krader Cheryl, "Small-aperture optic IOL broadens range of vision", Article in Ophthalmology Times on Dec. 1, 2014 in 6 pages.

Kleiman et al., "Post-operative Results with Implantation of the Acrysof SA-60 Intraocular lens into the Ciliary Sulcus", Invest Ophthalmol. Vis Sci. May 2002, 43:E-Abstract 380 in 2 pages.

Kleinmann Guy, "Open-Capsule Device for PCO Prevention", Power Point Presentation for Hanita Lenses, Oct. 17, 2013 in 20 pages.

Koeppl et al., "Change in IOL position and capsular bag size with an angulated intraocular lens early after cataract surgery", J Cataract Refractive Surg. Feb. 2005, 31(2):348-353.

(56) References Cited

OTHER PUBLICATIONS

Lim et al., "Surgical management of late dislocated lens capsular bag with intraocular lens and endocapsular tension ring", J Cataract Refractive Surg., Mar. 2006, 32(3):533-535.
Review of Optometry, "Tracking IOP With an IOL", Sep. 15, 2014 in 1 page.
Wirtitsch et al., "Effect of haptic design on change in axial lens position after cataract surgery", J Catar Refractive Surg., Jan. 2004, (30)1:45-51.
International Search Report and Written Opinion dated Feb. 3, 2022 in application No. PCT/US2021/071823.

\* cited by examiner

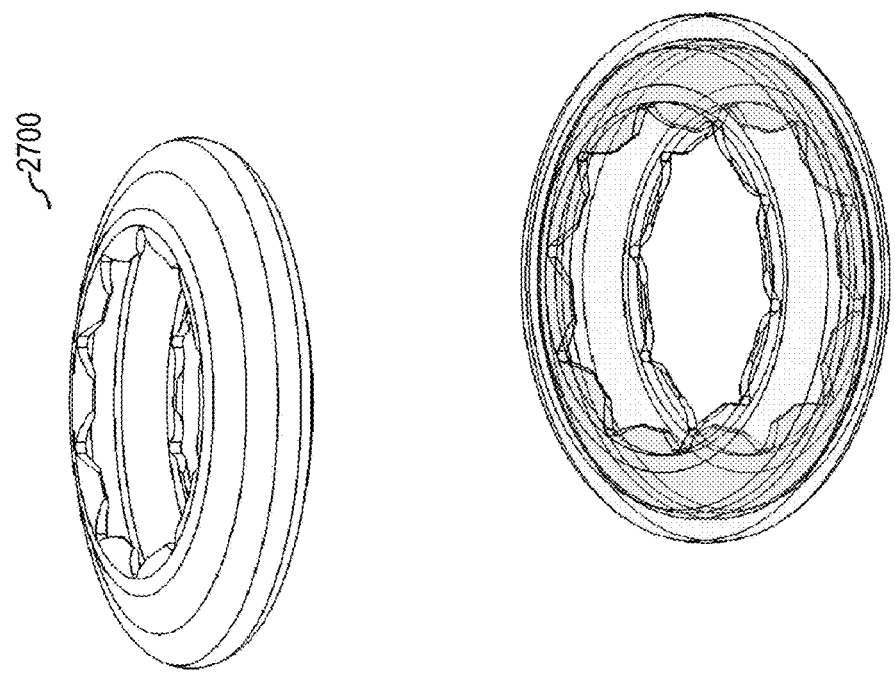
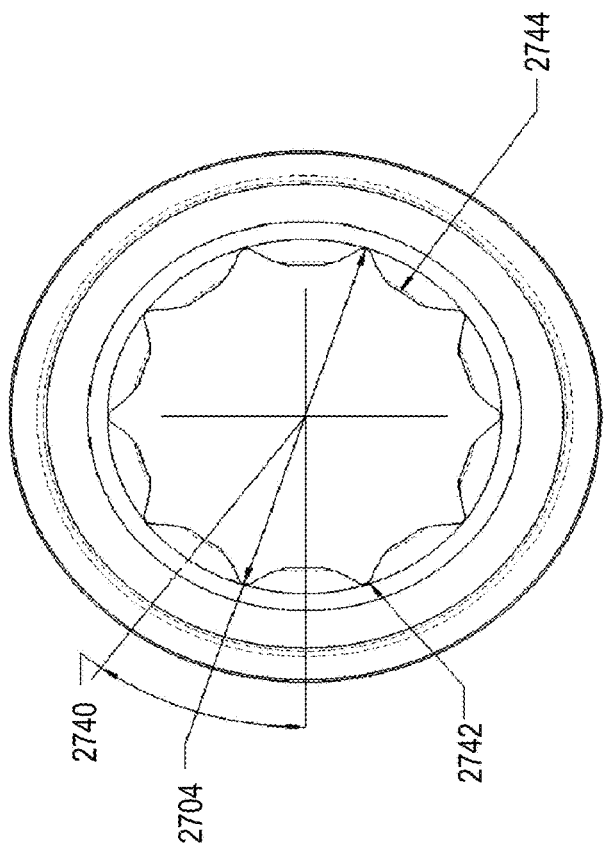
FIG. 27

PROSTHETIC CAPSULAR DEVICES, SYSTEMS, AND METHODS

INCORPORATION BY REFERENCE TO ANY PRIORITY APPLICATIONS

The present application claims the benefit under 35 U.S.C. § 119(c) of U.S. Provisional Patent Application No. 63/090,426, filed Oct. 12, 2020, U.S. Provisional Patent Application No. 63/091,183, filed Oct. 13, 2020, and U.S. Provisional Patent Application No. 63/149,153, filed Feb. 12, 2021, each of which is incorporated herein by reference in its entirety under 37 C.F.R. § 1.57. Any and all applications for which a foreign or domestic priority claim is identified in the Application Data Sheet as filed with the present application are hereby incorporated by reference under 37 CFR 1.57.

BACKGROUND

Field

The present application relates to prosthetic capsular devices, systems, and methods for insertion into the eye.

DESCRIPTION

Cataract surgery is one of the most successfully and most frequently performed surgical procedures in the United States. Each year, millions of people achieve a dramatic improvement in their visual function thanks to this procedure. With the increasing proportion of the U.S. population reaching their retirement years, there is expected to be an almost doubling of the demand for cataract surgery over the next twenty years from 3.3 million to over 6 million annually. In response to the increased demand, more ophthalmologists may be trained and certified to perform cataract surgery, and each trained and certified ophthalmologist may perform more cataract surgeries each year.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

Some embodiments herein are directed to a prosthetic capsular device configured to be inserted in a natural capsular bag of an eye, the prosthetic capsular device comprising: a housing structure comprising: an anterior portion comprising: an anterior circular opening; an anterior rim surrounding the anterior circular opening and defining a perimeter of the anterior circular opening, the anterior rim comprising a first curved portion originating at the perimeter of the anterior circular opening and extending laterally outward and anteriorly from the perimeter of the anterior circular opening; and an anterior sidewall connected to the anterior rim and extending laterally outward and posteriorly from the anterior rim, the anterior sidewall comprising a first exterior curved surface and a first interior surface comprising a first straight portion and a second straight portion, wherein the first straight portion extends from the anterior rim to a first transition point of the first interior surface, and wherein the second straight portion extends from the first transition point of the first interior surface to a longitudinal center plane of the housing structure; a posterior portion comprising: a posterior circular opening; a posterior rim surrounding the posterior circular opening and defining a perimeter of the posterior circular opening, the posterior rim comprising a second curved portion originating at the perimeter of the posterior opening and extending laterally outward and posteriorly from the perimeter of the posterior circular opening; and a posterior sidewall connected to the posterior rim and extending laterally outward and anteriorly from the posterior rim, the posterior sidewall comprising a second exterior curved surface and a second interior surface comprising a third straight portion and a fourth straight portion, wherein the third straight portion extends from the posterior rim to a first transition point of the second interior surface, and wherein the fourth straight portion extends from the first transition point of the second interior surface to the longitudinal center plane of the housing structure; an interior cavity formed between the anterior circular opening and the posterior circular opening, the interior cavity configured to house an intraocular lens; and a groove formed by one or more ribs, the one or more ribs formed along a circumference of the interior cavity at the longitudinal center plane of the housing structure, wherein each rib of the one or more ribs comprises a top surface and a bottom surface formed a rib angle, and wherein the groove is configured to hold the intraocular lens in place within the interior cavity of the housing structure.

In some embodiments, the first exterior curved surface and the second exterior curved surface are continuous surfaces with substantially no openings. In some embodiments, the first exterior curved surface and the second exterior curved surface connect at the longitudinal center plane of the housing structure.

In some embodiments, the housing structure is symmetrical, such that the anterior portion and the posterior portion are mirror images. In some embodiments, the interior cavity is configured to house the intraocular lens of at least the following types: spherical, aspheric, wavefront, convex, concave, extended depth of focus, pinhole or small aperture, multifocal, toric, accommodative, ultraviolet (UV) filtering, diffractive chromatic aberration reducing, light adjustable, positive diopter, and negative diopter.

In some embodiments, the prosthetic capsular device is made of silicone or silicone polymer. In some embodiments, the prosthetic capsular device is manufactured by compression molding, three-dimensional laser cutting, two photon lithography, additive manufacturing, or a combination of the above. In some embodiments, the prosthetic capsular device comprises a flexible or elastic material, such that the prosthetic capsular device is foldable and self-expandable.

In some embodiments, a thickness of the anterior sidewall and the posterior sidewall is between about 0.1 mm and 1.0 mm. In some embodiments, the rib angle is about 100°. In some embodiments, the groove is formed by 12 ribs.

In some embodiments, the first straight portion and the third straight portion are formed at a sidewall angle. In some embodiments, the sidewall angle is about 34° or about 57°.

In some embodiments, the interior cavity comprises a volume for maintaining the shape and size of the natural capsular bag.

In some embodiments, the device further comprises one or more notches located on an exterior surface of the housing structure, protruding radially outward from the exterior surface. In some embodiments, the one or more notches contact or engage a surface of the natural capsular bag. In some embodiments, the one or more notches are located along the longitudinal center plane of the housing structure.

In some embodiments, the device further comprises one or more ridges extending longitudinally from the anterior circular opening to the posterior circular opening. In some embodiments, the one or more ridges are located intermittently around a circumference of the exterior of the device. In some embodiments, an exterior surface of the housing comprises a textured surface, the textured surface comprising an adhesive, nanostructures, or micro-structures formed on the exterior surface.

BRIEF DESCRIPTION OF THE DRAWINGS

The drawings are provided to illustrate example embodiments and are not intended to limit the scope of the disclosure. A better understanding of the systems and methods described herein will be appreciated upon reference to the following description in conjunction with the accompanying drawings, wherein:

FIG. 27 illustrates another example prosthetic capsular device according to some embodiments herein.

DETAILED DESCRIPTION

Figure 1:
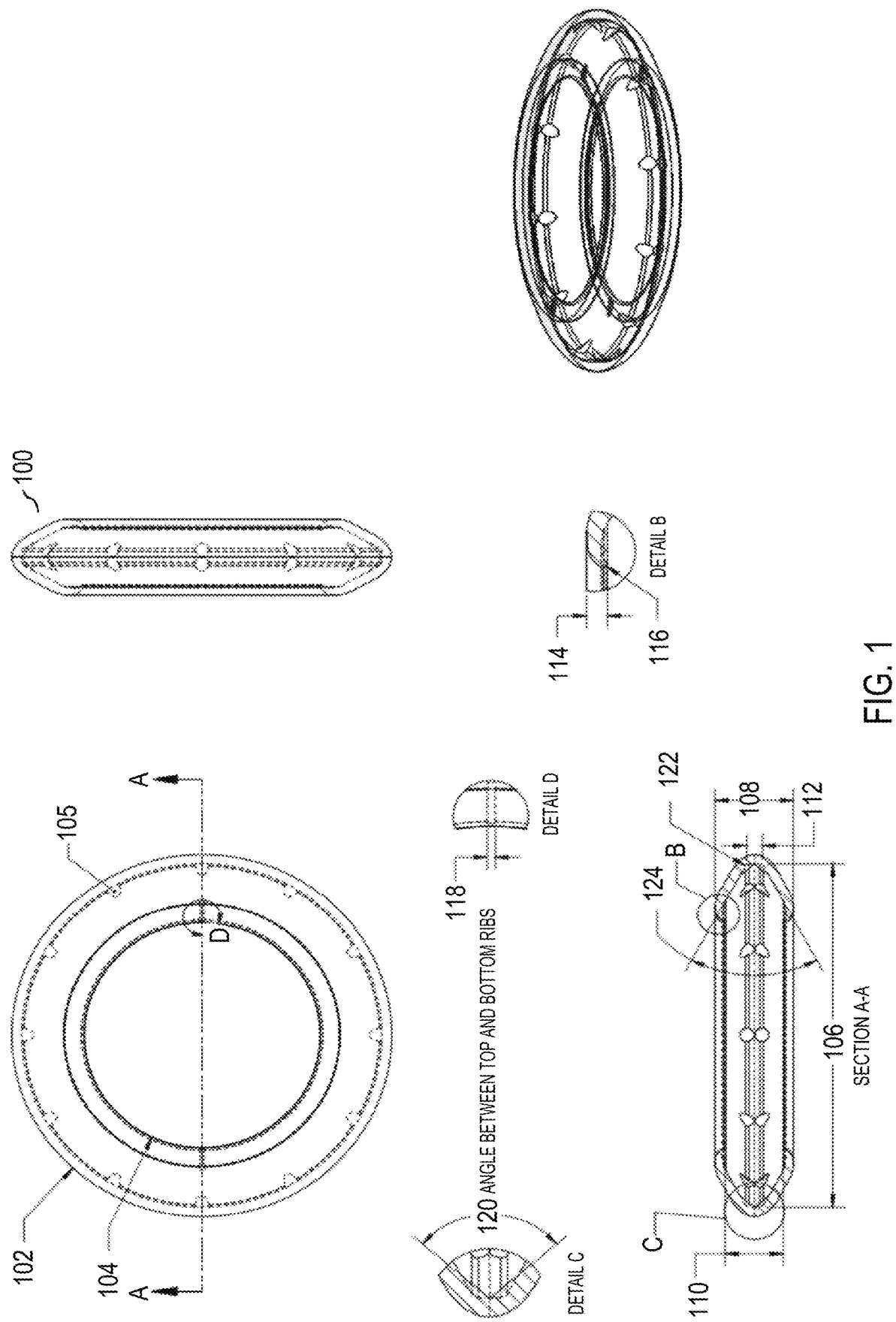
FIG. 1 illustrates an example prosthetic capsular device according to some embodiments herein.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present technology.

Devices and methods that help provide the desired refractive endpoint in cataract surgery are described in U.S. Pat. Nos. 8,900,300, 9,414,907, 9,358,103, and 10,603,162, each of which is hereby incorporated by reference in its entirety. All patents, patent applications, and other documents referred to in this application are incorporated by reference herein in their entirety. The disclosure of U.S. Pat. No. 10,603,162 is attached to this application as Appendix A.

In addition to the increase in demand for cataract surgery, technological advances have increased patient expectations for the surgery. The procedure takes a short amount of time to perform, and patients expect quick recovery of visual function. Patients are also asking their ophthalmologist to give them the restoration of more youthful vision without glasses through the use multifocal intraocular lenses, extended depth of focus lenses, accommodating lenses, other presbyopia correcting lenses, toric lenses, and monovision, to name a few. Despite accurate preoperative measurements and excellent surgical technique, post-surgical outcomes may vary due to undesirable physiological interaction with surgical implants.

Some embodiments herein are directed to prosthetic capsular devices and methods that address problems associated with prior devices. For example, the prosthetic capsular devices herein may be designed to eliminate, reduce, or mitigate contact between the iris pigment epithelium of an eye with the prosthetic capsular device. Implantation of an intraocular lens (IOL) or previous prosthetic capsular devices has become a routine practice among many surgeons, and several studies describe advantages of fixation of IOLs and other devices within the natural capsular bag. However, posterior iris chafing by the devices and IOLs may cause pigment dispersion and related inflammatory complications, specifically, the well described Uveitis-Glaucoma-Hyphema (UGH) syndrome. For example, the chafing may cause blurred vision, ocular pain, and headaches, pigmentary dispersion within the eye and on the IOL surface, iris trans illumination defects, iris changes including vacuolization/disruption/loss of the pigmented layer, iris thinning and iris atrophy, among others. With increased pigment shedding from the iris, the eye may experience iris transillumination defects, deposition of pigment of the corneal endothelium (Krukenbergs spindle), and angle pigmentation along the trabecular meshwork. Without being limited by any particular theory, it is postulated that the size and shape, including relatively large anterior-posterior thicknesses and sharp or straight edges, of previous prosthetic devices caused or contributed to this chafing and related complications. Thus, the prosthetic devices described herein are designed to eliminate, reduce, or mitigate posterior iris chafing.

Another problem associated with previous IOLs and prosthetic devices with implanted IOLs is lens tilt. Lens tilt occurs when the angle between the optical axis and the visual axis of the IOL are not colinear, which may occur if the IOL becomes misplaced within the natural capsular bag and/or the prosthetic capsular device. Lens tilt, along with decentration of the IOL, may cause suboptimal refractive outcomes for patients. For example, lens tilt may result in astigmatism and higher order aberrations. Large amounts of IOL tilt or decentration may cause enough astigmatism to significantly affect quality of vision. Multifocal, toric and toric multi-focal are more sensitive to small changes in tilt compared to monofocal IOLs and centration parameters need to be particularly accurate and precise. Thus, the prosthetic capsular devices described herein may be configured to secure IOLs therein such that the possibility of lens tilt and/or decentration is minimized.

Figure 2:
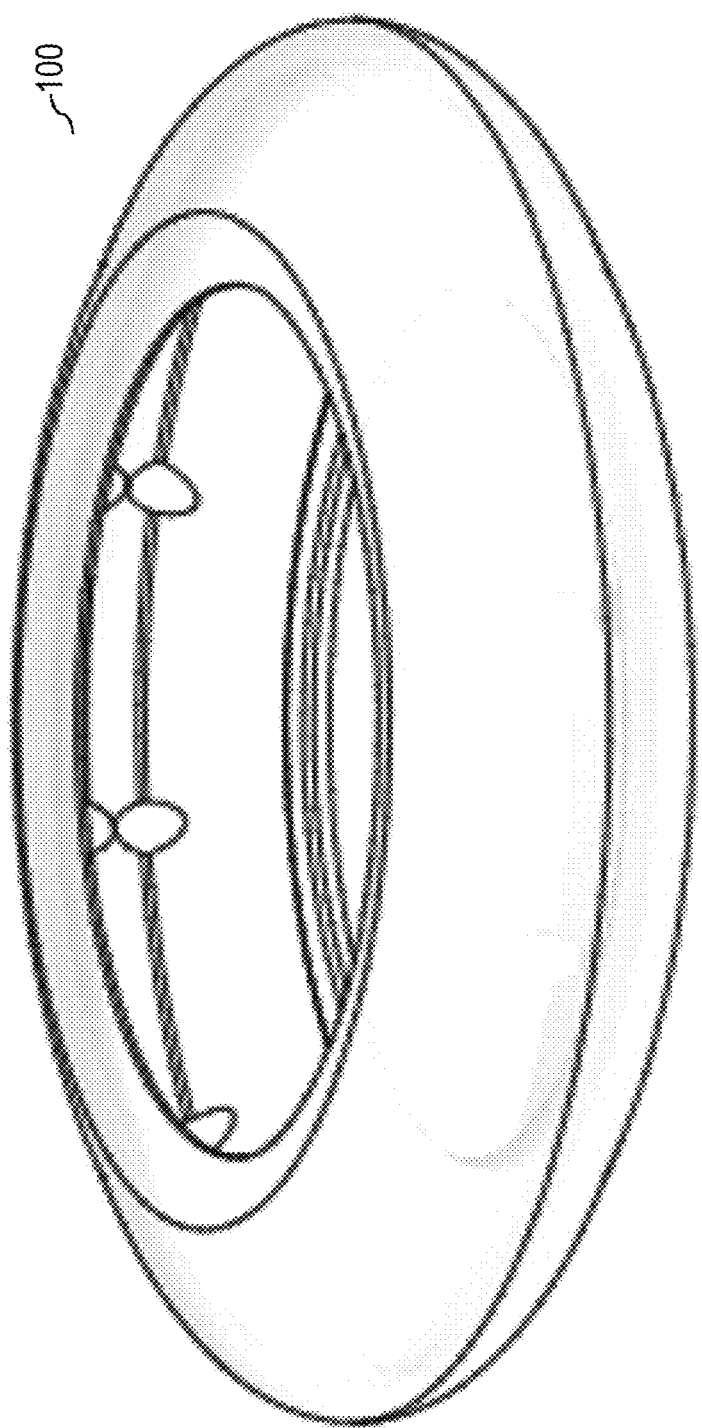
FIG. 2 is an anterior side perspective view of the example prosthetic capsular device of FIG. 1.

FIG. 1 illustrates various perspective views of an example of a prosthetic capsular device 100. In some embodiments, the device 100 includes features described with respect to the devices described in U.S. Pat. No. 10,603,162, which is hereby incorporated by reference in its entirety, or modifications thereof. FIG. 2 is an anterior side perspective view of the example prosthetic capsular device of FIG. 1.

In some embodiments, the device 100 includes features described with respect to the devices described in U.S. Pat. No. 9,358,103, which is hereby incorporated by reference in its entirety, or modifications thereof. For example, the device 100 can comprise an anterior side, a posterior side, and one or more sidewalls extending between the anterior side and the posterior side; a cavity or opening defined by the anterior side, posterior side, and the one or more sidewalls. The device 100 can be configured to comprise one or more intraocular lenses, electronic devices, or other intraocular devices held within the cavity. The IOLs may comprise any and all lens powers and designs that are currently known in the art of intraocular lenses, including, but not limited to: spherical, aspheric, wavefront, convex, concave, extended depth of focus, pinhole or small aperture, multifocal (diffractive, refractive, zonal), toric, accommodative, ultraviolet (UV) filtering, diffractive chromatic aberration reducing lenses, light adjustable lenses (ultraviolet light adjustable, femtosecond phase wrapping), and optical powers ranging from any positive diopter value (e.g., including +35 D and above) to any negative diopter value (e.g., including −35 D and below).

Further, in certain embodiments, the device 100 includes one or more additional features. For example, the device 100 can comprise a generally lenticular or lens-like shape as opposed to a box-like design. In other words, the generally shape of the device 100 can be more like the shape of a natural lens. Risks of negative and/or positive dysphotopsia can be reduced due to the generally lenticular shape of the device 100. Negative dysphotopsia is a common problem in cataract surgery, generally described by patients as a temporal dark crescent in their vision and is believed to occur either due to the optical phenomenon known as total internal reflection or by obstruction of light. This can occur either at the junction of the optic edge and the empty collapsed surrounding capsule forming a relatively planar surface, or due to the capsule overlapping a portion of the optic, most commonly the nasal aspect. In embodiments in which the implantable device 100 comprises an overall lens-like configuration, the capsule can be held open, preventing a relatively planar surface from being formed by fusion of the posterior and anterior capsule. More specifically, when light hits a curvilinear slice of the device 100, which can be made from silicone for example, it may travel through the curvilinear slice instead of bouncing off and causing a negative shadow as it generally would for flat surfaces. This may be especially true in the horizontal meridian across the 180-degree plane. As such, in some embodiments, the device 100 does not comprise any flat edges or surfaces. In other words, every surface of the device 100 can be curvilinear. Flat optical surfaces can promote total internal reflection, and are not found in the natural human lens or lens capsule in the native state. One goal of some of the embodiments described herein is to reduce negative dysphotopsias by not having any flat optical surfaces. Certain embodiments may have additional features such as an opaque or translucent tint. This may further enhance the reduction of positive dysphotopsias by blocking stray light that could be reflected off of the IOL border or haptic edges. This could also function as an artificial iris of sorts, depending on the color and opacity of the tint, blocking light that could be transmitted through an iris transillumination defect, a traumatically altered iris, or a surgical peripheral iridotomy, likewise preventing positive dysphotopsias and glare.

In some embodiments, substantially the whole device 100 can comprise silicone and/or a soft silicone polymer. In addition, in certain embodiments, substantially the whole device 100 can comprise a flexible and/or elastic material. As such, the device 100 can be foldable or collapsible for implantation into the eye through a small incision. Once inserted into the eye, the device 100 can naturally unfold and self-expand into its expanded configuration as illustrated in FIG. 1. The device 100 can comprise one or more capsular areas. The one or more capsular areas can be adapted to receive and/or hold an IOL. In some embodiments, the one or more sidewalls can comprise a concave shape. For example, an interior surface of the one or more sidewalls can form a cavity. The cavity can be configured to hold an IOL, for example.

In some embodiments, the device 100 comprises a single-molded design. In other words, the whole device 100, or substantially the whole device 100 can be molded from a single piece of material. For example, in some embodiments, substantially the whole device 100 can be molded of silicone using a silicone compression mold. In other embodiments, the device 100 or any portion thereof can be manufactured by 3D laser cutting, two photon lithography, additive manufacturing, 3D printing, compression molding, and/or any combination of the aforementioned manufacturing processes or others.

In some embodiments, the device 100 can be inserted through an incision between about 1.5 mm and about 3 mm (e.g., about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, ranges between such values, etc.).

Further, in some embodiments, a length of a major axis of the device 100 or a length measured from the outermost end of one sidewall to the outermost end of another sidewall along a major axis of the device 100 can be about 9.65 mm. In other embodiments, the length of the major axis of the device 100 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 100 may comprise a diameter 102 of the device 100.

In some embodiments, the thickness of silicone or other material of the device 100 can be about 0.25 mm. In certain embodiments, the thickness of silicone or other material of the device 100 can be about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, and/or within a range defined by two of the aforementioned values.

In some embodiments, the thickness of the silicone or other material of the device 100 varies depending on the portion of the device 100. In other words, some portions of the device 100 can be made of thinner materials while other portions of the device 100 can be made of thicker materials. For example, certain portions of the device that provide support to the anterior portion of the device 100 may be made with thicker materials for added support.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 104, which can be a diameter of an anterior opening and/or a posterior opening.

In some embodiments, the shape and size of the device 100 may minimize anterior, posterior, and/or radial protrusion into the natural capsular bag relative to previously used capsular devices. In some embodiments, the device 100 may be smaller in certain dimensions especially towards the anterior and periphery of the device. In some embodiments, sharp and/or straight edges or sides may not be present in the device 100 to reduce friction between the device 100 and the posterior aspect of the iris of an eye. In some embodiments, the smaller size, decrease in anterior, posterior, and/or radial protrusion into the natural capsular bag, and smoothened or curved edges, may result in the device 100 having an enhanced biocompatibility profile and/or may reduce inflammation caused by the device in the eye. In some embodiments, the unique shape and design of the device 100 may result in a decrease and/or elimination of inflammation of the eye (e.g. anterior of the eye) upon insertion of the device. In some embodiments, the decrease and/or elimination of post-insertion inflammation resulting from the shape of the device 100 may result in a decrease and/or elimination of the need for post-operative anti-inflammatory medications such as, e.g., steroids or nonsteroidal anti-inflammatory drugs (NSAIDs). It may also result in a decrease and/or elimination of device removals and/or replacements, which may be needed if inflammation cannot be reduced or removed.

The device 100 can be self-expandable to keep the capsule open. The device 100 can comprise at least three different planes. For example, a first plane can correspond with the posterior opening or end of the device, where an IOL can be attached. A second plane can correspond with the anterior opening or end of the device, where another refractive surface or IOL can be attached. In some embodiments, device 100 comprises a symmetrical device such that the anterior opening and posterior opening are determined by the device 100 position in the eye. A third plane can be positioned in between the posterior end and the anterior end, for example, along a ridge formed in the central portion, where another an IOL can be attached. In some embodiments, the central portion may comprise a continuous lateral portion interposed between the anterior portion and the posterior portion. In some embodiments, the continuous lateral portion protrudes radially beyond the anterior portion and the posterior portion. In some embodiments, the continuous lateral portion fully encloses a lateral side of the housing structure, wherein an internal cavity of the continuous lateral portion forms a groove for containing an IOL. In some embodiments, the central portion may comprise continuous lateral portion comprising an exterior surface comprising a rounded bulge, the rounded bulge extending radially beyond the anterior portion and the posterior portion. In some embodiments, the continuous lateral portion comprises an interior surface comprising a groove or ridge, wherein at least a portion of the interior surface is formed at an acute angle or an obtuse angle relative to the anterior portion and the posterior portion.

In some embodiments, the prosthetic capsular devices comprise one or more orientation designation indicators or mechanisms 118 configured to serve as a marker to indicate the direction and/or orientation of the prosthetic device before, during, and/or after insertion into the eye. In some embodiments, the one or more orientation designation mechanisms 118 may be located on the anterior side, the posterior side, and/or on the interior and/or exterior sidewalls of the prosthetic capsular device. In some embodiments, the one or more orientation designation mechanisms 118 may assist and/or allow a surgeon or medical professional to determine or perceive if the prosthetic capsular device is oriented correctly before, during, and/or after insertion into the eye.

In some embodiments, the one or more orientation indicators may comprise visual distinguishing factors on the anterior side, the posterior side, and/or on the interior and/or exterior sidewalls of the prosthetic capsular device. For example, the anterior side, the posterior side, and/or the interior and/or exterior sidewalls may differ based on varying structural features, axis marks, colors, shapes, textures, tones, shades, brightness, outlines, sizes, text indicators, engravings, and icons, among others. In some embodiments, the one or more orientation designation indicators facilitate the current orientation of the prosthetic capsular device before, during, and after insertion into the eye and serve as measurement tools to measure, for example, rotational stability.

In some embodiments, the one or more orientation designation indicators comprise a protuberance, nub, protrusion, projection, bulge, or other structure extending from a surface of the housing 100. In some embodiments, the one or more orientation designation indicators comprise a visual marker such as a hole or aperture. In some embodiments, the visual marker may serve as a reference point to measure to rotational stability and position of the prosthetic capsular device 100 before, during, and/or after insertion into the eye. In some embodiments, the one or more orientation designation indicators 118 may extend radially inward from the diameter 104 of the anterior opening and/or the posterior opening. However, in some embodiments, the one or more orientation designation indicators may extend radially inward or radially outward from any structure of the prosthetic device 100 and/or an IOL coupled to the device. In some embodiments, it may be preferable for the one or more orientation designation indicators to extend radially inwardly from the anterior opening to provide optimal visibility to a surgeon and/or medical professional and to avoid unnatural exterior protrusions into the natural capsular bag.

In some embodiments, the prosthetic capsular device 100 may comprise about 2 orientation designation indicators. In some embodiments, the number of orientation designation indicators 118 may be about 1, 2, 3, 4, 5, 6, 7, 8, 9, 10, 11, 12, 13, 14, 15, 20, 25, 30, 35, 40, 45, 50, 100, and/or within a range defined by two of the aforementioned values. An example orientation designation indicator 118 is illustrated in Detail D of FIG. 1. In some embodiments, the orientation designation indicator 118 may comprise a thickness of about 0.10 mm. In some embodiments the orientation designation indicator 118 may comprise a thickness of between about 0.01 mm and 0.30 mm.

In some embodiments, a prosthetic capsular device configured to be inserted in a natural capsular bag of an eye after removal of a lens can comprise a housing structure 100 capable of containing one or more intraocular devices and/or refractive surfaces. In particular, the housing structure can comprise an anterior side, wherein the anterior side comprises an anterior opening that can be elliptical, circular, arcuate, triangular, rectangular, polygonal, or otherwise shaped as shown in the provided Figures, wherein the anterior opening is capable of allowing at least one of insertion, removal, or replacement of an intraocular lens device, and wherein the anterior opening is further configured to be coupled to a lens to cover the anterior opening; a posterior side, wherein the posterior side comprises an posterior opening that can be elliptical, circular, arcuate, triangular, rectangular, polygonal, or otherwise shaped as shown in the provided Figures, wherein the posterior opening is capable of allowing at least one of insertion, removal, or replacement of an intraocular lens or device, and wherein the posterior opening is further configured to be coupled to an intraocular lens or device to cover the posterior opening; and a continuous lateral portion interposed between the anterior portion and the posterior portion, wherein the continuous lateral portion protrudes radially beyond the anterior portion and the posterior portion, wherein the continuous lateral portion fully encloses a lateral side of the housing structure, wherein an internal cavity of the continuous lateral portion forms a groove or ridge for containing an intraocular lens or device within, for example, an anterior portion of the device. The continuous lateral portion may not have any openings, for example along the lateral portion of the device in some embodiments. The housing structure 100 can be symmetrical over a plane at a midpoint of the continuous lateral portion between the anterior portion and the posterior portion.

In some embodiments, the ridge or groove may comprise one or more ribs 105. The ribs 105 are shown in detail along the ridge as Detail C in FIG. 1. In some embodiments, the ribs may be configured to hold an intraocular lens within device 100. For example, the ribs 105 may be configured to reduce mobility of an intraocular lens within device 100, such that lens tilt, lens rotation, and/or decentration is reduced or eliminated. In some embodiments, the ribs 105 may comprise a top surface and a bottom surface with a rib angle 120 between the top and bottom surface. In some embodiments, the rib angle may comprise about 100°. In some embodiments, the rib angle may comprise about 10° to about 180°. For example, in some embodiments, the rib angle may be about 10°, about 15°, about 20°, about 25°, about 30°, about 35°, about 40°, about 45°, about 50°, about 55°, about 60°, about 65°, about 70°, about 75°, about 80°, about 85°, about 90°, about 95°, about 100°, about 105°, about 110°, about 115°, about 120°, about 125°, about 130°, about 135°, about 140°, about 145°, about 150°, about 155°, about 160°, about 165°, about 170°, about 175°, about 180°, or any value between the aforementioned values. In some embodiments, the rib angle 105 may be determined based on the thickness 108 of the device 100, along with the diameter 102.

In some embodiments, the device 100 may comprise about 12 ribs. In some embodiments, the device 100 may comprise between about 1 rib and 100 ribs. about 1 ribs, about 2 ribs, about 3 ribs, about 4 ribs, about 5 ribs, about 6 ribs, about 7 ribs, about 8 ribs, about 9 ribs, about 10 ribs, about 11 ribs, about 12 ribs, about 13 ribs, about 14 ribs, about 15 ribs, about 16 ribs, about 17 ribs, about 18 ribs, about 19 ribs, about 20 ribs, about 21 ribs, about 22 ribs, about 23 ribs, about 24 ribs, about 25 ribs, about 26 ribs, about 27 ribs, about 28 ribs, about 29 ribs, about 30 ribs, about 31 ribs, about 32 ribs, about 33 ribs, about 34 ribs, about 35 ribs, about 36 ribs, about 37 ribs, about 38 ribs, about 39 ribs, about 40 ribs, about 41 ribs, about 42 ribs, about 43 ribs, about 44 ribs, about 45 ribs, about 46 ribs, about 47 ribs, about 48 ribs, about 49 ribs, about 50 ribs, about 51 ribs, about 52 ribs, about 53 ribs, about 54 ribs, about 55 ribs, about 56 ribs, about 57 ribs, about 58 ribs, about 59 ribs, about 60 ribs, about 61 ribs, about 62 ribs, about 63 ribs, about 64 ribs, about 65 ribs, about 66 ribs, about 67 ribs, about 68 ribs, about 69 ribs, about 70 ribs, about 71 ribs, about 72 ribs, about 73 ribs, about 74 ribs, about 75 ribs, about 76 ribs, about 77 ribs, about 78 ribs, about 79 ribs, about 80 ribs, about 81 ribs, about 82 ribs, about 83 ribs, about 84 ribs, about 85 ribs, about 86 ribs, about 87 ribs, about 88 ribs, about 89 ribs, about 90 ribs, about 91 ribs, about 92 ribs, about 93 ribs, about 94 ribs, about 95 ribs, about 96 ribs, about 97 ribs, about 98 ribs, about 99 ribs, or about 100 ribs.

In some embodiments, a thickness 108 of the device may comprise a maximum distance between the anterior side and posterior side of the device 100. In some embodiments, the thickness 108 of the device 100 may be about 2.00 mm. In some embodiments, the thickness 108 of the device 100 may be about 1.50 mm. In some embodiments, the thickness 108 of the device 100 may be between about 0.5 mm and 4.0 mm. In some embodiments, the thickness 108 of the device 100 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the device 100 may comprise a ridge thickness 112 comprising the size of the ridge locating ribs 105. In some embodiments, the ridge thickness 112 may be about 0.40 mm. In some embodiments, the ridge thickness 112 may between about 0.10 mm and about 1.00 mm. In some embodiments, the ridge thickness may be configured to reduce the possibility of lens tilt by an intraocular lens located in the ridge and secured by ribs 105.

In some embodiments, the device 100 may comprise an inner thickness 110 comprising a distance between an inner surface of the sidewall at the anterior opening and an inner surface of the sidewall at the posterior opening. In some embodiments, the inner thickness 110 may be about 1.48 mm.

In some embodiments, the device 100 may comprise an inner diameter 106 comprising the distance between the interior surfaces of the sidewalls at the ridge. In some embodiments, the inner diameter 106 may about 9.15 mm. In some embodiments, the interior diameter may be between about 5.00 mm and 15.00 mm.

In some embodiments, the sidewall at the anterior portion of the device 100 and the sidewall at the posterior of the device 100 may form a sidewall angle 124, formed at the ridge of the device 100. In some embodiments, the sidewall angle 124 may about 34°. In some embodiments, the sidewall angle 124 may about 57°. In some embodiments, the sidewall angle 124 may be about 10° to about 180°. For example, in some embodiments, the sidewall angle 124 may be about 10°, about 15°, about 20°, about 25°, about 30°, about 35°, about 40°, about 45°, about 50°, about 55°, about 60°, about 65°, about 70°, about 75°, about 80°, about 85°, about 90°, about 95°, about 100°, about 105°, about 110°, about 115°, about 120°, about 125°, about 130°, about 135°, about 140°, about 145°, about 150°, about 155°, about 160°, about 165°, about 170°, about 175°, about 180°, or any value between the aforementioned values. In some embodiments, the sidewall angle 124 may be determined based on the thickness 108 of the device 100, along with the diameter 102.

In some embodiments, the cavity of the device may comprise a volume for maintaining the shape and size of the natural capsular bag. The volume may be formed by the angled sidewalls and may comprise a tapered confinement area, wherein the sidewall taper into the cavity at the anterior and posterior openings. In some embodiments, the taper may form a curve in the sidewall adjacent to the anterior and posterior openings. The curved section of the sidewall may provide a smoothed edge to reduce the impact of incidental contact with the posterior surface of the iris of the eye, or pressure transduced through the natural capsular bag and imparted onto the posterior surface of the iris of the eye. In some embodiments, the taper length 114 may comprise a distance between the exterior surface of the sidewall at its most anterior/posterior point and the exterior surface at the anterior/posterior opening. In some embodiments, the exterior surface may comprise curved surfaces 122 and 116 at the ridge and at the openings, respectively. The curved shape of the sidewalls may contribute to a reduction in post-surgical complications through minimization of contact or the severity of contact between the device 100 and the iris. The curved shape of the sidewall of the device 100 near the openings is shown in Detail B.

FIGS. 3-30 illustrate other example prosthetic capsular devices according to some embodiments herein. The embodiments of FIGS. 2-30 may comprise some or all of the features of devices described in U.S. Pat. No. 10,603,162 and of device 100. In addition, the embodiments of FIGS. 2-30 may comprise one or more additional features.

Figure 3:
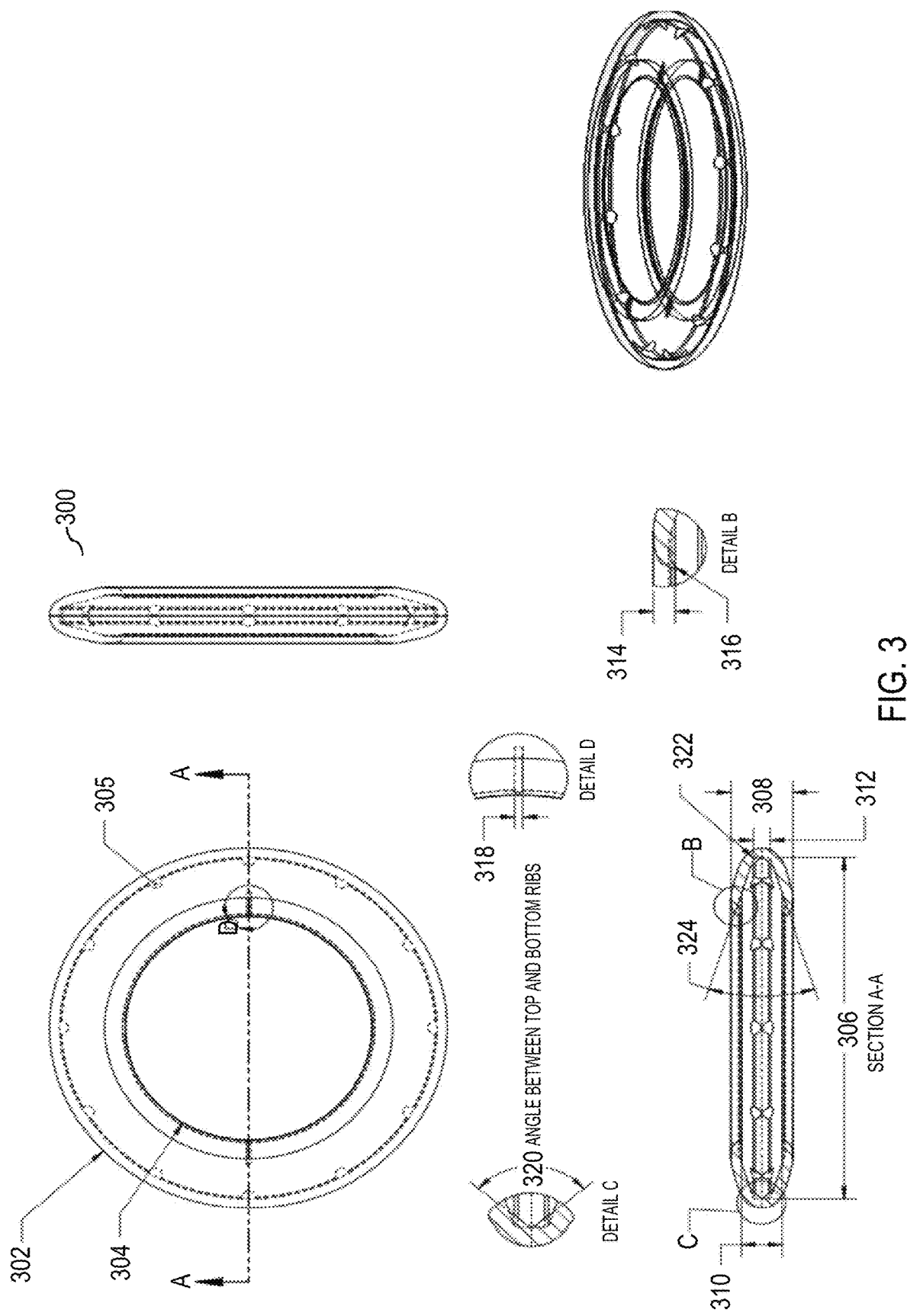
FIG. 3 illustrates another example prosthetic capsular device according to some embodiments herein.
Figure 4:
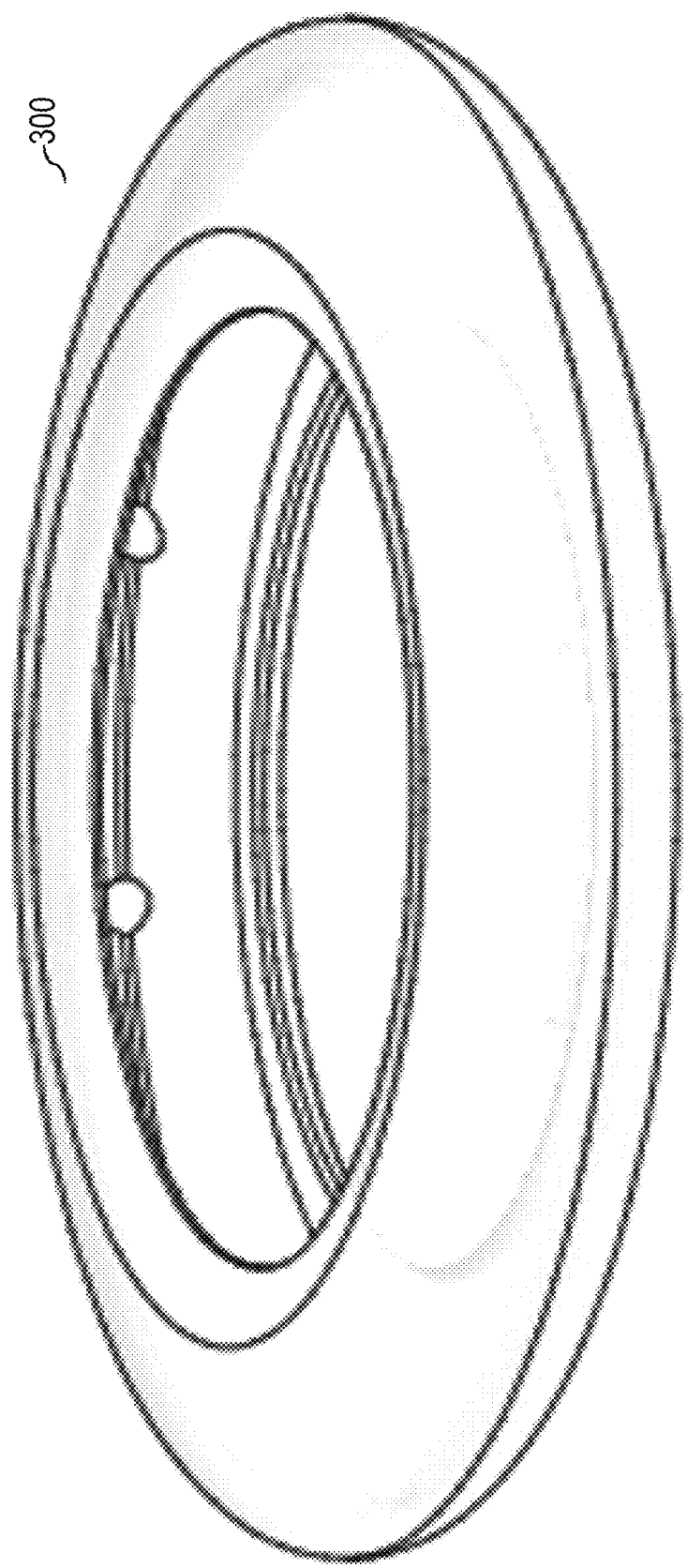
FIG. 4 is an anterior side perspective view of the example prosthetic capsular device of FIG. 3.

FIG. 3 illustrates another example prosthetic capsular device according to some embodiments herein. FIG. 4 is an anterior side perspective view of the example prosthetic capsular device of FIG. 3. In device 300 of FIGS. 3-4, the sidewall at the anterior portion of the device 300 and the sidewall at the posterior of the device 300 may form a sidewall angle 324, formed at the ridge of the device 300. In some embodiments, the sidewall angle 324 may be smaller than that of device 100. In some embodiments, this smaller sidewall angle may reduce the overall thickness and profile of the device 300 relative to device 100. As such, device 300 may be smaller and be used where a smaller profile is necessary depending on the needs of a patient.

In some embodiments, a length of a major axis of the device 300 or a length measured from the outermost end of one sidewall to the outermost end of another sidewall along a major axis of the device 300 can be about 9.65 mm. In other embodiments, the length of the major axis of the device 300 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 300 may comprise a diameter 302 of the device 300.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 304, which can be a diameter of an anterior opening and/or a posterior opening.

In some embodiments, the device 300 may comprise a ridge or groove comprising one or more ribs 305. The ribs 305 are shown in detail along the ridge as Detail C in FIG. 3. In some embodiments, the ribs may be configured to hold an intraocular lens within device 300. For example, the ribs 305 may be configured to reduce mobility of an intraocular lens within device 300, such that lens tilt, lens rotation, and/or decentration is reduced or eliminated. In some embodiments, the ribs 305 may comprise a top surface and a bottom surface with a rib angle 320 between the top and bottom surface. In some embodiments, the rib angle may comprise about 100°. In some embodiments, the rib angle may comprise about 10° to about 180°. For example, in some embodiments, the rib angle may be about 10°, about 15°, about 20°, about 25°, about 30°, about 35°, about 40°, about 45°, about 50°, about 55°, about 60°, about 65°, about 70°, about 75°, about 80°, about 85°, about 90°, about 95°, about 100°, about 105°, about 110°, about 115°, about 120°, about 125°, about 130°, about 135°, about 140°, about 145°, about 150°, about 155°, about 160°, about 165°, about 170°, about 175°, about 180°, or any value between the aforementioned values. In some embodiments, the rib angle 305 may be determined based on the thickness 308 of the device 300, along with the diameter 302.

In some embodiments, a thickness 308 of the device 300 may comprise a maximum distance between the anterior side and posterior side of the device 300. In some embodiments, the thickness 308 of the device 308 may be about 2.00 mm. In some embodiments, the thickness 308 of the device 300 may be about 1.50 mm. In some embodiments, the thickness 308 of the device 300 may be between about 0.5 mm and 4.0 mm. In some embodiments, the thickness 308 of the device may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the prosthetic capsular device 300 comprises one or more orientation designation indicators or mechanisms 318 configured to serve as a marker to indicate the direction and/or orientation of the prosthetic device before, during, and/or after insertion into the eye. In some embodiments, the one or more orientation designation mechanisms 318 may be located on the anterior side, the posterior side, and/or on the interior and/or exterior sidewalls of the prosthetic capsular device. In some embodiments, the one or more orientation designation mechanisms 318 may assist and/or allow a surgeon or medical professional to determine or perceive if the prosthetic capsular device is oriented correctly before, during, and/or after insertion into the eye. The orientation designation indicators or mechanisms 318 may comprise similar or identical features as those discussed in relation to orientation designation indicators or mechanisms 118 of FIG. 1.

In some embodiments, the device 300 may comprise an inner thickness 310 comprising a distance between an inner surface of the sidewall at the anterior opening and an inner surface of the sidewall at the posterior opening. In some embodiments, the inner thickness 310 may be about 0.98 mm.

In some embodiments, the taper length 314 may comprise a distance between the exterior surface of the sidewall at its most anterior/posterior point and the exterior surface at the anterior/posterior opening. In some embodiments, the exterior surface may comprise curved surfaces 322 and 316 at the ridge and at the openings, respectively. The curved shape of the sidewalls may contribute to a reduction in post-surgical complications through minimization of contact or the severity of contact between the device 300 and the iris. The curved shape of the sidewall of the device 300 near the openings is shown in Detail B.

In some embodiments, the device 300 may comprise an inner diameter 306 comprising the distance between the interior surfaces of the sidewalls at the ridge. In some embodiments, the inner diameter 306 may about 9.15 mm. In some embodiments, the interior diameter may be between about 5.00 mm and 15.00 mm.

In some embodiments, the device 300 may comprise a ridge thickness 312 comprising the size of the ridge locating ribs 305. In some embodiments, the ridge thickness 312 may be about 0.40 mm. In some embodiments, the ridge thickness 312 may between about 0.10 mm and about 1.00 mm. In some embodiments, the ridge thickness may be configured to reduce the possibility of lens tilt by an intraocular lens located in the ridge and secured by ribs 305.

Figure 5:
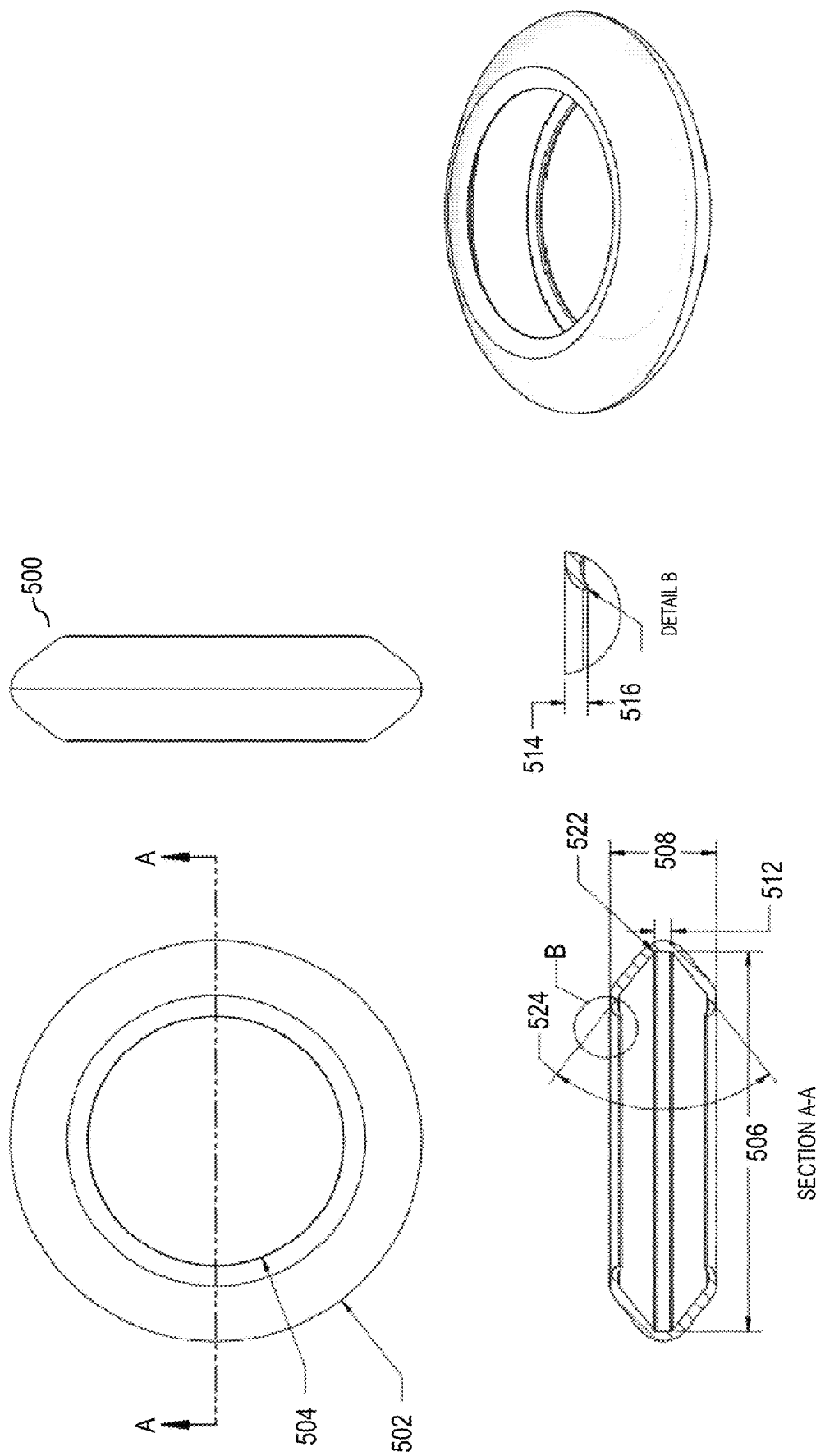
FIG. 5 illustrates another example prosthetic capsular device according to some embodiments herein.

FIG. 5 illustrates another example prosthetic capsular device according to some embodiments herein. In device 500 of FIG. 5, the sidewall at the anterior portion of the device 500 and the sidewall at the posterior of the device 500 may form a sidewall angle 524, formed at a slot of the device 500. In some embodiments, the sidewall angle 524 may be larger than that of device 100 and device 300. For example, the sidewall angle may be about 75° or even larger. Furthermore, device 500 may not comprise any ribs, such as ribs 105 or ribs 305. Instead, device 500 may comprise a slot within the device cavity configured to secure an intraocular lens therein.

In some embodiments, a length of a major axis of the device 500 or a length measured from the outermost end of one sidewall to the outermost end of another sidewall along a major axis of the device 500 can be about 9.65 mm. In other embodiments, the length of the major axis of the device 500 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 500 may comprise a diameter 502 of the device 500.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 504, which can be a diameter of an anterior opening and/or a posterior opening.

In some embodiments, the taper length 514 may comprise a distance between the exterior surface of the sidewall at its most anterior/posterior point and the exterior surface at the anterior/posterior opening. In some embodiments, the exterior surface may comprise curved surfaces 522 and 516 at the slot and at the openings, respectively. The curved shape of the sidewalls may contribute to a reduction in post-surgical complications through minimization of contact or the severity of contact between the device 500 and the iris. The curved shape of the sidewall of the device 500 near the openings is shown in Detail B.

In some embodiments, the device 500 may comprise an inner diameter 506 comprising the distance between the interior surfaces of the sidewalls at the ridge. In some embodiments, the inner diameter 506 may about 9.15 mm. In some embodiments, the interior diameter may be between about 5.00 mm and 15.00 mm.

In some embodiments, the device 500 may comprise a slot thickness 512 comprising the size of the slot. In some embodiments, the slot thickness 512 may be about 0.40 mm. In some embodiments, the slot thickness 512 may between about 0.10 mm and about 1.00 mm. In some embodiments, the slot thickness may be configured to reduce the possibility of lens tilt by an intraocular lens located in the slot.

In some embodiments, a thickness 508 of the device 500 may comprise a maximum distance between the anterior side and posterior side of the device 500. In some embodiments, the thickness 508 of the device 308 may be about 2.50 mm. In some embodiments, the thickness 508 of the device 500 may be between about 0.5 mm and 4.0 mm. In some embodiments, the thickness 508 of the device may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 6:
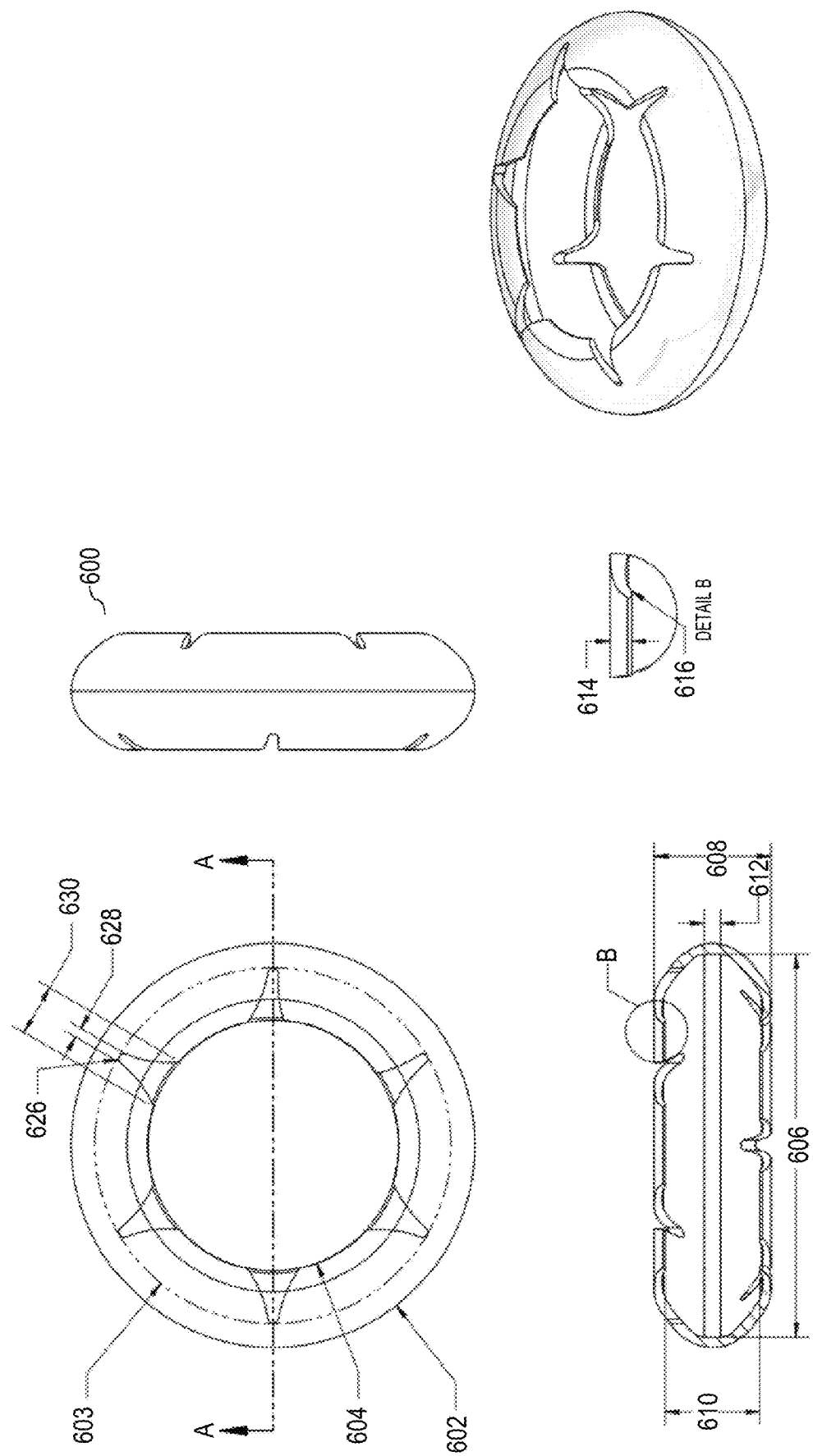
FIG. 6 illustrates another example prosthetic capsular device according to some embodiments herein.

FIG. 6 illustrates another example prosthetic capsular device according to some embodiments herein. In device 600 of FIG. 6, the sidewall at the anterior portion of the device 600 and the sidewall at the posterior of the device 600 may comprise one or more cutouts 626, opening the anterior portion and the posterior portion of the device 600 to the interior cavity. In some embodiments, there may be 6 cutouts in the device 600. However, the number and shape of the cutouts is not limited. In some embodiments, the cutouts 626 may facilitate folding and expansion of the device or may allow for insertion of differently shaped or sized intraocular lenses.

In some embodiments, the cutouts may be substantially triangular with a rounded or blunted tip, wherein the tip comprises a width 628. In some embodiments, the tip may comprise a width 628 of about 0.25 mm. In some embodiments, the tip may comprise a width 628 of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, and/or within a range defined by two of the aforementioned values. In some embodiments, the base of the cutouts may comprise a base width 630 of about 1.25 mm. In some embodiments, the base width 630 may range from about 0.1 mm to about 3.00 mm. In some embodiments, the tip may comprise one or more rounded corners having a radius of about 0.13 mm. In some embodiments, the diameter 603 of the cutouts 626, measured at the tips of the cutouts, may be about 8.5 mm.

In some embodiments, a length of a major axis of the device 600 or a length measured from the outermost end of one sidewall to the outermost end of another sidewall along a major axis of the device 600 can be about 9.65 mm. In other embodiments, the length of the major axis of the device 600 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 600 may comprise a diameter 602 of the device 600.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 604, which can be a diameter of an anterior opening and/or a posterior opening.

In some embodiments, the device 600 may comprise an inner thickness 610 comprising a distance between an inner surface of the sidewall at the anterior opening and an inner surface of the sidewall at the posterior opening. In some embodiments, the inner thickness 610 may be about 2.27 mm.

In some embodiments, the taper length 614 may comprise a distance between the exterior surface of the sidewall at its most anterior/posterior point and the exterior surface at the anterior/posterior opening. In some embodiments, the exterior surface may comprise curved surface 616 at the openings. The curved shape of the sidewalls may contribute to a reduction in post-surgical complications through minimization of contact or the severity of contact between the device 600 and the iris. The curved shape of the sidewall of the device 600 near the openings is shown in Detail B.

In some embodiments, the device 600 may comprise an inner diameter 606 comprising the distance between the interior surfaces of the sidewalls at the ridge. In some embodiments, the inner diameter 606 may about 9.15 mm. In some embodiments, the interior diameter may be between about 5.00 mm and 15.00 mm.

In some embodiments, the device 600 may comprise a slot thickness 612 comprising the size of the slot. In some embodiments, the slot thickness 612 may be about 0.40 mm. In some embodiments, the slot thickness 612 may between about 0.10 mm and about 1.00 mm. In some embodiments, the slot thickness may be configured to reduce the possibility of lens tilt by an intraocular lens located in the slot.

In some embodiments, a thickness 608 of the device 600 may comprise a maximum distance between the anterior side and posterior side of the device 600. In some embodiments, the thickness 608 of the device 600 may be about 2.80 mm. In some embodiments, the thickness 608 of the device 600 may be between about 0.5 mm and 4.0 mm. In some embodiments, the thickness 608 of the device 600 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the device 600 may comprise an inner thickness 610 comprising a distance between an inner surface of the sidewall at the anterior opening and an inner surface of the sidewall at the posterior opening. In some embodiments, the inner thickness 610 may be about 2.27 mm.

Figure 7:
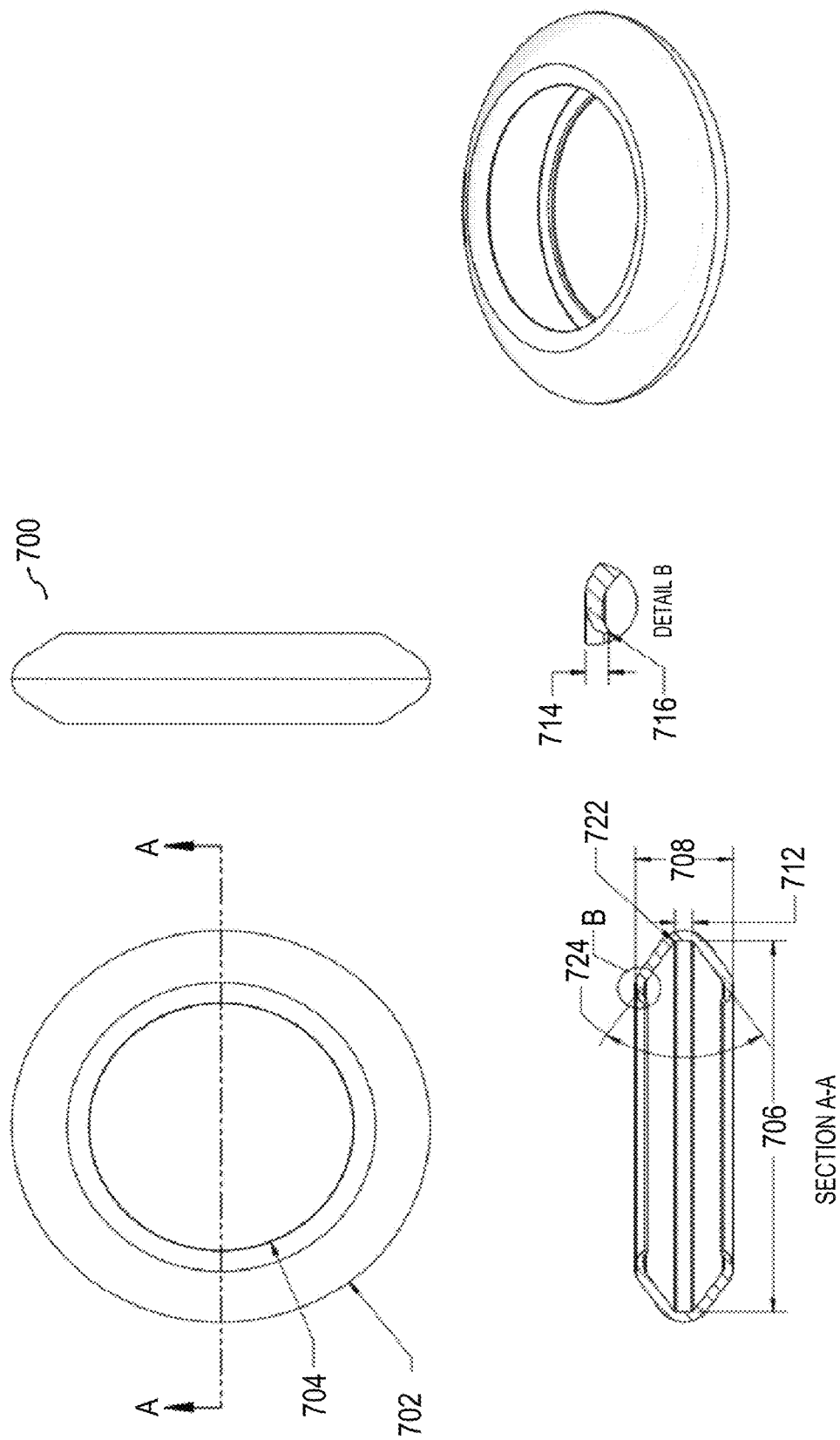
FIG. 7 illustrates another example prosthetic capsular device according to some embodiments herein.

FIG. 7 illustrates another example prosthetic capsular device according to some embodiments herein. In device 700 of FIG. 7, the sidewall at the anterior portion of the device 700 and the sidewall at the posterior of the device 700 may form a sidewall angle 724, formed at a slot of the device 700. In some embodiments, the sidewall angle 724 may be larger than that of device 100 and device 300. For example, the sidewall angle may be about 69° or even larger. Furthermore, device 700 may not comprise any ribs, such as ribs 105 or ribs 305. Instead, device 700 may comprise a slot within the device cavity configured to secure an intraocular lens therein.

In some embodiments, a length of a major axis of the device 700 or a length measured from the outermost end of one sidewall to the outermost end of another sidewall along a major axis of the device 700 can be about 9.65 mm. In other embodiments, the length of the major axis of the device 700 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 700 may comprise a diameter 702 of the device 700.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 704, which can be a diameter of an anterior opening and/or a posterior opening.

In some embodiments, the taper length 714 may comprise a distance between the exterior surface of the sidewall at its most anterior/posterior point and the exterior surface at the anterior/posterior opening. In some embodiments, the exterior surface may comprise curved surfaces 722 and 716 at the slot and at the openings, respectively. The curved shape of the sidewalls may contribute to a reduction in post-surgical complications through minimization of contact or the severity of contact between the device 700 and the iris. The curved shape of the sidewall of the device 700 near the openings is shown in Detail B.

In some embodiments, the device 700 may comprise an inner diameter 706 comprising the distance between the interior surfaces of the sidewalls at the ridge. In some embodiments, the inner diameter 706 may about 9.15 mm. In some embodiments, the interior diameter may be between about 5.00 mm and 15.00 mm.

In some embodiments, the device 700 may comprise a slot thickness 712 comprising the size of the slot. In some embodiments, the slot thickness 712 may be about 0.40 mm. In some embodiments, the slot thickness 712 may between about 0.10 mm and about 1.00 mm. In some embodiments, the slot thickness may be configured to reduce the possibility of lens tilt by an intraocular lens located in the slot.

In some embodiments, a thickness 708 of the device 700 may comprise a maximum distance between the anterior side and posterior side of the device 700. In some embodiments, the thickness 708 of the device 700 may be about 2.21 mm. In some embodiments, the thickness 708 of the device 700 may be between about 0.5 mm and 4.0 mm. In some embodiments, the thickness 708 of the device 700 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the device 700 may comprise an inner thickness 710 comprising a distance between an inner surface of the sidewall at the anterior opening and an inner surface of the sidewall at the posterior opening. In some embodiments, the inner thickness 710 may be about 2.27 mm.

Figure 8:
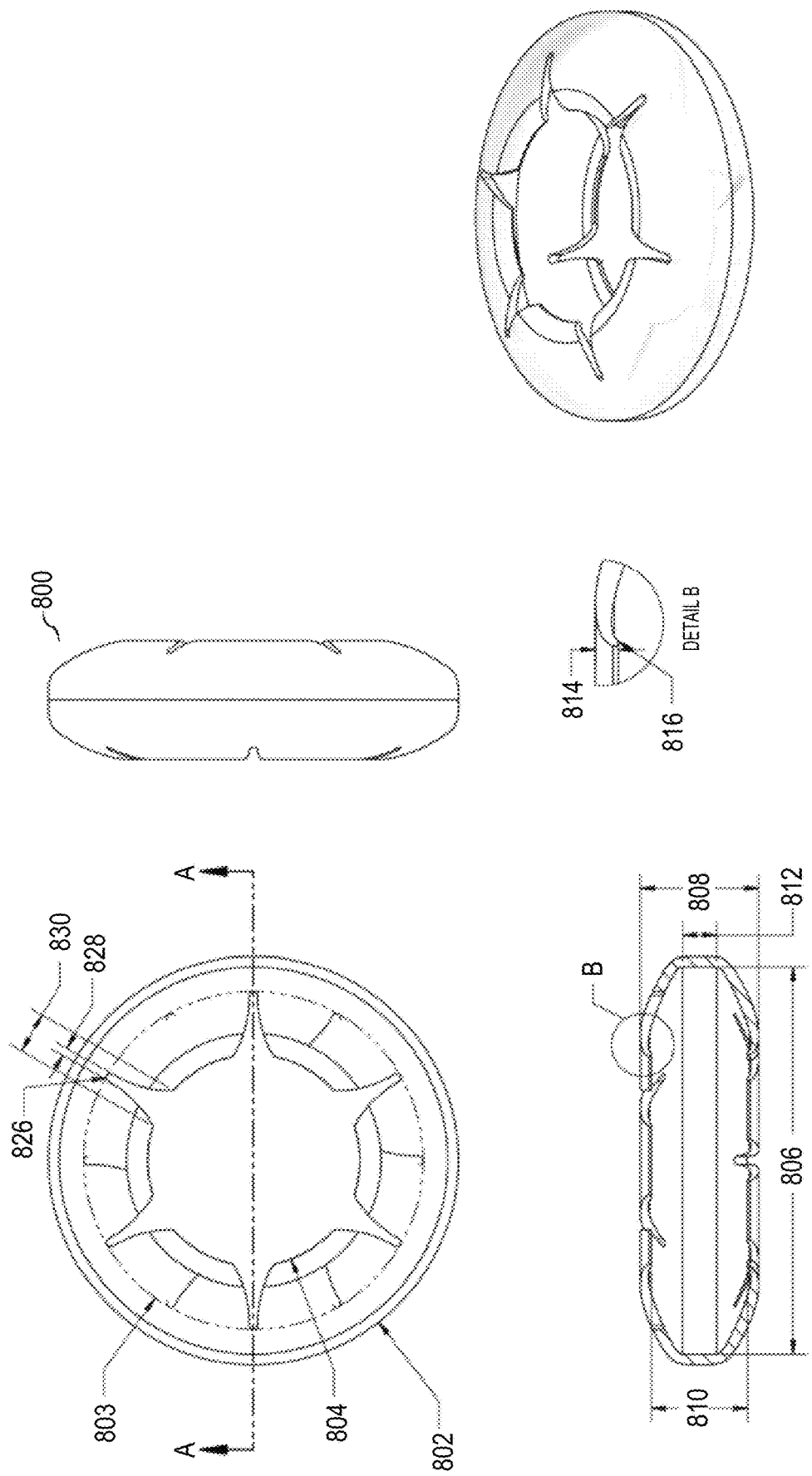
FIG. 8 illustrates another example prosthetic capsular device according to some embodiments herein.

FIG. 8 illustrates another example prosthetic capsular device according to some embodiments herein. In device 800 of FIG. 8, the sidewall at the anterior portion of the device 800 and the sidewall at the posterior of the device 800 may comprise one or more cutouts 826, opening the anterior portion and the posterior portion of the device 800 to the interior cavity. In some embodiments, there may be 6 cutouts in the device 800. However, the number and shape of the cutouts is not limited. In some embodiments, the cutouts 826 may facilitate folding and expansion of the device or may allow for insertion of differently shaped or sized intraocular lenses.

In some embodiments, the cutouts may be substantially triangular with a rounded or blunted tip, wherein the tip comprises a width 828. In some embodiments, the tip may comprise a width 828 of about 0.19 mm. In some embodiments, the tip may comprise a width 828 of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, and/or within a range defined by two of the aforementioned values. In some embodiments, the base of the cutouts may comprise a base width 830 of about 0.98 mm. In some embodiments, the base width 830 may range from about 0.1 mm to about 3.00 mm. In some embodiments, the tip may comprise one or more rounded corners having a radius of about 0.10 mm. In some embodiments, the diameter 803 of the cutouts 826, measured at the tips of the cutouts, may be about 8.00 mm.

In some embodiments, a length of a major axis of the device 800 or a length measured from the outermost end of one sidewall to the outermost end of another sidewall along a major axis of the device 800 can be about 9.65 mm. In other embodiments, the length of the major axis of the device 800 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 800 may comprise a diameter 802 of the device 800.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 804, which can be a diameter of an anterior opening and/or a posterior opening.

In some embodiments, the device 800 may comprise an inner thickness 810 comprising a distance between an inner surface of the sidewall at the anterior opening and an inner surface of the sidewall at the posterior opening. In some embodiments, the inner thickness 810 may be about 2.27 mm.

In some embodiments, the taper length 814 may comprise a distance between the exterior surface of the sidewall at its most anterior/posterior point and the exterior surface at the anterior/posterior opening. In some embodiments, the exterior surface may comprise curved surfaces 816 at the openings. The curved shape of the sidewalls may contribute to a reduction in post-surgical complications through minimization of contact or the severity of contact between the device 800 and the iris. The curved shape of the sidewall of the device 800 near the openings is shown in Detail B.

In some embodiments, the device 800 may comprise an inner diameter 806 comprising the distance between the interior surfaces of the sidewalls at the ridge. In some embodiments, the inner diameter 806 may about 9.15 mm. In some embodiments, the interior diameter may be between about 5.00 mm and 15.00 mm.

In some embodiments, the device 800 may comprise a slot thickness 812 comprising the size of the slot. In some embodiments, the slot thickness 812 may be about 0.80 mm. In some embodiments, the slot thickness 812 may between about 0.10 mm and about 1.00 mm. In some embodiments, the slot thickness may be configured to reduce the possibility of lens tilt by an intraocular lens located in the slot.

In some embodiments, a thickness 808 of the device 800 may comprise a maximum distance between the anterior side and posterior side of the device 800. In some embodiments, the thickness 808 of the device 800 may be about 2.80 mm. In some embodiments, the thickness 808 of the device 800 may be between about 0.5 mm and 4.00 mm. In some embodiments, the thickness 808 of the device 800 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 9:
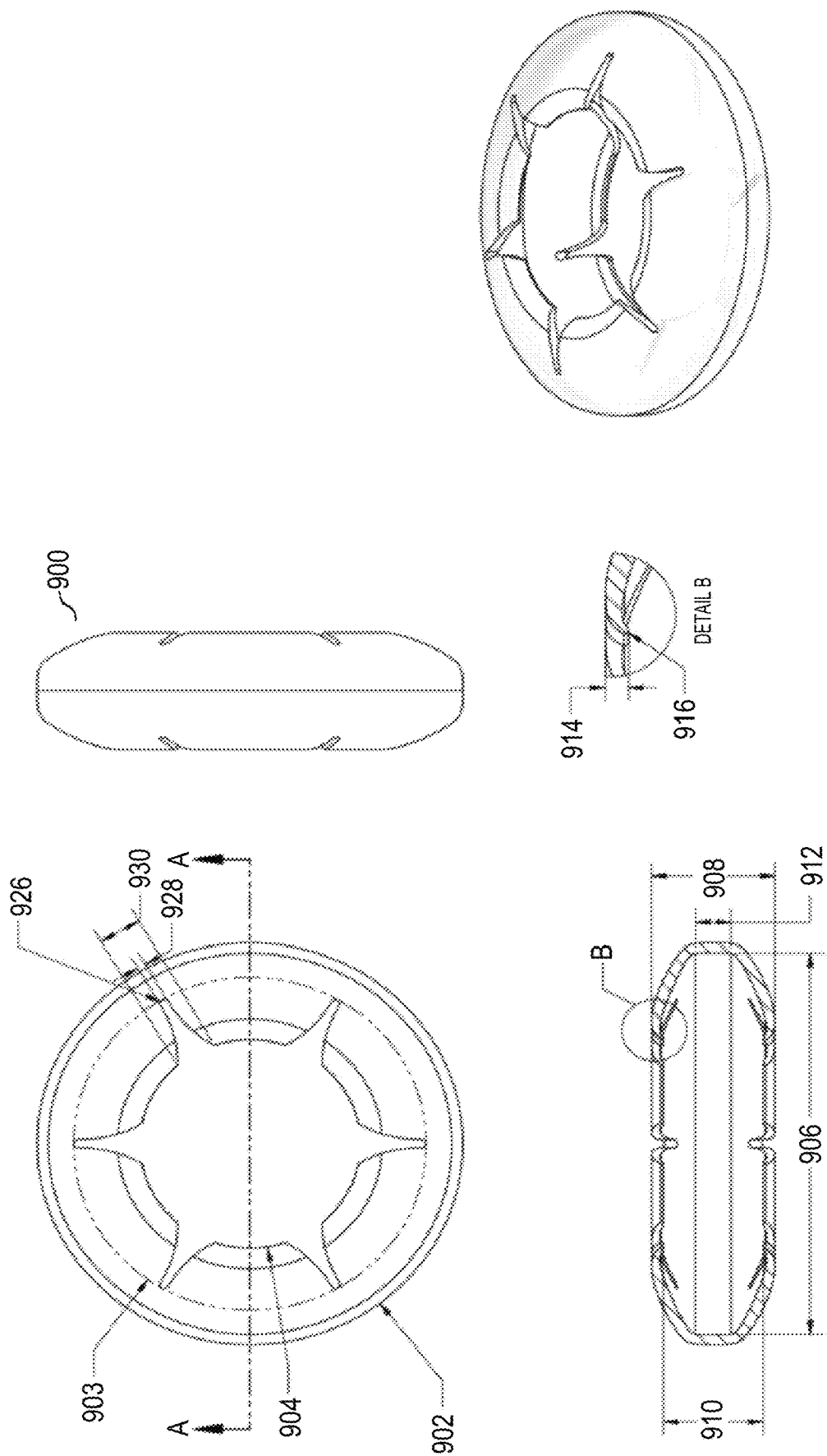
FIG. 9 illustrates another example prosthetic capsular device according to some embodiments herein.

FIG. 9 illustrates another example prosthetic capsular device according to some embodiments herein. In device 900 of FIG. 9, the sidewall at the anterior portion of the device 900 and the sidewall at the posterior of the device 900 may comprise one or more cutouts 926, opening the anterior portion and the posterior portion of the device 900 to the interior cavity. In some embodiments, there may be 6 cutouts in the device 900. However, the number and shape of the cutouts is not limited. In some embodiments, the cutouts 926 may facilitate folding and expansion of the device or may allow for insertion of differently shaped or sized intraocular lenses.

In some embodiments, the cutouts may be substantially triangular with a rounded or blunted tip, wherein the tip comprises a width 928. In some embodiments, the tip may comprise a width 928 of about 0.19 mm. In some embodiments, the tip may comprise a width 928 of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, and/or within a range defined by two of the aforementioned values. In some embodiments, the base of the cutouts may comprise a base width 930 of about 0.98 mm. In some embodiments, the base width 930 may range from about 0.1 mm to about 3.00 mm. In some embodiments, the tip may comprise one or more rounded corners having a radius of about 0.10 mm. In some embodiments, the diameter 903 of the cutouts 926, measured at the tips of the cutouts, may be about 8.00 mm.

In some embodiments, a length of a major axis of the device 900 or a length measured from the outermost end of one sidewall to the outermost end of another sidewall along a major axis of the device 900 can be about 9.65 mm. In other embodiments, the length of the major axis of the device 900 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 900 may comprise a diameter 902 of the device 900.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 904, which can be a diameter of an anterior opening and/or a posterior opening.

In some embodiments, the device 900 may comprise an inner thickness 910 comprising a distance between an inner surface of the sidewall at the anterior opening and an inner surface of the sidewall at the posterior opening. In some embodiments, the inner thickness 910 may be about 2.27 mm.

In some embodiments, the taper length 914 may comprise a distance between the exterior surface of the sidewall at its most anterior/posterior point and the exterior surface at the anterior/posterior opening. In some embodiments, the exterior surface may comprise curved surfaces 916 at the openings. The curved shape of the sidewalls may contribute to a reduction in post-surgical complications through minimization of contact or the severity of contact between the device 900 and the iris. The curved shape of the sidewall of the device 900 near the openings is shown in Detail B.

In some embodiments, the device 900 may comprise an inner diameter 906 comprising the distance between the interior surfaces of the sidewalls at the ridge. In some embodiments, the inner diameter 906 may about 9.15 mm. In some embodiments, the interior diameter may be between about 5.00 mm and 15.00 mm.

In some embodiments, the device 900 may comprise a slot thickness 912 comprising the size of the slot. In some embodiments, the slot thickness 912 may be about 0.80 mm. In some embodiments, the slot thickness 912 may between about 0.10 mm and about 1.00 mm. In some embodiments, the slot thickness may be configured to reduce the possibility of lens tilt by an intraocular lens located in the slot.

In some embodiments, a thickness 908 of the device 900 may comprise a maximum distance between the anterior side and posterior side of the device 900. In some embodiments, the thickness 908 of the device 900 may be about 2.80 mm. In some embodiments, the thickness 908 of the device 900 may be between about 0.5 mm and 4.0 mm. In some embodiments, the thickness 908 of the device 900 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 10:
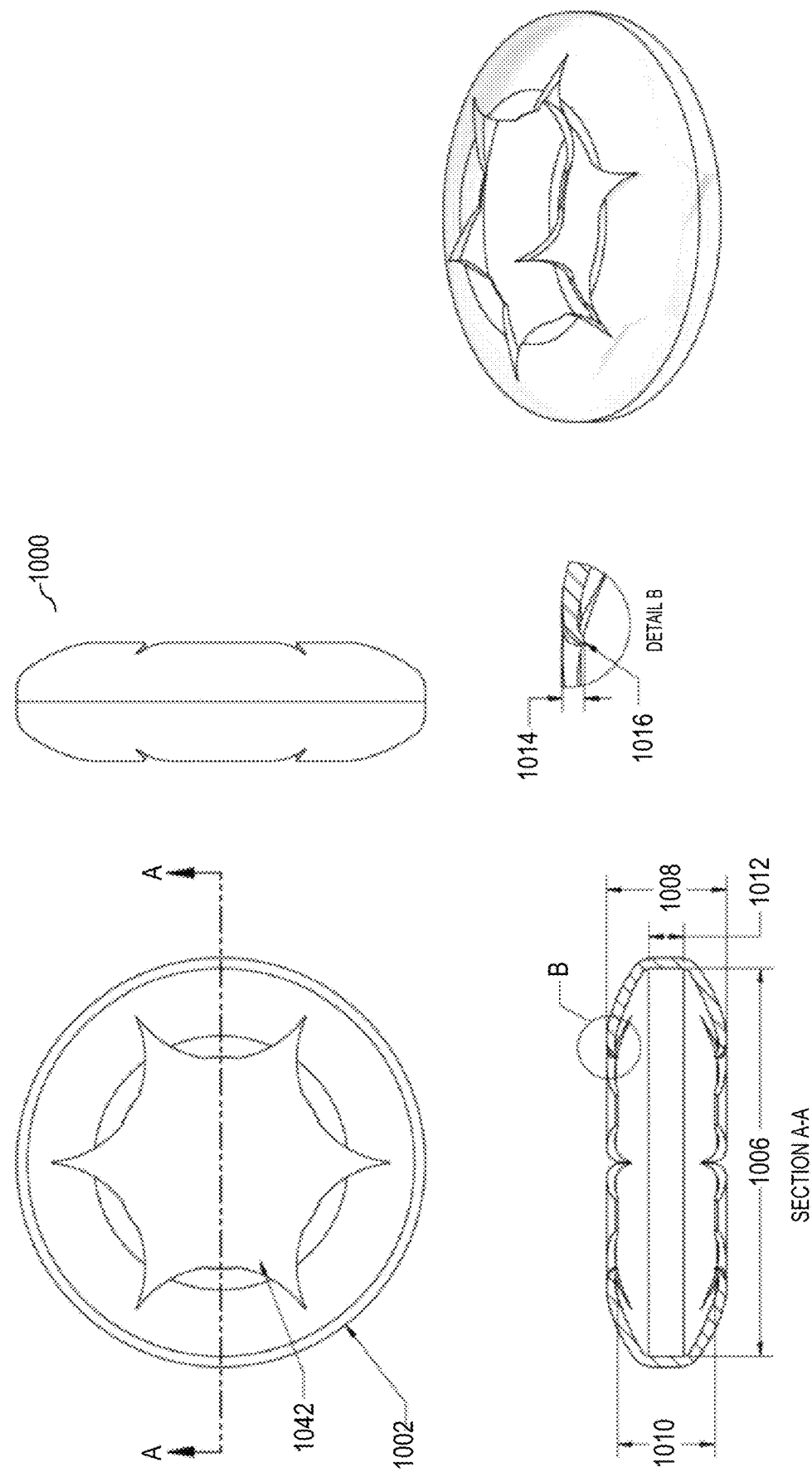
FIG. 10 illustrates another example prosthetic capsular device according to some embodiments herein.

FIG. 10 illustrates another example prosthetic capsular device according to some embodiments herein. In device 1000 of FIG. 10, the sidewall at the anterior portion of the device 1000 and the sidewall at the posterior of the device 1000 may comprise one or more cutouts, opening the anterior portion and the posterior portion of the device 1000 to the interior cavity. In some embodiments, there may be 6 cutouts in the device 1000. However, the number and shape of the cutouts is not limited. In some embodiments, the cutouts may facilitate folding and expansion of the device or may allow for insertion of differently shaped or sized intraocular lenses. In some embodiments, the cutouts may be integrally formed with the anterior opening and the posterior opening forming a pointed star-shaped opening.

In some embodiments, a length of a major axis of the device 1000 or a length measured from the outermost end of one sidewall to the outermost end of another sidewall along a major axis of the device 1000 can be about 9.65 mm. In other embodiments, the length of the major axis of the device 1000 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1000 may comprise a diameter 1002 of the device 1000.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1004, which can be a diameter of an anterior opening and/or a posterior opening.

In some embodiments, the device 1000 may comprise an inner thickness 1010 comprising a distance between an inner surface of the sidewall at the anterior opening and an inner surface of the sidewall at the posterior opening. In some embodiments, the inner thickness 1010 may be about 2.27 mm.

In some embodiments, the taper length 1014 may comprise a distance between the exterior surface of the sidewall at its most anterior/posterior point and the exterior surface at the anterior/posterior opening. In some embodiments, the exterior surface may comprise curved surface 1016 at the openings, respectively. The curved shape of the sidewalls may contribute to a reduction in post-surgical complications through minimization of contact or the severity of contact between the device 1000 and the iris. The curved shape of the sidewall of the device 1000 near the openings is shown in Detail B.

In some embodiments, the device 1000 may comprise an inner diameter 1006 comprising the distance between the interior surfaces of the sidewalls at the ridge. In some embodiments, the inner diameter 1006 may about 9.15 mm. In some embodiments, the interior diameter may be between about 5.00 mm and 15.00 mm.

In some embodiments, the device 1000 may comprise a slot thickness 1012 comprising the size of the slot. In some embodiments, the slot thickness 1012 may be about 0.80 mm. In some embodiments, the slot thickness 1012 may between about 0.10 mm and about 1.00 mm. In some embodiments, the slot thickness may be configured to reduce the possibility of lens tilt by an intraocular lens located in the slot.

In some embodiments, a thickness 1008 of the device 1000 may comprise a maximum distance between the anterior side and posterior side of the device 1000. In some embodiments, the thickness 1008 of the device 1000 may be about 2.80 mm. In some embodiments, the thickness 1008 of the device 1000 may be between about 0.5 mm and 4.0 mm. In some embodiments, the thickness 1008 of the device 1000 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 11:
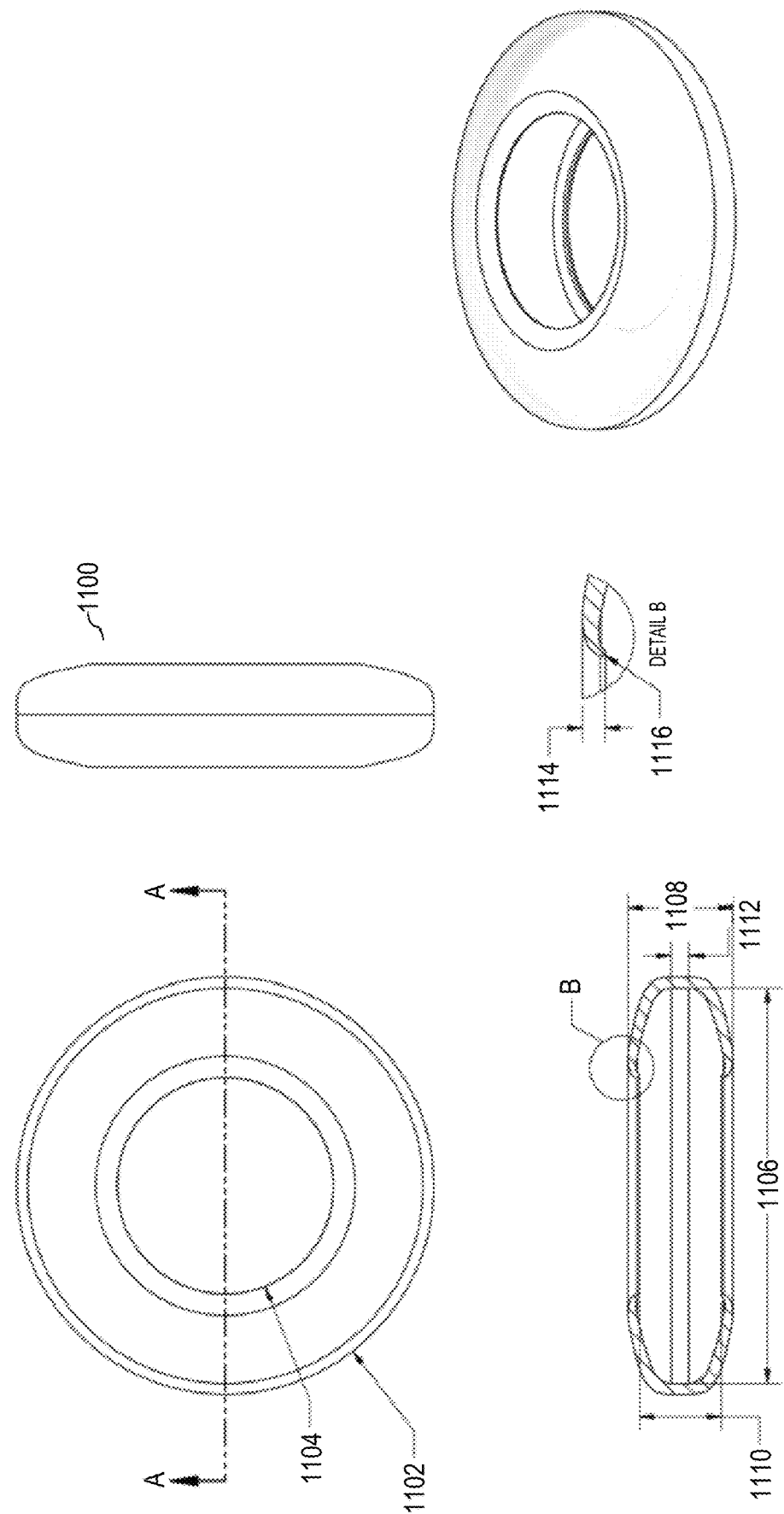
FIG. 11 illustrates another example prosthetic capsular device according to some embodiments herein.

FIG. 11 illustrates another example prosthetic capsular device according to some embodiments herein. In device 1100 of FIG. 11, the sidewall at the anterior portion of the device 1100 and the sidewall at the posterior of the device 1100 may form a slot of the device 1100. In some embodiments, the device 1100 may comprise a cylindrical middle portion perpendicular to the anterior opening and the posterior opening. Device 1100 may comprise a slot within the device cavity configured to secure an intraocular lens therein.

In some embodiments, a length of a major axis of the device 1100 or a length measured from the outermost end of one sidewall to the outermost end of another sidewall along a major axis of the device 1100 can be about 9.65 mm. In other embodiments, the length of the major axis of the device 1100 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1100 may comprise a diameter 1102 of the device 1100.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1104, which can be a diameter of an anterior opening and/or a posterior opening.

In some embodiments, the taper length 1114 may comprise a distance between the exterior surface of the sidewall at its most anterior/posterior point and the exterior surface at the anterior/posterior opening. In some embodiments, the exterior surface may comprise curved surfaces 1116 at the openings. The curved shape of the sidewalls may contribute to a reduction in post-surgical complications through minimization of contact or the severity of contact between the device 1100 and the iris. The curved shape of the sidewall of the device 1100 near the openings is shown in Detail B.

In some embodiments, the device 1100 may comprise an inner diameter 1106 comprising the distance between the interior surfaces of the sidewalls at the ridge. In some embodiments, the inner diameter 1106 may about 9.15 mm. In some embodiments, the interior diameter may be between about 5.00 mm and 15.00 mm.

In some embodiments, the device 1100 may comprise a slot thickness 1112 comprising the size of the slot. In some embodiments, the slot thickness 1112 may be about 0.40 mm. In some embodiments, the slot thickness 1112 may between about 0.10 mm and about 1.00 mm. In some embodiments, the slot thickness may be configured to reduce the possibility of lens tilt by an intraocular lens located in the slot.

In some embodiments, a thickness 1108 of the device 1100 may comprise a maximum distance between the anterior side and posterior side of the device 1100. In some embodiments, the thickness 1108 of the device 1100 may be about 2.40 mm. In some embodiments, the thickness 1108 of the device 1100 may be between about 0.5 mm and 4.0 mm. In some embodiments, the thickness 1108 of the device 1100 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the device 1100 may comprise an inner thickness 1110 comprising a distance between an inner surface of the sidewall at the anterior opening and an inner surface of the sidewall at the posterior opening. In some embodiments, the inner thickness 1110 may be about 1.87 mm.

Figure 12:
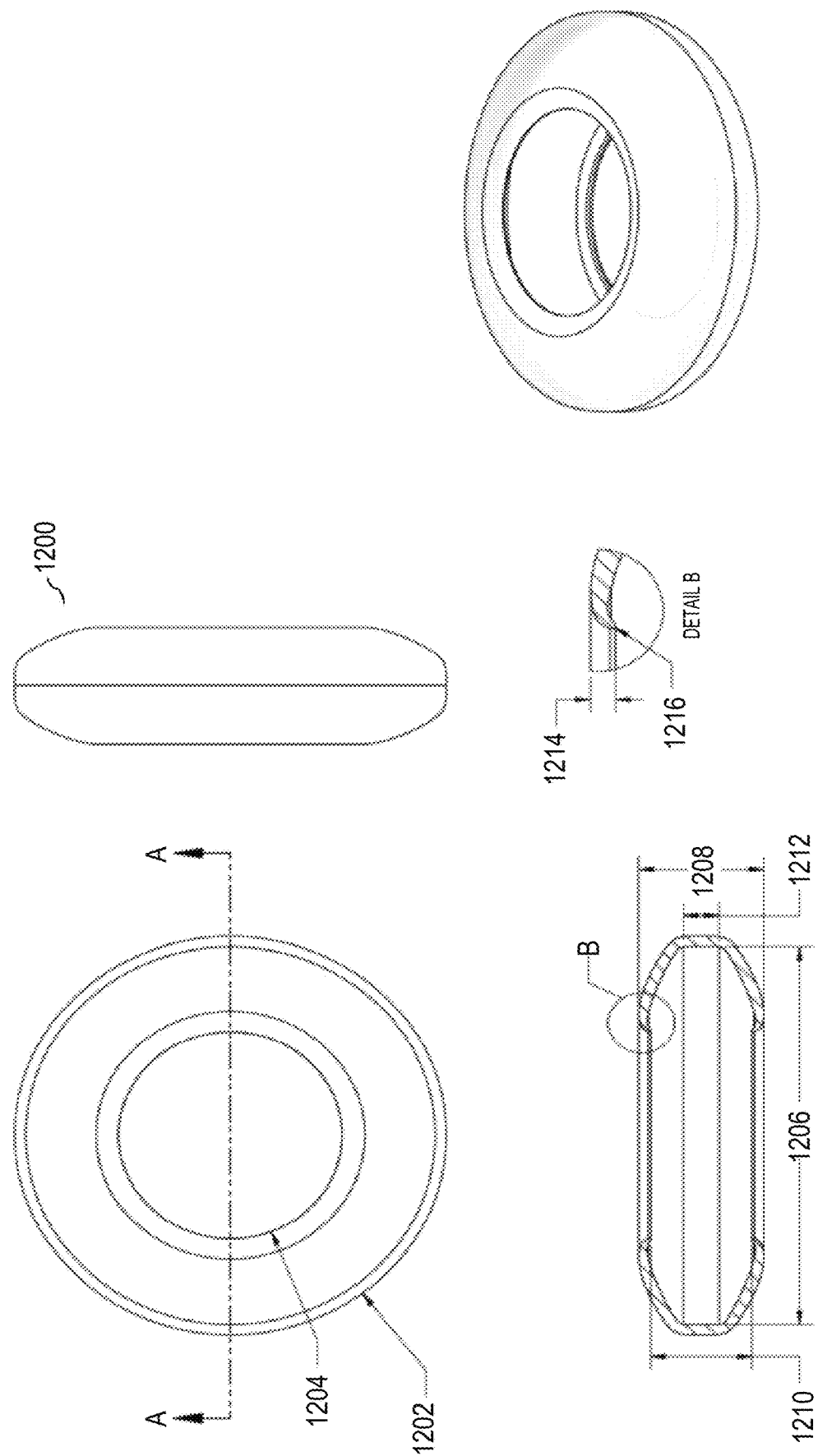
FIG. 12 illustrates another example prosthetic capsular device according to some embodiments herein.

FIG. 12 illustrates another example prosthetic capsular device according to some embodiments herein. In device 1200 of FIG. 12, the sidewall at the anterior portion of the device 1200 and the sidewall at the posterior of the device 1200 may form a slot of the device 1200. In some embodiments, the device 1200 may comprise a cylindrical middle portion perpendicular to the anterior opening and the posterior opening. Device 1200 may comprise a slot within the device cavity configured to secure an intraocular lens therein.

In some embodiments, a length of a major axis of the device 1200 or a length measured from the outermost end of one sidewall to the outermost end of another sidewall along a major axis of the device 1200 can be about 9.65 mm. In other embodiments, the length of the major axis of the device 1200 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1200 may comprise a diameter 1202 of the device 1200.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1204, which can be a diameter of an anterior opening and/or a posterior opening.

In some embodiments, the taper length 1214 may comprise a distance between the exterior surface of the sidewall at its most anterior/posterior point and the exterior surface at the anterior/posterior opening. In some embodiments, the exterior surface may comprise curved surfaces 1216 at the openings. The curved shape of the sidewalls may contribute to a reduction in post-surgical complications through minimization of contact or the severity of contact between the device 1200 and the iris. The curved shape of the sidewall of the device 1200 near the openings is shown in Detail B.

In some embodiments, the device 1200 may comprise an inner diameter 1206 comprising the distance between the interior surfaces of the sidewalls at the ridge. In some embodiments, the inner diameter 1206 may about 9.15 mm. In some embodiments, the interior diameter may be between about 5.00 mm and 15.00 mm.

In some embodiments, the device 1200 may comprise a slot thickness 1212 comprising the size of the slot. In some embodiments, the slot thickness 1212 may be about 0.80 mm. In some embodiments, the slot thickness 1212 may between about 0.10 mm and about 1.00 mm. In some embodiments, the slot thickness may be configured to reduce the possibility of lens tilt by an intraocular lens located in the slot.

In some embodiments, a thickness 1208 of the device 1200 may comprise a maximum distance between the anterior side and posterior side of the device 1200. In some embodiments, the thickness 1208 of the device 1200 may be about 2.80 mm. In some embodiments, the thickness 1208 of the device 1200 may be between about 0.5 mm and 4.0 mm. In some embodiments, the thickness 1208 of the device 1200 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the device 1200 may comprise an inner thickness 1210 comprising a distance between an inner surface of the sidewall at the anterior opening and an inner surface of the sidewall at the posterior opening. In some embodiments, the inner thickness 1210 may be about 2.27 mm.

Figure 13:
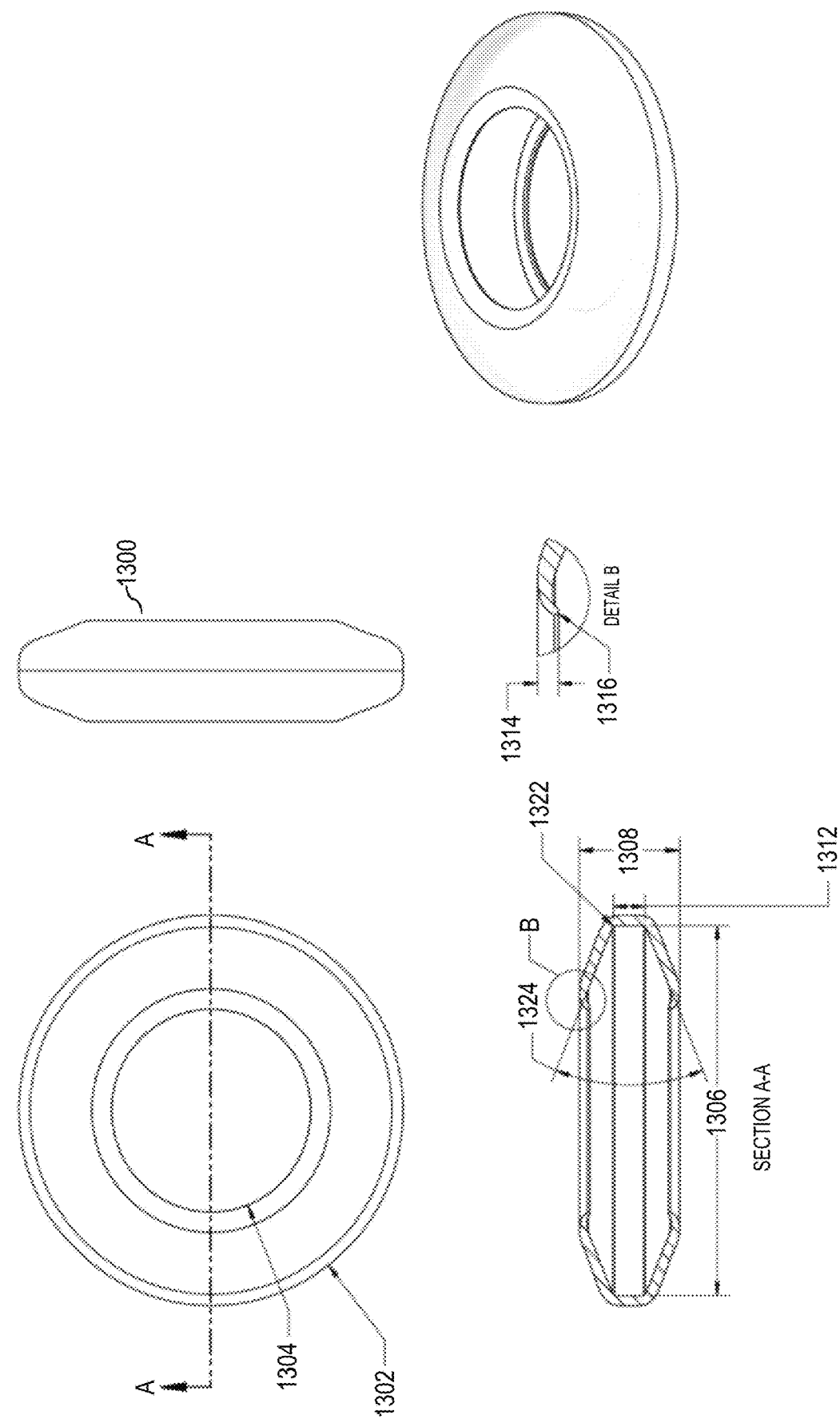
FIG. 13 illustrates another example prosthetic capsular device according to some embodiments herein.

FIG. 13 illustrates another example prosthetic capsular device according to some embodiments herein. In device 1300 of FIG. 13, the sidewall at the anterior portion of the device 1300 and the sidewall at the posterior of the device 1300 may form a sidewall angle 1324, formed at a slot of the device 1300. For example, the sidewall angle may be about 44°. Furthermore, device 1300 may not comprise any ribs, such as ribs 105 or ribs 305. Instead, device 1300 may comprise a slot within the device cavity configured to secure an intraocular lens therein.

In some embodiments, a length of a major axis of the device 1300 or a length measured from the outermost end of one sidewall to the outermost end of another sidewall along a major axis of the device 1300 can be about 9.65 mm. In other embodiments, the length of the major axis of the device 1300 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1300 may comprise a diameter 1302 of the device 1300.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1304, which can be a diameter of an anterior opening and/or a posterior opening.

In some embodiments, the taper length 1314 may comprise a distance between the exterior surface of the sidewall at its most anterior/posterior point and the exterior surface at the anterior/posterior opening. In some embodiments, the exterior surface may comprise curved surfaces 1322 and 1316 at the slot and at the openings, respectively. The curved shape of the sidewalls may contribute to a reduction in post-surgical complications through minimization of contact or the severity of contact between the device 1300 and the iris. The curved shape of the sidewall of the device 1300 near the openings is shown in Detail B.

In some embodiments, the device 1300 may comprise an inner diameter 1306 comprising the distance between the interior surfaces of the sidewalls at the ridge. In some embodiments, the inner diameter 1306 may about 9.15 mm. In some embodiments, the interior diameter may be between about 5.00 mm and 15.00 mm.

In some embodiments, the device 1300 may comprise a slot thickness 1312 comprising the size of the slot. In some embodiments, the slot thickness 1312 may be about 0.80 mm. In some embodiments, the slot thickness 1312 may between about 0.10 mm and about 1.00 mm. In some embodiments, the slot thickness may be configured to reduce the possibility of lens tilt by an intraocular lens located in the slot.

In some embodiments, a thickness 1308 of the device 1300 may comprise a maximum distance between the anterior side and posterior side of the device 1300. In some embodiments, the thickness 1308 of the device 1300 may be about 2.50 mm. In some embodiments, the thickness 1308 of the device 1300 may be between about 0.5 mm and 4.0 mm. In some embodiments, the thickness 1308 of the device 1300 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 14:
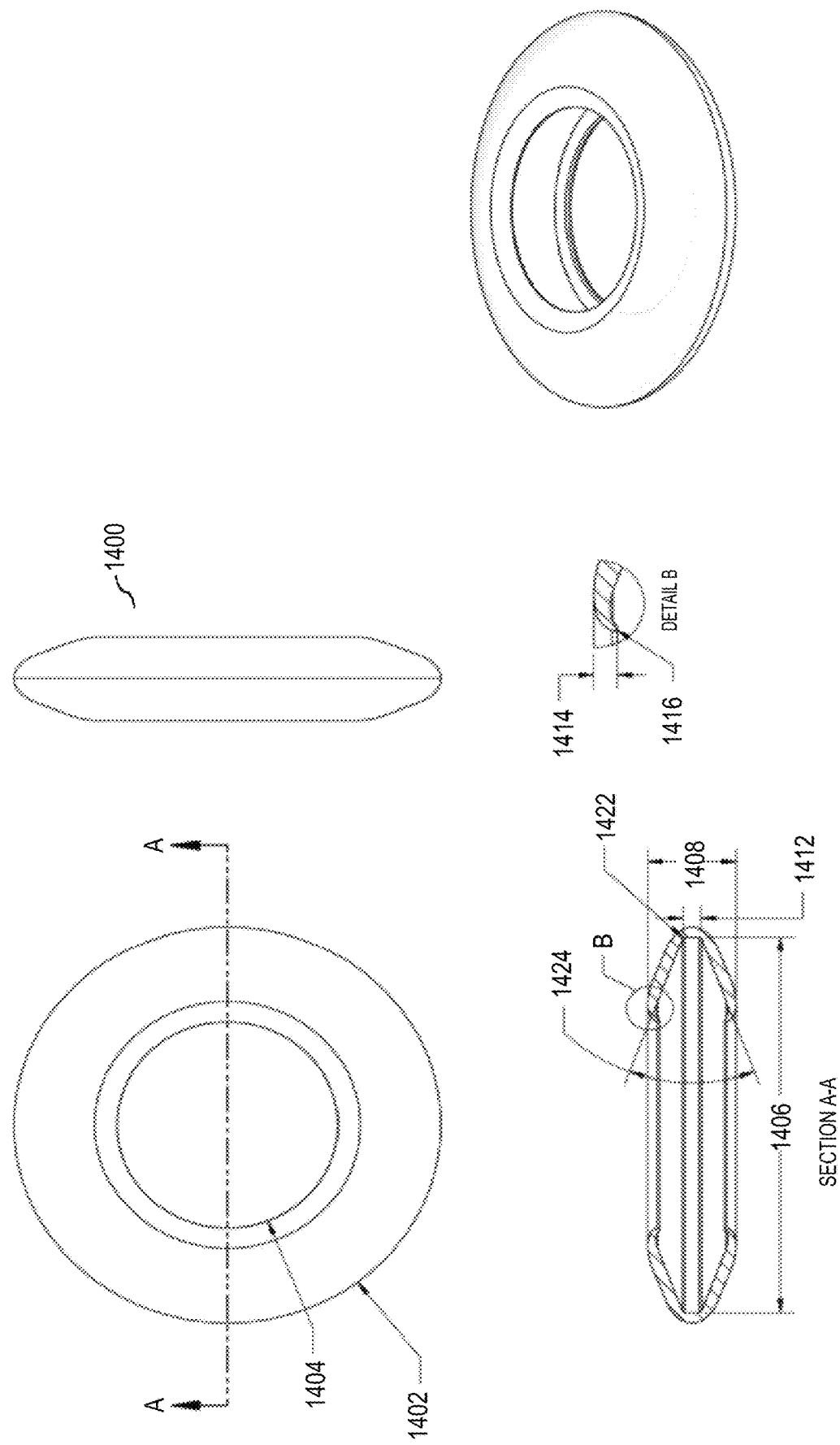
FIG. 14 illustrates another example prosthetic capsular device according to some embodiments herein.

FIG. 14 illustrates another example prosthetic capsular device according to some embodiments herein. In device 1400 of FIG. 14, the sidewall at the anterior portion of the device 1400 and the sidewall at the posterior of the device 1400 may form a sidewall angle 1424, formed at a slot of the device 1400. For example, the sidewall angle may be about 41°. Furthermore, device 1400 may not comprise any ribs, such as ribs 105 or ribs 305. Instead, device 1400 may comprise a slot within the device cavity configured to secure an intraocular lens therein.

In some embodiments, a length of a major axis of the device 1400 or a length measured from the outermost end of one sidewall to the outermost end of another sidewall along a major axis of the device 1400 can be about 9.65 mm. In other embodiments, the length of the major axis of the device 1400 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1400 may comprise a diameter 1402 of the device 1400.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1404, which can be a diameter of an anterior opening and/or a posterior opening.

In some embodiments, the taper length 1414 may comprise a distance between the exterior surface of the sidewall at its most anterior/posterior point and the exterior surface at the anterior/posterior opening. In some embodiments, the exterior surface may comprise curved surfaces 1422 and 1416 at the slot and at the openings, respectively. The curved shape of the sidewalls may contribute to a reduction in post-surgical complications through minimization of contact or the severity of contact between the device 1400 and the iris. The curved shape of the sidewall of the device 1400 near the openings is shown in Detail B.

In some embodiments, the device 1400 may comprise an inner diameter 1406 comprising the distance between the interior surfaces of the sidewalls at the ridge. In some embodiments, the inner diameter 1406 may about 9.15 mm. In some embodiments, the interior diameter may be between about 5.00 mm and 15.00 mm.

In some embodiments, the device 1400 may comprise a slot thickness 1412 comprising the size of the slot. In some embodiments, the slot thickness 1412 may be about 0.40 mm. In some embodiments, the slot thickness 1412 may between about 0.10 mm and about 1.00 mm. In some embodiments, the slot thickness may be configured to reduce the possibility of lens tilt by an intraocular lens located in the slot.

In some embodiments, a thickness 1408 of the device 1400 may comprise a maximum distance between the anterior side and posterior side of the device 1400. In some embodiments, the thickness 1408 of the device 1400 may be about 2.00 mm. In some embodiments, the thickness 1408 of the device 1400 may be between about 0.5 mm and 4.0 mm. In some embodiments, the thickness 1408 of the device 1400 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 15:
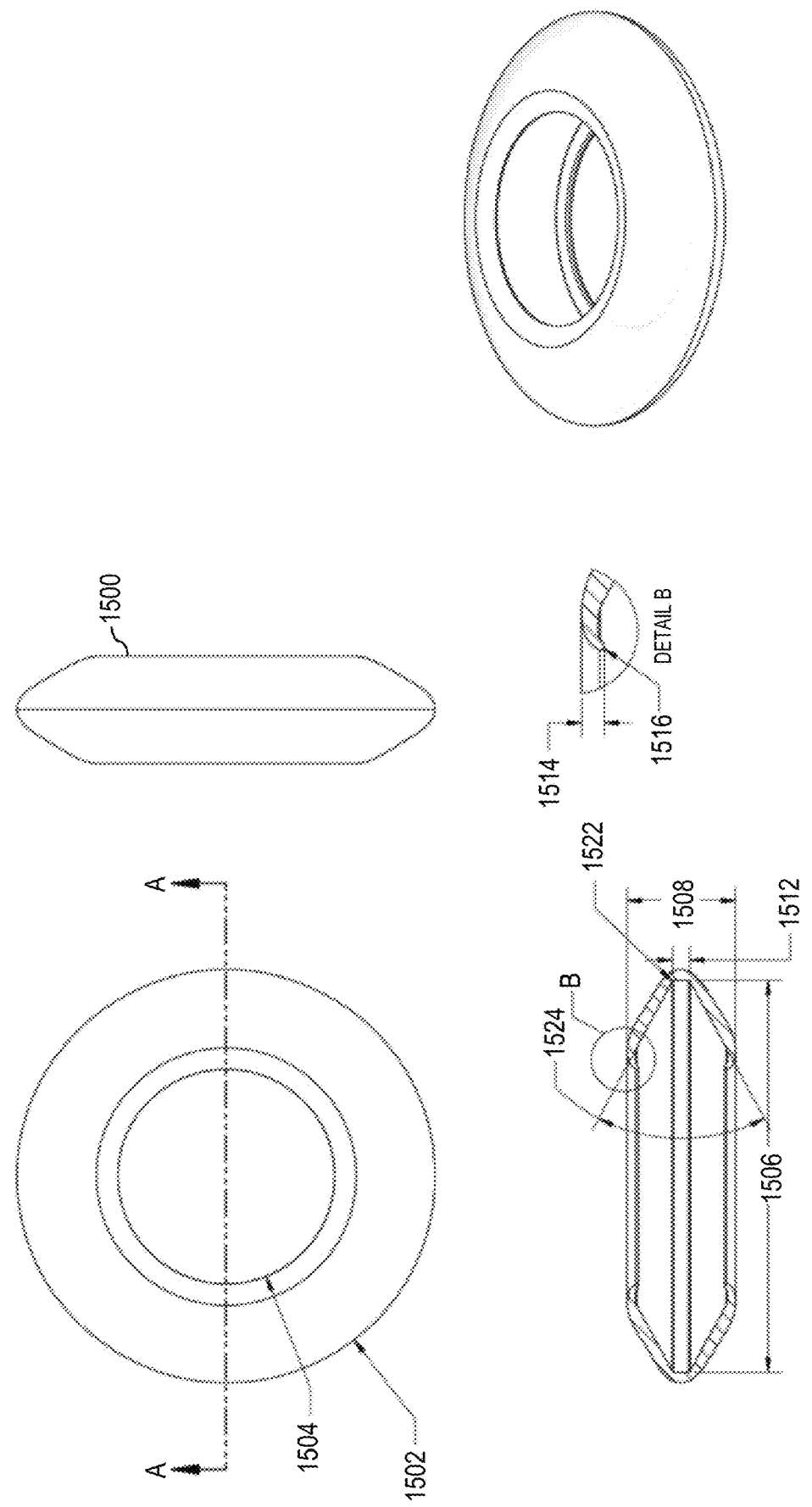
FIG. 15 illustrates another example prosthetic capsular device according to some embodiments herein.

FIG. 15 illustrates another example prosthetic capsular device according to some embodiments herein. In device 1500 of FIG. 15, the sidewall at the anterior portion of the device 1500 and the sidewall at the posterior of the device 1500 may form a sidewall angle 1524, formed at a slot of the device 1500. For example, the sidewall angle may be about 56°. Furthermore, device 1500 may not comprise any ribs, such as ribs 105 or ribs 305. Instead, device 1500 may comprise a slot within the device cavity configured to secure an intraocular lens therein.

In some embodiments, a length of a major axis of the device 1500 or a length measured from the outermost end of one sidewall to the outermost end of another sidewall along a major axis of the device 1500 can be about 9.65 mm. In other embodiments, the length of the major axis of the device 1500 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1500 may comprise a diameter 1502 of the device 1500.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1504, which can be a diameter of an anterior opening and/or a posterior opening.

In some embodiments, the taper length 1514 may comprise a distance between the exterior surface of the sidewall at its most anterior/posterior point and the exterior surface at the anterior/posterior opening. In some embodiments, the exterior surface may comprise curved surfaces 1522 and 1516 at the slot and at the openings, respectively. The curved shape of the sidewalls may contribute to a reduction in post-surgical complications through minimization of contact or the severity of contact between the device 1500 and the iris. The curved shape of the sidewall of the device 1500 near the openings is shown in Detail B.

In some embodiments, the device 1500 may comprise an inner diameter 1506 comprising the distance between the interior surfaces of the sidewalls at the ridge. In some embodiments, the inner diameter 1506 may about 9.15 mm. In some embodiments, the interior diameter may be between about 5.00 mm and 15.00 mm.

In some embodiments, the device 1500 may comprise a slot thickness 1512 comprising the size of the slot. In some embodiments, the slot thickness 1512 may be about 0.40 mm. In some embodiments, the slot thickness 1512 may between about 0.10 mm and about 1.00 mm. In some embodiments, the slot thickness may be configured to reduce the possibility of lens tilt by an intraocular lens located in the slot.

In some embodiments, a thickness 1508 of the device 1500 may comprise a maximum distance between the anterior side and posterior side of the device 1500. In some embodiments, the thickness 1508 of the device 1500 may be about 2.50 mm. In some embodiments, the thickness 1508 of the device 1500 may be between about 0.5 mm and 4.0 mm. In some embodiments, the thickness 1508 of the device 1500 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 16:
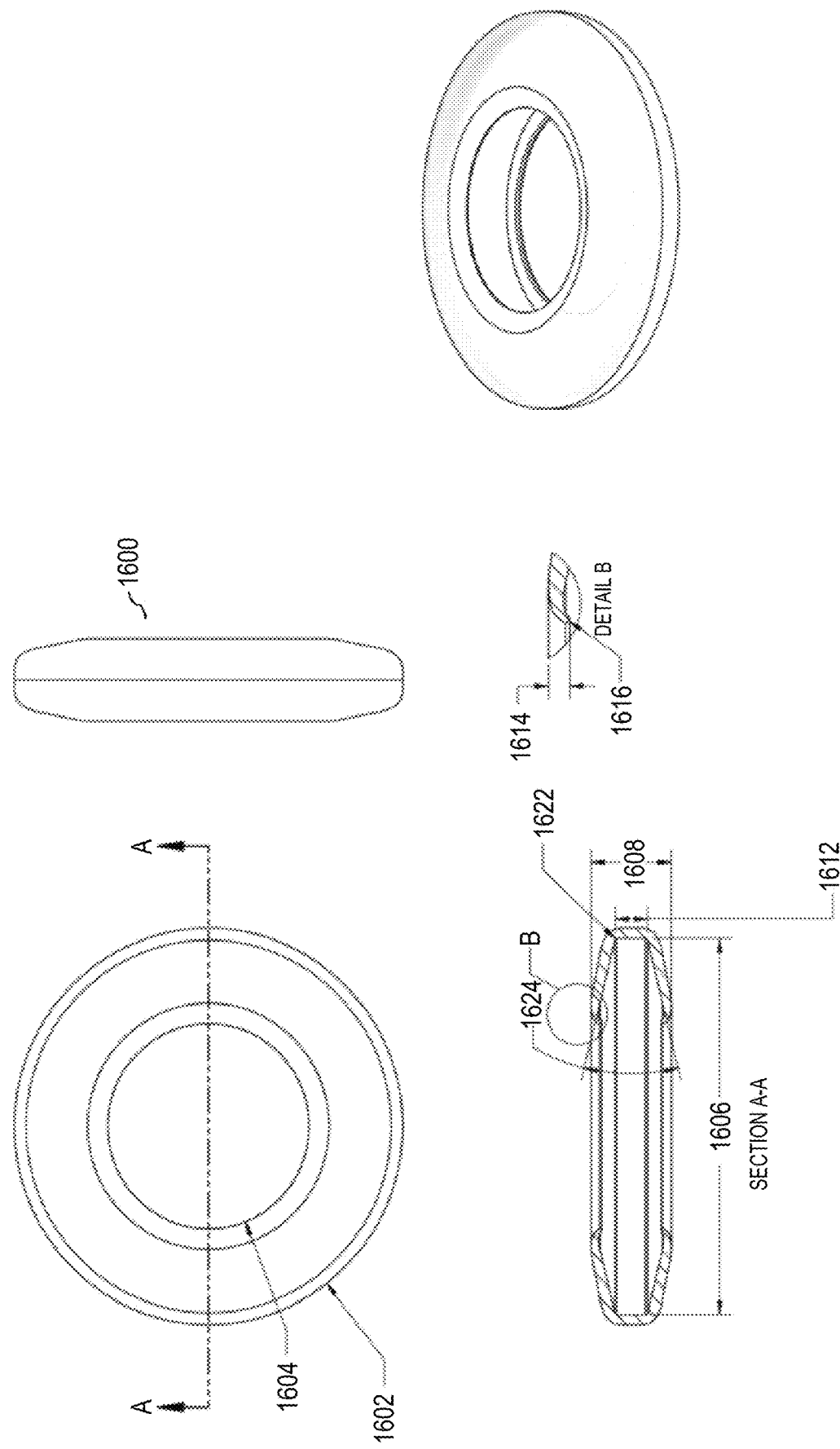
FIG. 16 illustrates another example prosthetic capsular device according to some embodiments herein.

FIG. 16 illustrates another example prosthetic capsular device according to some embodiments herein. In device 1600 of FIG. 16, the sidewall at the anterior portion of the device 1600 and the sidewall at the posterior of the device 1600 may form a slot of the device 1600. In some embodiments, the device 1600 may comprise a cylindrical middle portion perpendicular to the anterior opening and the posterior opening. Device 1600 may comprise a slot within the device cavity configured to secure an intraocular lens therein. In device 1600 of FIG. 16, the sidewall at the anterior portion of the device 1600 and the sidewall at the posterior of the device 1600 may form a sidewall angle 1624, formed at a slot of the device 1600. For example, the sidewall angle may be about 27°. Furthermore, device 1600 may not comprise any ribs, such as ribs 105 or ribs 305. Instead, device 1600 may comprise a slot within the device cavity configured to secure an intraocular lens therein.

In some embodiments, a length of a major axis of the device 1600 or a length measured from the outermost end of one sidewall to the outermost end of another sidewall along a major axis of the device 1600 can be about 9.65 mm. In other embodiments, the length of the major axis of the device 1600 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1600 may comprise a diameter 1602 of the device 1600.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1604, which can be a diameter of an anterior opening and/or a posterior opening.

In some embodiments, the taper length 1614 may comprise a distance between the exterior surface of the sidewall at its most anterior/posterior point and the exterior surface at the anterior/posterior opening. In some embodiments, the exterior surface may comprise curved surfaces 1622 and 1616 at the slot and the openings, respectively. The curved shape of the sidewalls may contribute to a reduction in post-surgical complications through minimization of contact or the severity of contact between the device 1600 and the iris. The curved shape of the sidewall of the device 1600 near the openings is shown in Detail B.

In some embodiments, the device 1600 may comprise an inner diameter 1606 comprising the distance between the interior surfaces of the sidewalls at the ridge. In some embodiments, the inner diameter 1606 may about 9.15 mm. In some embodiments, the interior diameter may be between about 5.00 mm and 15.00 mm.

In some embodiments, the device 1600 may comprise a slot thickness 1612 comprising the size of the slot. In some embodiments, the slot thickness 1612 may be about 0.80 mm. In some embodiments, the slot thickness 1612 may between about 0.10 mm and about 1.00 mm. In some embodiments, the slot thickness may be configured to reduce the possibility of lens tilt by an intraocular lens located in the slot.

In some embodiments, a thickness 1608 of the device 1600 may comprise a maximum distance between the anterior side and posterior side of the device 1600. In some embodiments, the thickness 1608 of the device 1600 may be about 2.00 mm. In some embodiments, the thickness 1608 of the device 1600 may be between about 0.5 mm and 4.0 mm. In some embodiments, the thickness 1608 of the device 1600 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 17:
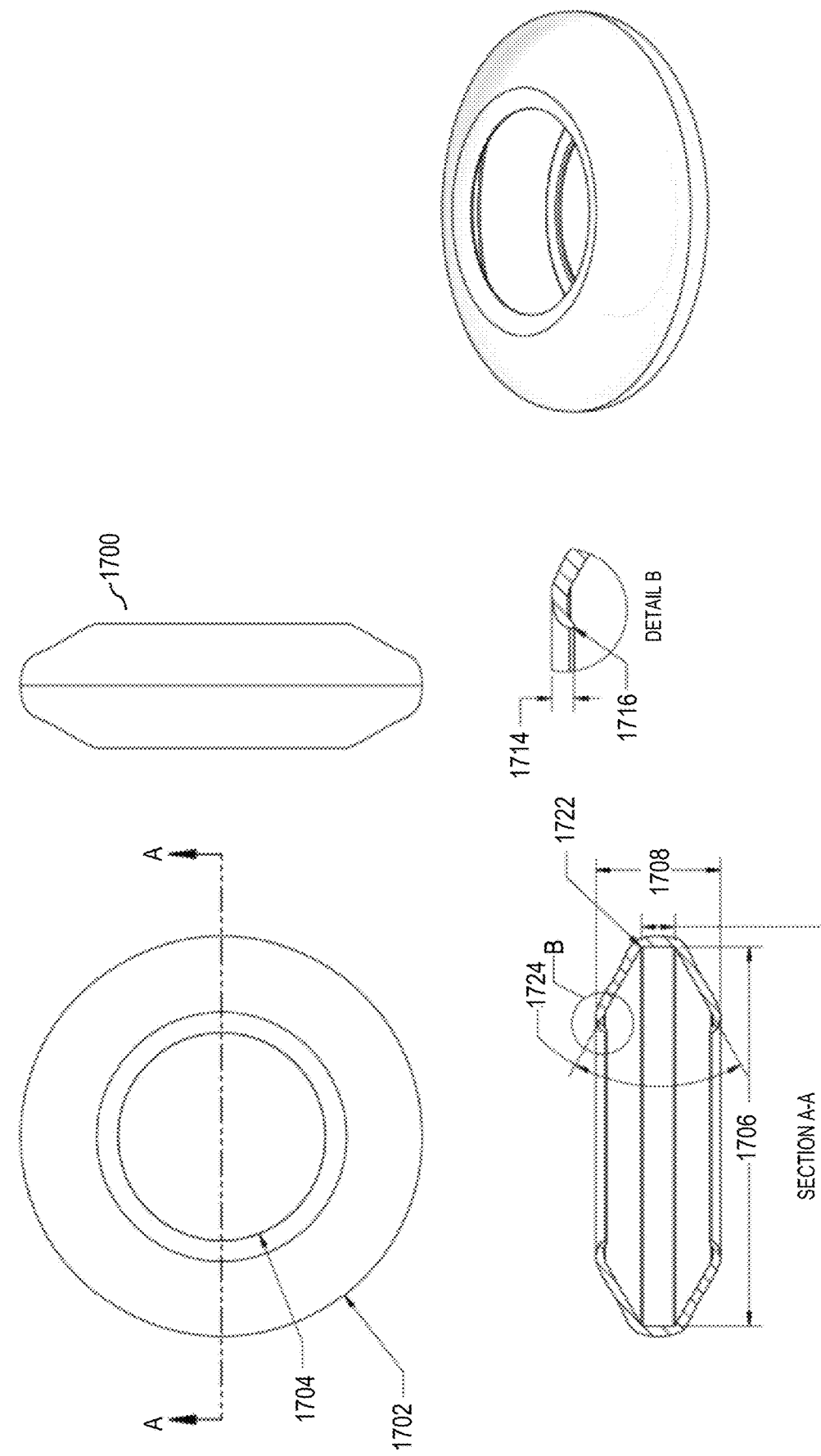
FIG. 17 illustrates another example prosthetic capsular device according to some embodiments herein.

FIG. 17 illustrates another example prosthetic capsular device according to some embodiments herein. In device 1700 of FIG. 17, the sidewall at the anterior portion of the device 1700 and the sidewall at the posterior of the device 1700 may form a slot of the device 1700. In some embodiments, the device 1700 may comprise a cylindrical middle portion perpendicular to the anterior opening and the posterior opening. Device 1700 may comprise a slot within the device cavity configured to secure an intraocular lens therein. In device 1700 of FIG. 17, the sidewall at the anterior portion of the device 1700 and the sidewall at the posterior of the device 1700 may form a sidewall angle 1724, formed at a slot of the device 1700. For example, the sidewall angle may be about 58°. Furthermore, device 1700 may not comprise any ribs, such as ribs 105 or ribs 305. Instead, device 1700 may comprise a slot within the device cavity configured to secure an intraocular lens therein.

In some embodiments, a length of a major axis of the device 1700 or a length measured from the outermost end of one sidewall to the outermost end of another sidewall along a major axis of the device 1700 can be about 9.65 mm. In other embodiments, the length of the major axis of the device 1700 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1700 may comprise a diameter 1702 of the device 1700.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1704, which can be a diameter of an anterior opening and/or a posterior opening.

In some embodiments, the taper length 1714 may comprise a distance between the exterior surface of the sidewall at its most anterior/posterior point and the exterior surface at the anterior/posterior opening. In some embodiments, the exterior surface may comprise curved surfaces 1722 and 1716 at the slot and the openings, respectively. The curved shape of the sidewalls may contribute to a reduction in post-surgical complications through minimization of contact or the severity of contact between the device 1700 and the iris. The curved shape of the sidewall of the device 1700 near the openings is shown in Detail B.

In some embodiments, the device 1700 may comprise an inner diameter 1706 comprising the distance between the interior surfaces of the sidewalls at the ridge. In some embodiments, the inner diameter 1706 may about 9.15 mm. In some embodiments, the interior diameter may be between about 5.00 mm and 15.00 mm.

In some embodiments, the device 1700 may comprise a slot thickness 1712 comprising the size of the slot. In some embodiments, the slot thickness 1712 may be about 0.80 mm. In some embodiments, the slot thickness 1712 may between about 0.10 mm and about 1.00 mm. In some embodiments, the slot thickness may be configured to reduce the possibility of lens tilt by an intraocular lens located in the slot.

In some embodiments, a thickness 1708 of the device 1700 may comprise a maximum distance between the anterior side and posterior side of the device 1700. In some embodiments, the thickness 1708 of the device 1700 may be about 3.00 mm. In some embodiments, the thickness 1708 of the device 1700 may be between about 0.5 mm and 4.0 mm. In some embodiments, the thickness 1708 of the device 1700 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 18:
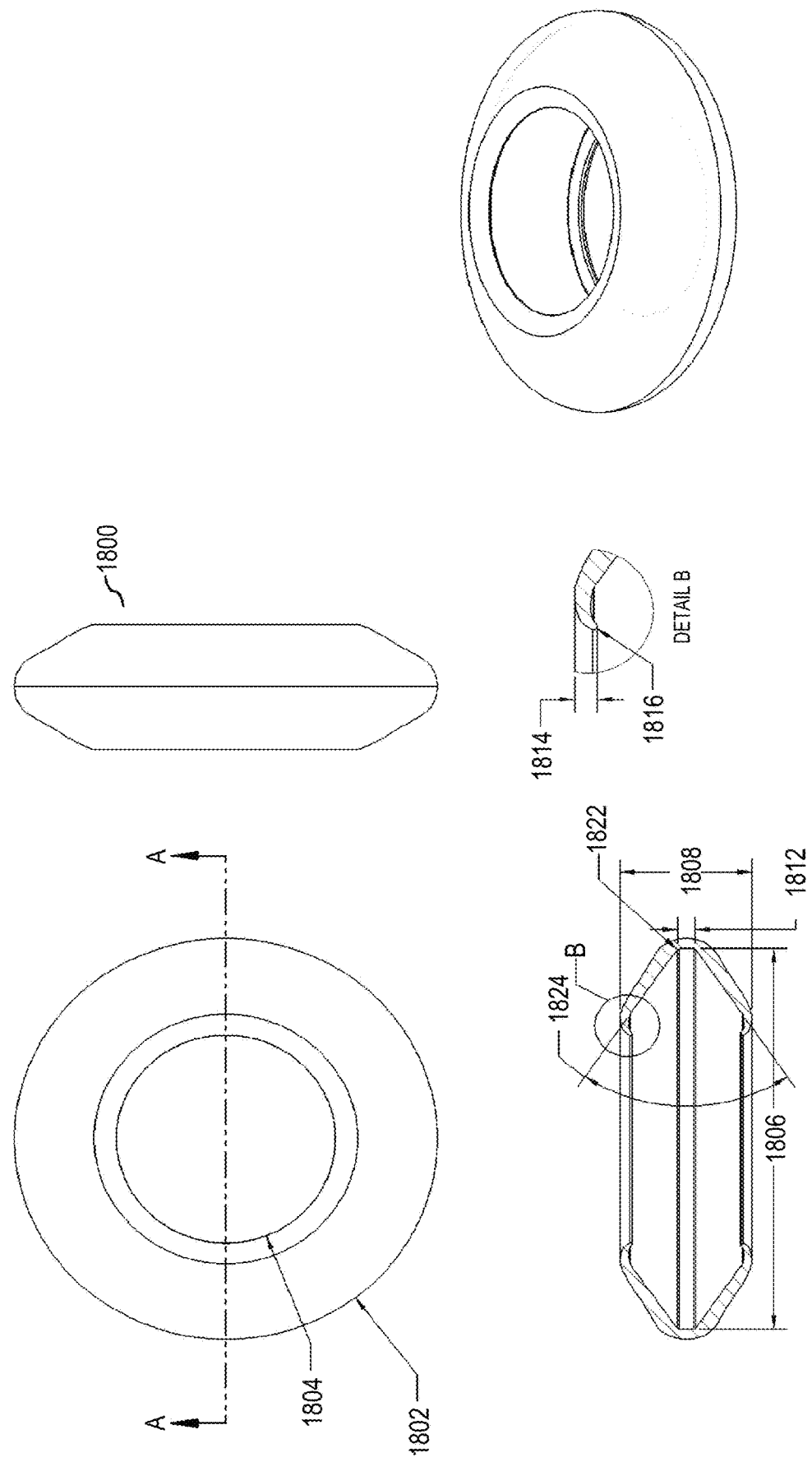
FIG. 18 illustrates another example prosthetic capsular device according to some embodiments herein.

FIG. 18 illustrates another example prosthetic capsular device according to some embodiments herein. In device 1800 of FIG. 18, the sidewall at the anterior portion of the device 1800 and the sidewall at the posterior of the device 1800 may form a slot of the device 1800. In some embodiments, the device 1800 may comprise a cylindrical middle portion perpendicular to the anterior opening and the posterior opening. Device 1800 may comprise a slot within the device cavity configured to secure an intraocular lens therein. In device 1800 of FIG. 18, the sidewall at the anterior portion of the device 1800 and the sidewall at the posterior of the device 1800 may form a sidewall angle 1824, formed at a slot of the device 1800. For example, the sidewall angle may be about 69°. Furthermore, device 1800 may not comprise any ribs, such as ribs 105 or ribs 305. Instead, device 1800 may comprise a slot within the device cavity configured to secure an intraocular lens therein.

In some embodiments, a length of a major axis of the device 1800 or a length measured from the outermost end of one sidewall to the outermost end of another sidewall along a major axis of the device 1800 can be about 9.65 mm. In other embodiments, the length of the major axis of the device 1800 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1800 may comprise a diameter 1802 of the device 1800.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1804, which can be a diameter of an anterior opening and/or a posterior opening.

In some embodiments, the taper length 1814 may comprise a distance between the exterior surface of the sidewall at its most anterior/posterior point and the exterior surface at the anterior/posterior opening. In some embodiments, the exterior surface may comprise curved surfaces 1822 and 1816 at the slot and the openings, respectively. The curved shape of the sidewalls may contribute to a reduction in post-surgical complications through minimization of contact or the severity of contact between the device 1800 and the iris. The curved shape of the sidewall of the device 1800 near the openings is shown in Detail B.

In some embodiments, the device 1800 may comprise an inner diameter 1806 comprising the distance between the interior surfaces of the sidewalls at the ridge. In some embodiments, the inner diameter 1806 may about 9.15 mm. In some embodiments, the interior diameter may be between about 5.00 mm and 15.00 mm.

In some embodiments, the device 1800 may comprise a slot thickness 1812 comprising the size of the slot. In some embodiments, the slot thickness 1812 may be about 0.40 mm. In some embodiments, the slot thickness 1812 may between about 0.10 mm and about 1.00 mm. In some embodiments, the slot thickness may be configured to reduce the possibility of lens tilt by an intraocular lens located in the slot.

In some embodiments, a thickness 1808 of the device 1800 may comprise a maximum distance between the anterior side and posterior side of the device 1800. In some embodiments, the thickness 1808 of the device 1800 may be about 3.00 mm. In some embodiments, the thickness 1808 of the device 1800 may be between about 0.5 mm and 4.0 mm. In some embodiments, the thickness 1808 of the device 1800 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 19:
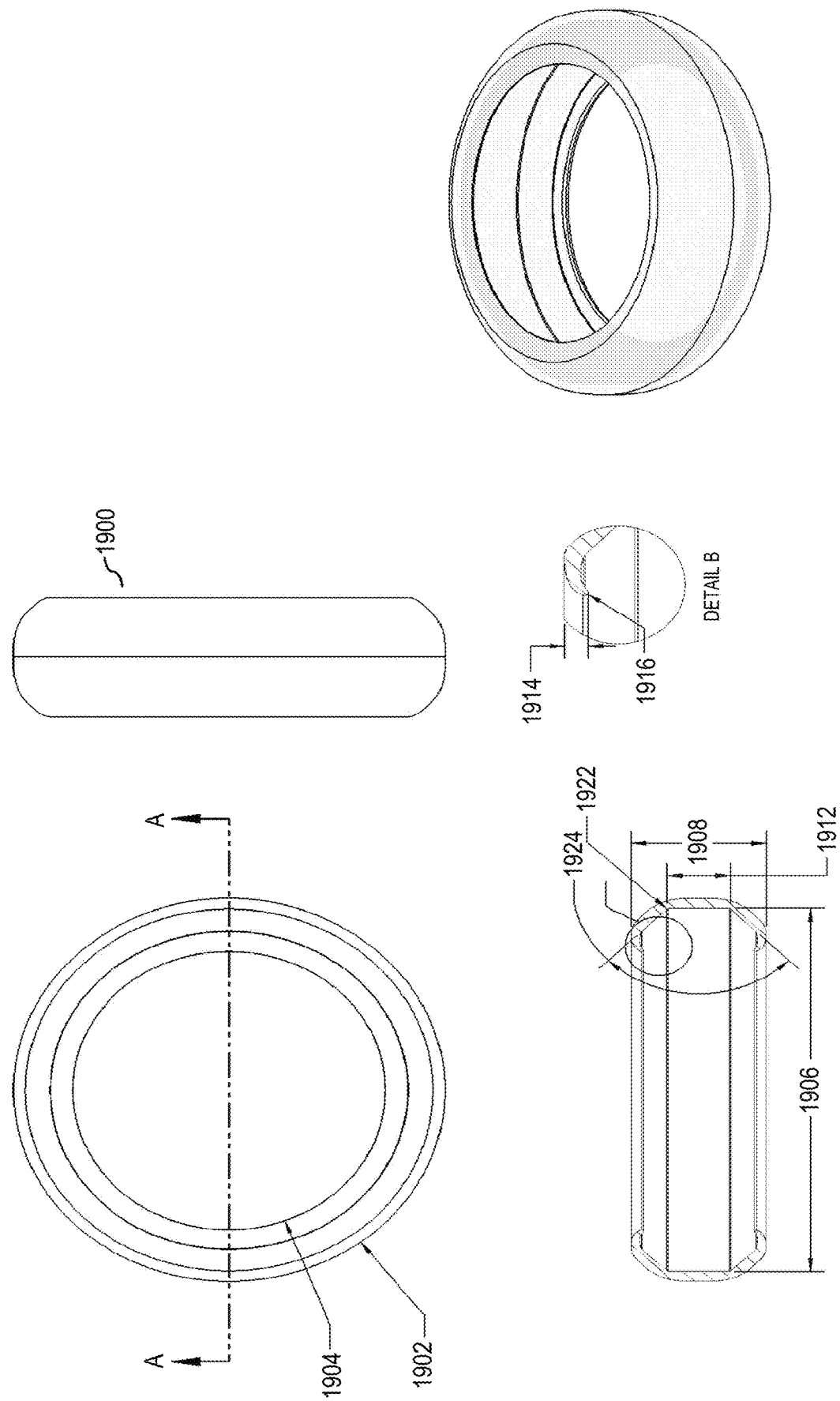
FIG. 19 illustrates another example prosthetic capsular device according to some embodiments herein.

FIG. 19 illustrates another example prosthetic capsular device according to some embodiments herein. In device 1900 of FIG. 19, the sidewall at the anterior portion of the device 1900 and the sidewall at the posterior of the device 1900 may form a slot of the device 1900. In some embodiments, the device 1900 may comprise a cylindrical middle portion perpendicular to the anterior opening and the posterior opening. Device 1900 may comprise a slot within the device cavity configured to secure an intraocular lens therein. In device 1900 of FIG. 19, the sidewall at the anterior portion of the device 1900 and the sidewall at the posterior of the device 1900 may form a sidewall angle 1924, formed at a slot of the device 1900. For example, the sidewall angle may be about 91°. Furthermore, device 1900 may not comprise any ribs, such as ribs 105 or ribs 305. Instead, device 1900 may comprise a slot within the device cavity configured to secure an intraocular lens therein.

In some embodiments, a length of a major axis of the device 1900 or a length measured from the outermost end of one sidewall to the outermost end of another sidewall along a major axis of the device 1900 can be about 9.65 mm. In other embodiments, the length of the major axis of the device 1900 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 1900 may comprise a diameter 1902 of the device 1900.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 1904, which can be a diameter of an anterior opening and/or a posterior opening.

In some embodiments, the taper length 1914 may comprise a distance between the exterior surface of the sidewall at its most anterior/posterior point and the exterior surface at the anterior/posterior opening. In some embodiments, the exterior surface may comprise curved surfaces 1922 and 1916 at the slot and the openings, respectively. The curved shape of the sidewalls may contribute to a reduction in post-surgical complications through minimization of contact or the severity of contact between the device 1900 and the iris. The curved shape of the sidewall of the device 1900 near the openings is shown in Detail B.

In some embodiments, the device 1900 may comprise an inner diameter 1906 comprising the distance between the interior surfaces of the sidewalls at the ridge. In some embodiments, the inner diameter 1906 may about 9.15 mm. In some embodiments, the interior diameter may be between about 5.00 mm and 15.00 mm.

In some embodiments, the device 1900 may comprise a slot thickness 1912 comprising the size of the slot. In some embodiments, the slot thickness 1912 may be about 1.40 mm. In some embodiments, the slot thickness 1912 may between about 0.10 mm and about 2.00 mm. In some embodiments, the slot thickness may be configured to reduce the possibility of lens tilt by an intraocular lens located in the slot.

In some embodiments, a thickness 1908 of the device 1900 may comprise a maximum distance between the anterior side and posterior side of the device 1900. In some embodiments, the thickness 1908 of the device 1900 may be about 3.00 mm. In some embodiments, the thickness 1908 of the device 1900 may be between about 0.5 mm and 4.0 mm. In some embodiments, the thickness 1908 of the device 1900 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 20:
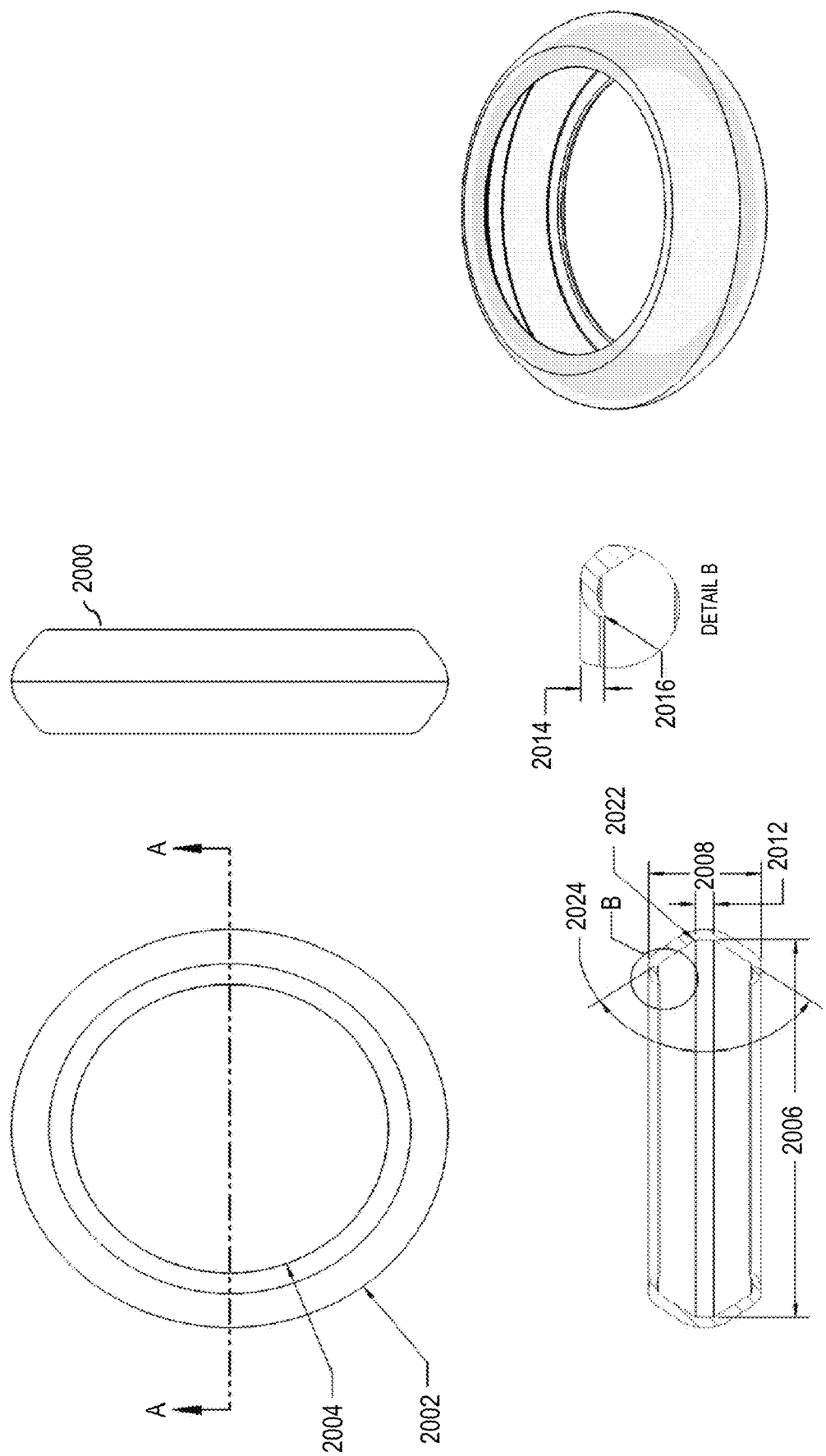
FIG. 20 illustrates another example prosthetic capsular device according to some embodiments herein.

FIG. 20 illustrates another example prosthetic capsular device according to some embodiments herein. In device 2000 of FIG. 20, the sidewall at the anterior portion of the device 2000 and the sidewall at the posterior of the device 2000 may form a slot of the device 2000. In some embodiments, the device 2000 may comprise a cylindrical middle portion perpendicular to the anterior opening and the posterior opening. Device 2000 may comprise a slot within the device cavity configured to secure an intraocular lens therein. In device 2000 of FIG. 20, the sidewall at the anterior portion of the device 2000 and the sidewall at the posterior of the device 2000 may form a sidewall angle 2024, formed at a slot of the device 2000. For example, the sidewall angle may be about 111°. Furthermore, device 2000 may not comprise any ribs, such as ribs 105 or ribs 305. Instead, device 2000 may comprise a slot within the device cavity configured to secure an intraocular lens therein.

In some embodiments, a length of a major axis of the device 2000 or a length measured from the outermost end of one sidewall to the outermost end of another sidewall along a major axis of the device 2000 can be about 9.65 mm. In other embodiments, the length of the major axis of the device 2000 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2000 may comprise a diameter 2002 of the device 2000.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2004, which can be a diameter of an anterior opening and/or a posterior opening.

In some embodiments, the taper length 2014 may comprise a distance between the exterior surface of the sidewall at its most anterior/posterior point and the exterior surface at the anterior/posterior opening. In some embodiments, the exterior surface may comprise curved surfaces 2022 and 2016 at the slot and the openings, respectively. The curved shape of the sidewalls may contribute to a reduction in post-surgical complications through minimization of contact or the severity of contact between the device 2000 and the iris. The curved shape of the sidewall of the device 2000 near the openings is shown in Detail B.

In some embodiments, the device 2000 may comprise an inner diameter 2006 comprising the distance between the interior surfaces of the sidewalls at the ridge. In some embodiments, the inner diameter 2006 may about 9.15 mm. In some embodiments, the interior diameter may be between about 5.00 mm and 15.00 mm.

In some embodiments, the device 2000 may comprise a slot thickness 2012 comprising the size of the slot. In some embodiments, the slot thickness 2012 may be about 0.40 mm. In some embodiments, the slot thickness 2012 may between about 0.10 mm and about 2.00 mm. In some embodiments, the slot thickness may be configured to reduce the possibility of lens tilt by an intraocular lens located in the slot.

In some embodiments, a thickness 2008 of the device 2000 may comprise a maximum distance between the anterior side and posterior side of the device 2000. In some embodiments, the thickness 2008 of the device 2000 may be about 2.50 mm. In some embodiments, the thickness 2008 of the device 2000 may be between about 0.5 mm and 4.0 mm. In some embodiments, the thickness 2008 of the device 2000 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 21:
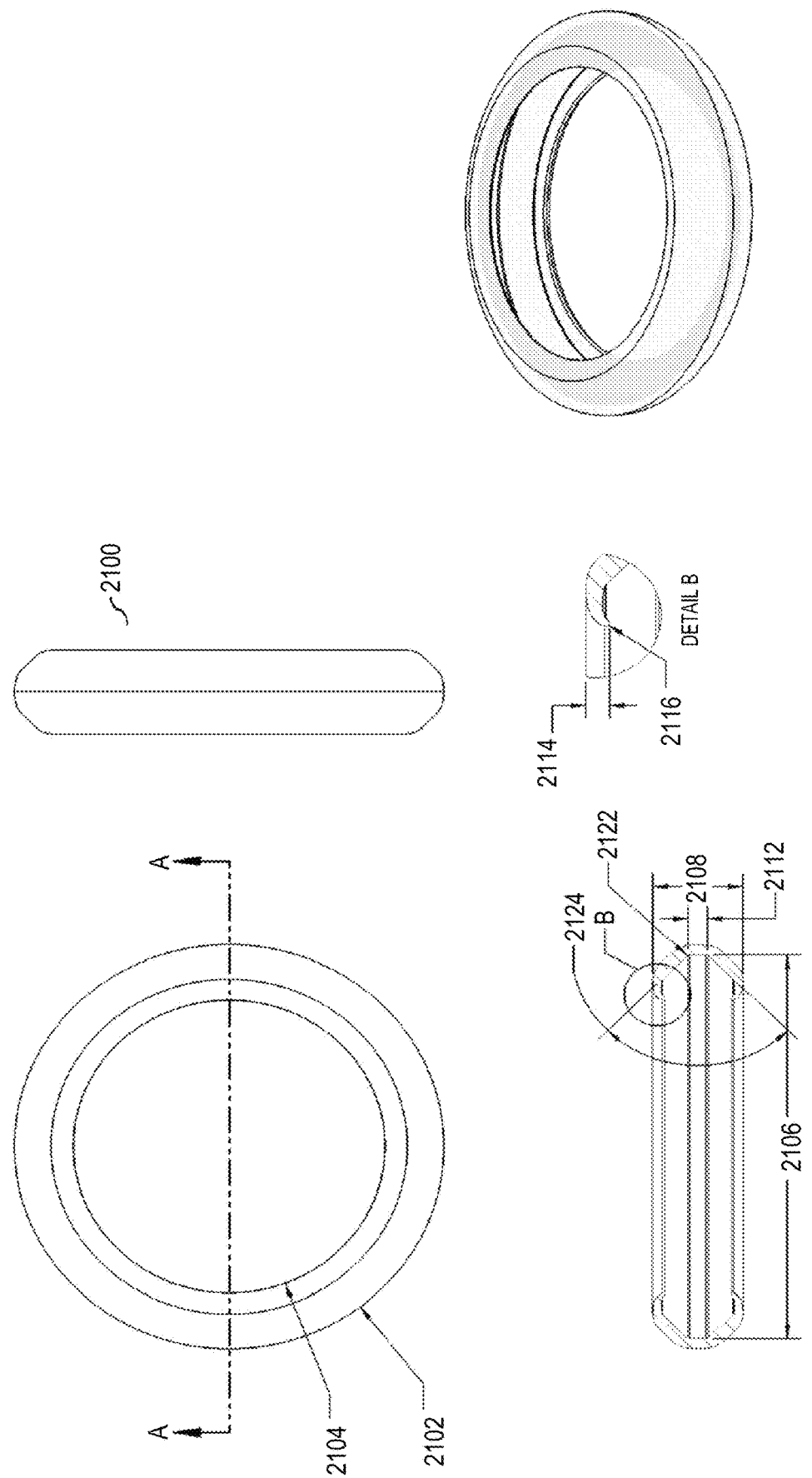
FIG. 21 illustrates another example prosthetic capsular device according to some embodiments herein.

FIG. 21 illustrates another example prosthetic capsular device according to some embodiments herein. In device 2100 of FIG. 21, the sidewall at the anterior portion of the device 2100 and the sidewall at the posterior of the device 2100 may form a slot of the device 2100. In some embodiments, the device 2100 may comprise a cylindrical middle portion perpendicular to the anterior opening and the posterior opening. Device 2100 may comprise a slot within the device cavity configured to secure an intraocular lens therein. In device 2100 of FIG. 21, the sidewall at the anterior portion of the device 2100 and the sidewall at the posterior of the device 2100 may form a sidewall angle 2124, formed at a slot of the device 2100. For example, the sidewall angle may be about 91°. Furthermore, device 2100 may not comprise any ribs, such as ribs 105 or ribs 305. Instead, device 2100 may comprise a slot within the device cavity configured to secure an intraocular lens therein.

In some embodiments, a length of a major axis of the device 2100 or a length measured from the outermost end of one sidewall to the outermost end of another sidewall along a major axis of the device 2100 can be about 9.65 mm. In other embodiments, the length of the major axis of the device 2100 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2100 may comprise a diameter 2102 of the device 2100.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2104, which can be a diameter of an anterior opening and/or a posterior opening.

In some embodiments, the taper length 2114 may comprise a distance between the exterior surface of the sidewall at its most anterior/posterior point and the exterior surface at the anterior/posterior opening. In some embodiments, the exterior surface may comprise curved surfaces 2122 and 2116 at the slot and the openings, respectively. The curved shape of the sidewalls may contribute to a reduction in post-surgical complications through minimization of contact or the severity of contact between the device 2100 and the iris. The curved shape of the sidewall of the device 2100 near the openings is shown in Detail B.

In some embodiments, the device 2100 may comprise an inner diameter 2106 comprising the distance between the interior surfaces of the sidewalls at the ridge. In some embodiments, the inner diameter 2106 may about 9.15 mm.

In some embodiments, the interior diameter may be between about 5.00 mm and 15.00 mm.

In some embodiments, the device 2100 may comprise a slot thickness 2112 comprising the size of the slot. In some embodiments, the slot thickness 2112 may be about 0.40 mm. In some embodiments, the slot thickness 2112 may between about 0.10 mm and about 2.00 mm. In some embodiments, the slot thickness may be configured to reduce the possibility of lens tilt by an intraocular lens located in the slot.

In some embodiments, a thickness 2108 of the device 2100 may comprise a maximum distance between the anterior side and posterior side of the device 2100. In some embodiments, the thickness 2108 of the device 2100 may be about 2.00 mm. In some embodiments, the thickness 2108 of the device 2100 may be between about 0.5 mm and 4.0 mm. In some embodiments, the thickness 2108 of the device 2100 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 22:
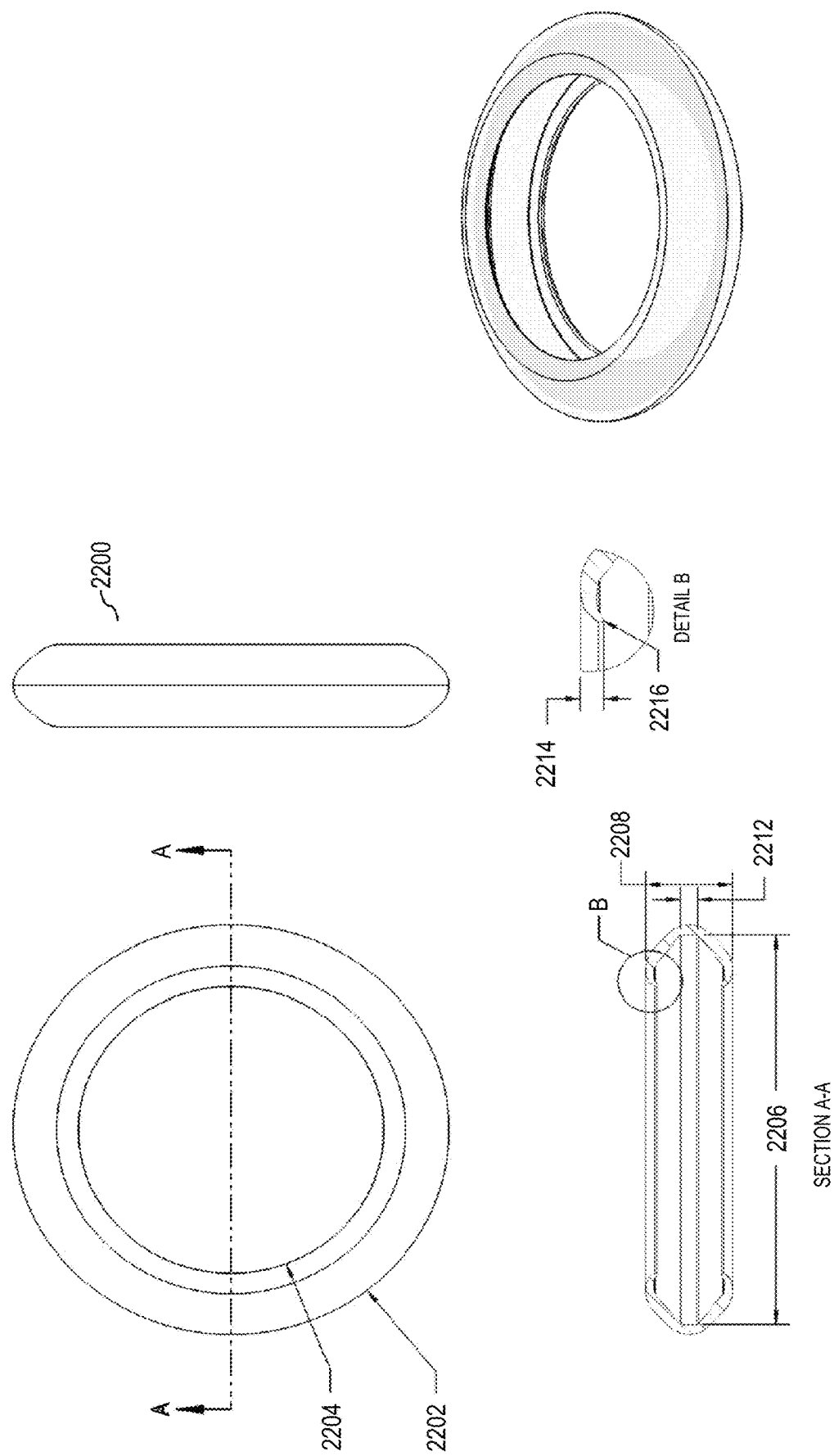
FIG. 22 illustrates another example prosthetic capsular device according to some embodiments herein.

FIG. 22 illustrates another example prosthetic capsular device according to some embodiments herein. In device 2200 of FIG. 22, the sidewall at the anterior portion of the device 2200 and the sidewall at the posterior of the device 2200 may form a slot of the device 2200. In some embodiments, the device 2200 may comprise a cylindrical middle portion perpendicular to the anterior opening and the posterior opening. Device 2200 may comprise a slot within the device cavity configured to secure an intraocular lens therein.

In some embodiments, a length of a major axis of the device 2200 or a length measured from the outermost end of one sidewall to the outermost end of another sidewall along a major axis of the device 2200 can be about 10.00 mm. In other embodiments, the length of the major axis of the device 2200 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2200 may comprise a diameter 2202 of the device 2200.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2204, which can be a diameter of an anterior opening and/or a posterior opening.

In some embodiments, the taper length 2214 may comprise a distance between the exterior surface of the sidewall at its most anterior/posterior point and the exterior surface at the anterior/posterior opening. In some embodiments, the exterior surface may comprise curved surfaces 2216 at the openings. The curved shape of the sidewalls may contribute to a reduction in post-surgical complications through minimization of contact or the severity of contact between the device 2200 and the iris. The curved shape of the sidewall of the device 2200 near the openings is shown in Detail B.

In some embodiments, the device 2200 may comprise an inner diameter 2206 comprising the distance between the interior surfaces of the sidewalls at the ridge. In some embodiments, the inner diameter 2206 may about 9.50 mm. In some embodiments, the interior diameter may be between about 5.00 mm and 15.00 mm.

In some embodiments, the device 2200 may comprise a slot thickness 2212 comprising the size of the slot. In some embodiments, the slot thickness 2212 may be about 0.40 mm. In some embodiments, the slot thickness 2212 may between about 0.10 mm and about 2.00 mm. In some embodiments, the slot thickness may be configured to reduce the possibility of lens tilt by an intraocular lens located in the slot.

In some embodiments, a thickness 2208 of the device 2200 may comprise a maximum distance between the anterior side and posterior side of the device 2200. In some embodiments, the thickness 2208 of the device 2200 may be about 2.00 mm. In some embodiments, the thickness 2208 of the device 2200 may be between about 0.5 mm and 4.0 mm. In some embodiments, the thickness 2208 of the device 2200 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 23:
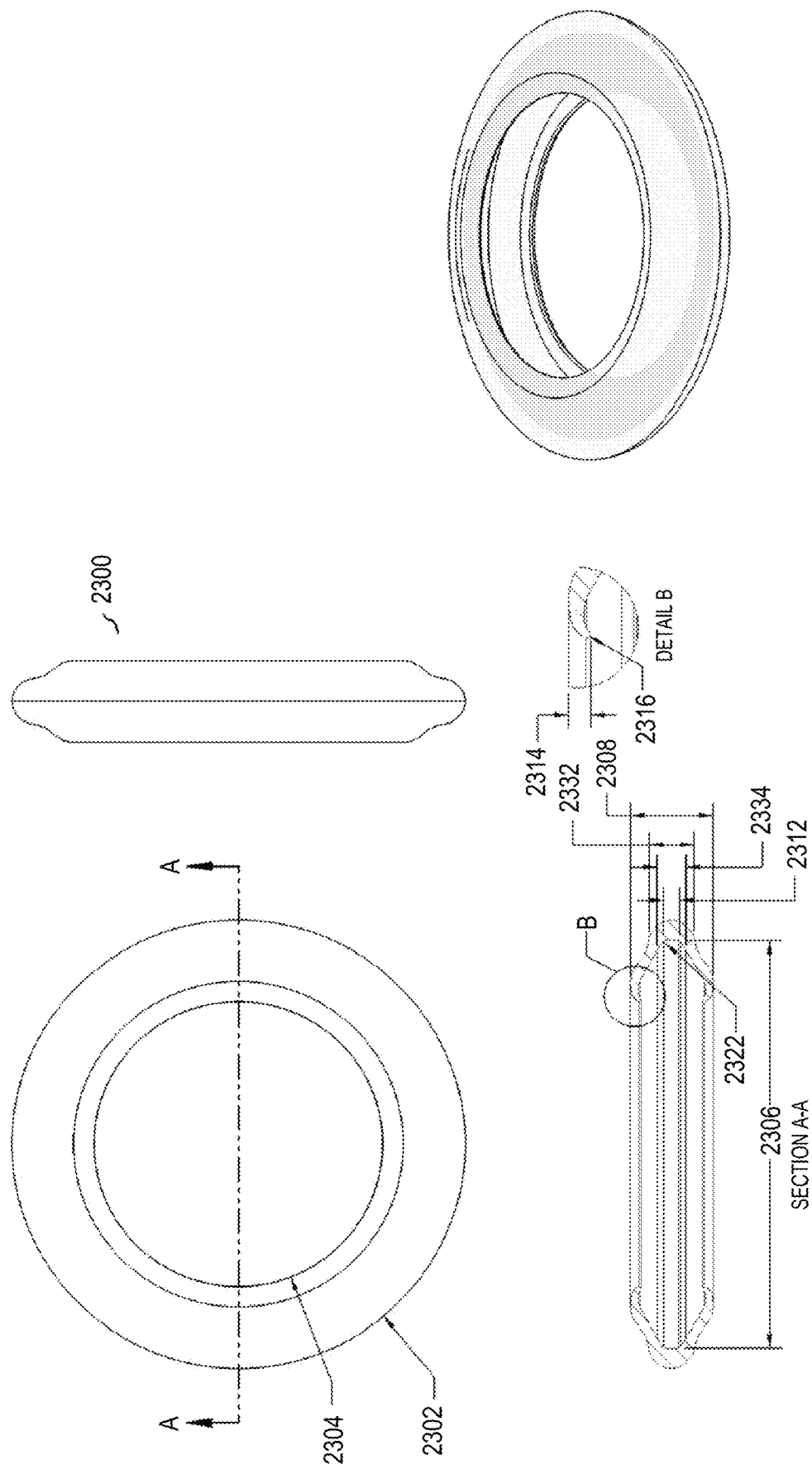
FIG. 23 illustrates another example prosthetic capsular device according to some embodiments herein.

FIG. 23 illustrates another example prosthetic capsular device according to some embodiments herein. In device 2300 of FIG. 23, the sidewall at the anterior portion of the device 2300 and the sidewall at the posterior of the device 2300 may form a slot of the device 2300. In some embodiments, the device 2300 may comprise a rounded middle portion protruding laterally outward from the anterior portion and the posterior portion. In some embodiments, the rounded middle portion may comprise a middle portion length 2332, measured from the exterior of the device. In some embodiments, the middle portion length 2332 may be about 1.08 mm. In some embodiments, the rounded middle portion may comprise a middle portion interior length 2334, measuring on the interior of the device. In some embodiments, the middle portion interior length 2334 may be about 0.70 mm. Device 2300 may comprise a slot within the device cavity configured to secure an intraocular lens therein.

In some embodiments, a length of a major axis of the device 2300 or a length measured from the outermost end of one sidewall to the outermost end of another sidewall along a major axis of the device 2300 can be about 11.00 mm. In other embodiments, the length of the major axis of the device 2300 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2300 may comprise a diameter 2302 of the device 2300.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2304, which can be a diameter of an anterior opening and/or a posterior opening.

In some embodiments, the taper length 2314 may comprise a distance between the exterior surface of the sidewall at its most anterior/posterior point and the exterior surface at the anterior/posterior opening. In some embodiments, the exterior surface may comprise curved surfaces 2322 and 2316 at the slot and the openings, respectively. The curved shape of the sidewalls may contribute to a reduction in post-surgical complications through minimization of contact or the severity of contact between the device 2300 and the iris. The curved shape of the sidewall of the device 2300 near the openings is shown in Detail B.

In some embodiments, the device 2300 may comprise an inner diameter 2306 comprising the distance between the interior surfaces of the sidewalls at the ridge. In some embodiments, the inner diameter 2306 may about 10.00 mm. In some embodiments, the interior diameter may be between about 5.00 mm and 15.00 mm.

In some embodiments, the device 2300 may comprise a slot thickness 2312 comprising the size of the slot. In some embodiments, the slot thickness 2312 may be about 0.40 mm. In some embodiments, the slot thickness 2312 may between about 0.10 mm and about 2.00 mm. In some embodiments, the slot thickness may be configured to reduce the possibility of lens tilt by an intraocular lens located in the slot.

In some embodiments, a thickness 2308 of the device 2300 may comprise a maximum distance between the anterior side and posterior side of the device 2300. In some embodiments, the thickness 2308 of the device 2300 may be about 2.00 mm. In some embodiments, the thickness 2308 of the device 2300 may be between about 0.5 mm and 4.0 mm. In some embodiments, the thickness 2308 of the device 2300 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 24:
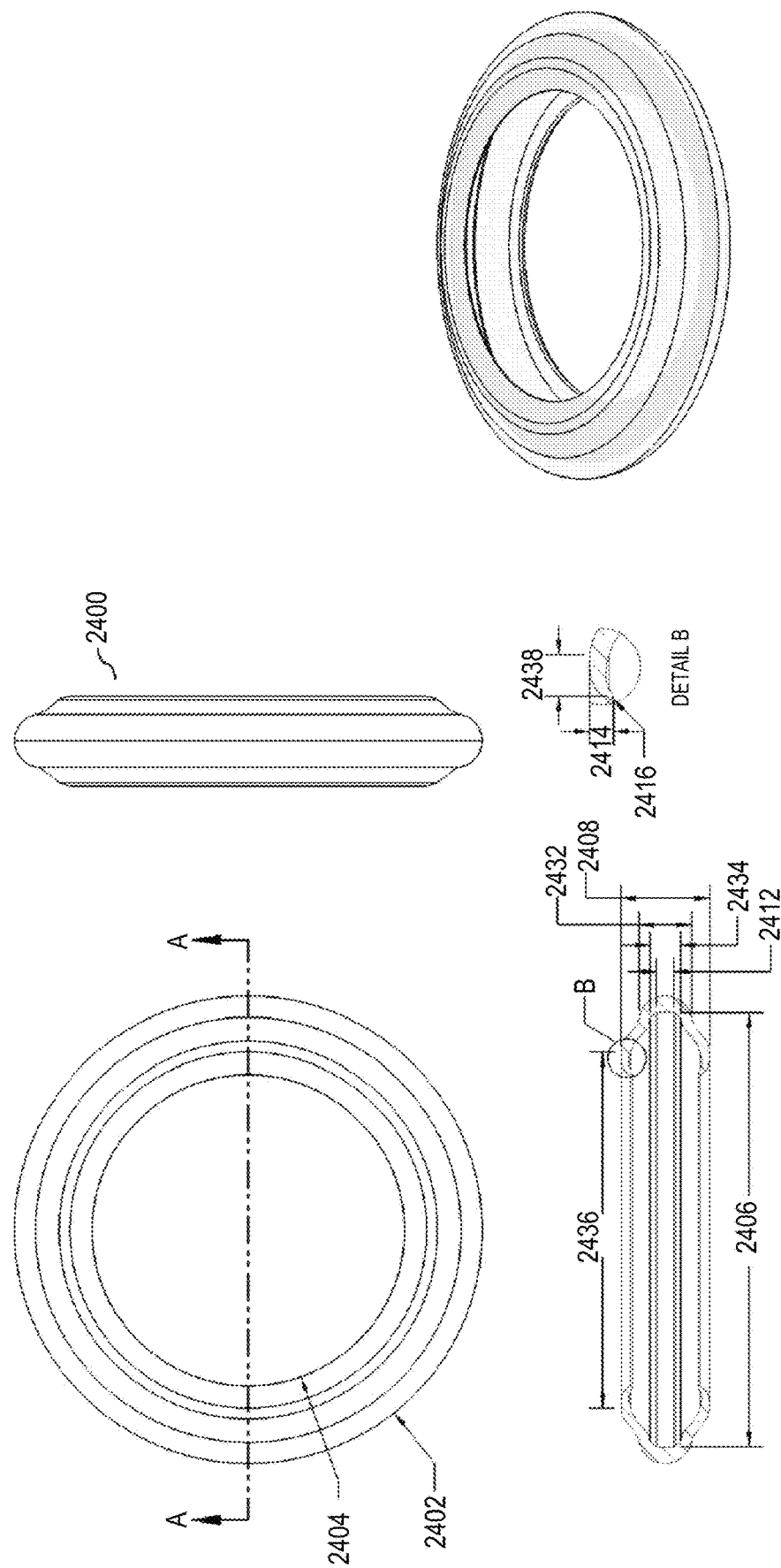
FIG. 24 illustrates another example prosthetic capsular device according to some embodiments herein.

FIG. 24 illustrates another example prosthetic capsular device according to some embodiments herein. In device 2400 of FIG. 24, the sidewall at the anterior portion of the device 2400 and the sidewall at the posterior of the device 2400 may form a slot of the device 2400. In some embodiments, the device 2400 may comprise a rounded middle portion protruding laterally outward from the anterior portion and the posterior portion. In some embodiments, the rounded middle portion may comprise a middle portion length 2432, measured from the exterior of the device. In some embodiments, the middle portion length 2432 may be about 1.17 mm. In some embodiments, the rounded middle portion may comprise a middle portion interior length 2434, measuring on the interior of the device. In some embodiments, the middle portion interior length 2434 may be about 0.70 mm. Device 2400 may comprise a slot within the device cavity configured to secure an intraocular lens therein.

In some embodiments, a length of a major axis of the device 2400 or a length measured from the outermost end of one sidewall to the outermost end of another sidewall along a major axis of the device 2400 can be about 10.50 mm. In other embodiments, the length of the major axis of the device 2400 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2400 may comprise a diameter 2402 of the device 2400.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2404, which can be a diameter of an anterior opening and/or a posterior opening. In some embodiments, the device may comprise a rim diameter 2436 comprising the diameter of the device formed by a rim surrounding the anterior opening and the posterior opening. In some embodiments, the rim diameter 2436 may measure between about 5.0 mm to about 15.0 mm. In some embodiments, the rim diameter 2436 may be about 8.0 mm. In some embodiments, the rim may comprise a rim length comprising a distance from the opening to a sidewall of the device. In some embodiments, the rim length may be about 0.1 mm to about 1.0 mm. In some embodiments, the rim length may be about 0.46 mm.

In some embodiments, the taper length 2414 may comprise a distance between the exterior surface of the sidewall at its most anterior/posterior point and the exterior surface at the anterior/posterior opening. In some embodiments, the exterior surface may comprise curved surfaces 2422 and 2416 at the slot and the openings, respectively. The curved shape of the sidewalls may contribute to a reduction in post-surgical complications through minimization of contact or the severity of contact between the device 2400 and the iris. The curved shape of the sidewall of the device 2400 near the openings is shown in Detail B.

In some embodiments, the device 2400 may comprise an inner diameter 2406 comprising the distance between the interior surfaces of the sidewalls at the ridge. In some embodiments, the inner diameter 2406 may about 9.75 mm. In some embodiments, the interior diameter may be between about 5.00 mm and 15.00 mm.

In some embodiments, the device 2400 may comprise a slot thickness 2412 comprising the size of the slot. In some embodiments, the slot thickness 2412 may be about 0.40 mm. In some embodiments, the slot thickness 2412 may between about 0.10 mm and about 2.00 mm. In some embodiments, the slot thickness may be configured to reduce the possibility of lens tilt by an intraocular lens located in the slot.

In some embodiments, a thickness 2408 of the device 2400 may comprise a maximum distance between the anterior side and posterior side of the device 2400. In some embodiments, the thickness 2408 of the device 2400 may be about 2.00 mm. In some embodiments, the thickness 2408 of the device 2400 may be between about 0.5 mm and 4.0 mm. In some embodiments, the thickness 2408 of the device 2400 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 25:
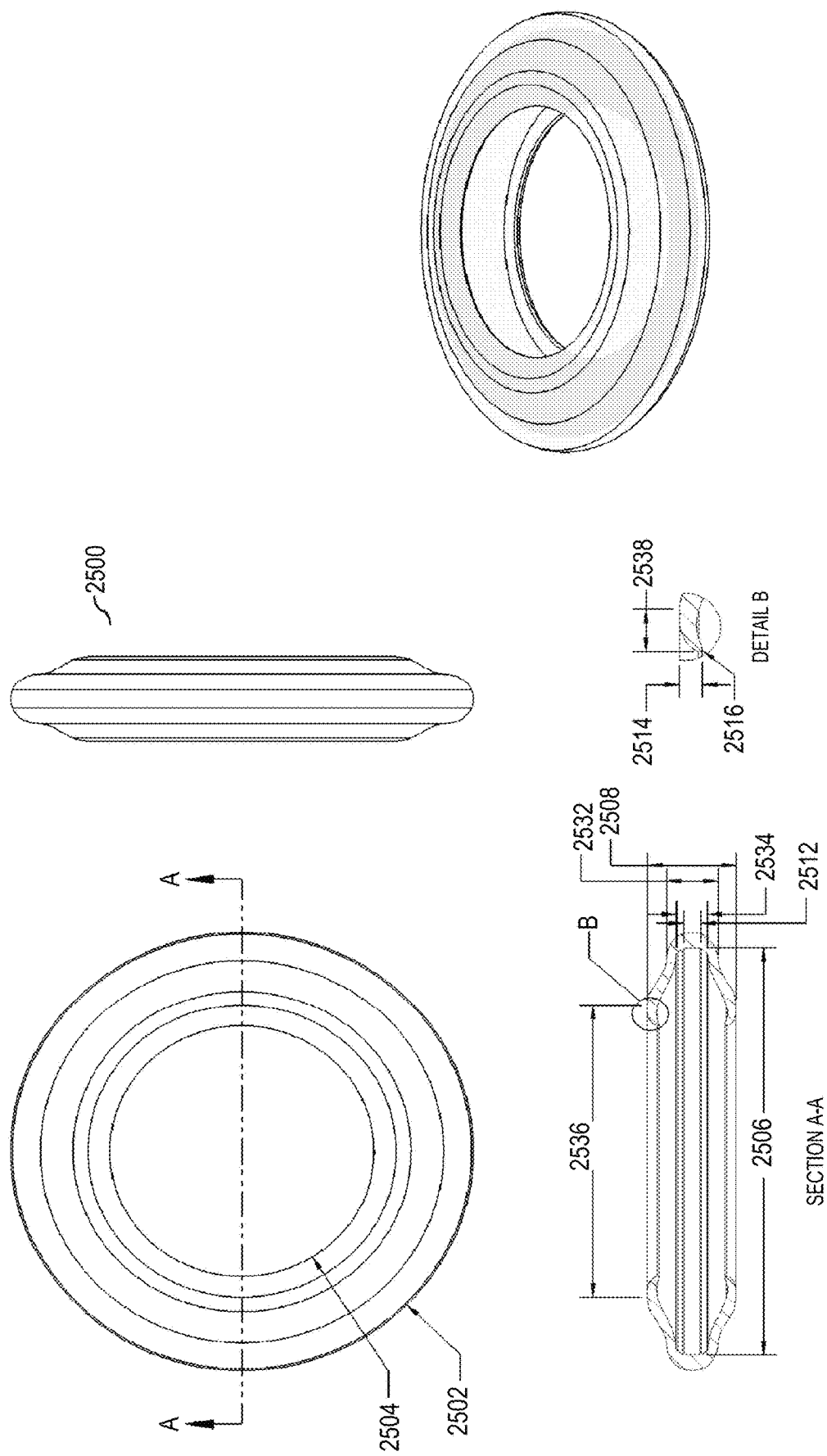
FIG. 25 illustrates another example prosthetic capsular device according to some embodiments herein.

FIG. 25 illustrates another example prosthetic capsular device according to some embodiments herein. In device 2500 of FIG. 25, the sidewall at the anterior portion of the device 2500 and the sidewall at the posterior of the device 2500 may form a slot of the device 2500. In some embodiments, the device 2500 may comprise a rounded middle portion protruding laterally outward from the anterior portion and the posterior portion. In some embodiments, the rounded middle portion may comprise a middle portion length 2532, measured from the exterior of the device. In some embodiments, the middle portion length 2532 may be about 1.17 mm. In some embodiments, the rounded middle portion may comprise a middle portion interior length 2534, measuring on the interior of the device. In some embodiments, the middle portion interior length 2534 may be about 0.70 mm. Device 2500 may comprise a slot within the device cavity configured to secure an intraocular lens therein.

In some embodiments, a length of a major axis of the device 2500 or a length measured from the outermost end of one sidewall to the outermost end of another sidewall along a major axis of the device 2500 can be about 10.50 mm. In other embodiments, the length of the major axis of the device 2500 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2500 may comprise a diameter 2502 of the device 2500.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2504, which can be a diameter of an anterior opening and/or a posterior opening. In some embodiments, the device may comprise a rim diameter 2536 comprising the diameter of the device formed by a rim surrounding the anterior opening and the posterior opening. In some embodiments, the rim diameter 2536 may measure between about 5.0 mm to about 15.0 mm. In some embodiments, the rim diameter 2536 may be about 7.0 mm. In some embodiments, the rim may comprise a rim length comprising a distance from the opening to a sidewall of the device. In some embodiments, the rim length may be about 0.1 mm to about 1.0 mm. In some embodiments, the rim length may be about 0.50 mm.

In some embodiments, the taper length 2514 may comprise a distance between the exterior surface of the sidewall at its most anterior/posterior point and the exterior surface at the anterior/posterior opening. In some embodiments, the exterior surface may comprise curved surfaces 2516 at the openings. The curved shape of the sidewalls may contribute to a reduction in post-surgical complications through minimization of contact or the severity of contact between the device 2500 and the iris. The curved shape of the sidewall of the device 2500 near the openings is shown in Detail B.

In some embodiments, the device 2500 may comprise an inner diameter 2506 comprising the distance between the interior surfaces of the sidewalls at the ridge. In some embodiments, the inner diameter 2506 may about 9.75 mm. In some embodiments, the interior diameter may be between about 5.00 mm and 15.00 mm.

In some embodiments, the device 2500 may comprise a slot thickness 2512 comprising the size of the slot. In some embodiments, the slot thickness 2512 may be about 0.40 mm. In some embodiments, the slot thickness 2512 may between about 0.10 mm and about 2.00 mm. In some embodiments, the slot thickness may be configured to reduce the possibility of lens tilt by an intraocular lens located in the slot.

In some embodiments, a thickness 2508 of the device 2500 may comprise a maximum distance between the anterior side and posterior side of the device 2500. In some embodiments, the thickness 2508 of the device 2500 may be about 2.00 mm. In some embodiments, the thickness 2508 of the device 2500 may be between about 0.5 mm and 4.0 mm. In some embodiments, the thickness 2508 of the device 2500 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 26:
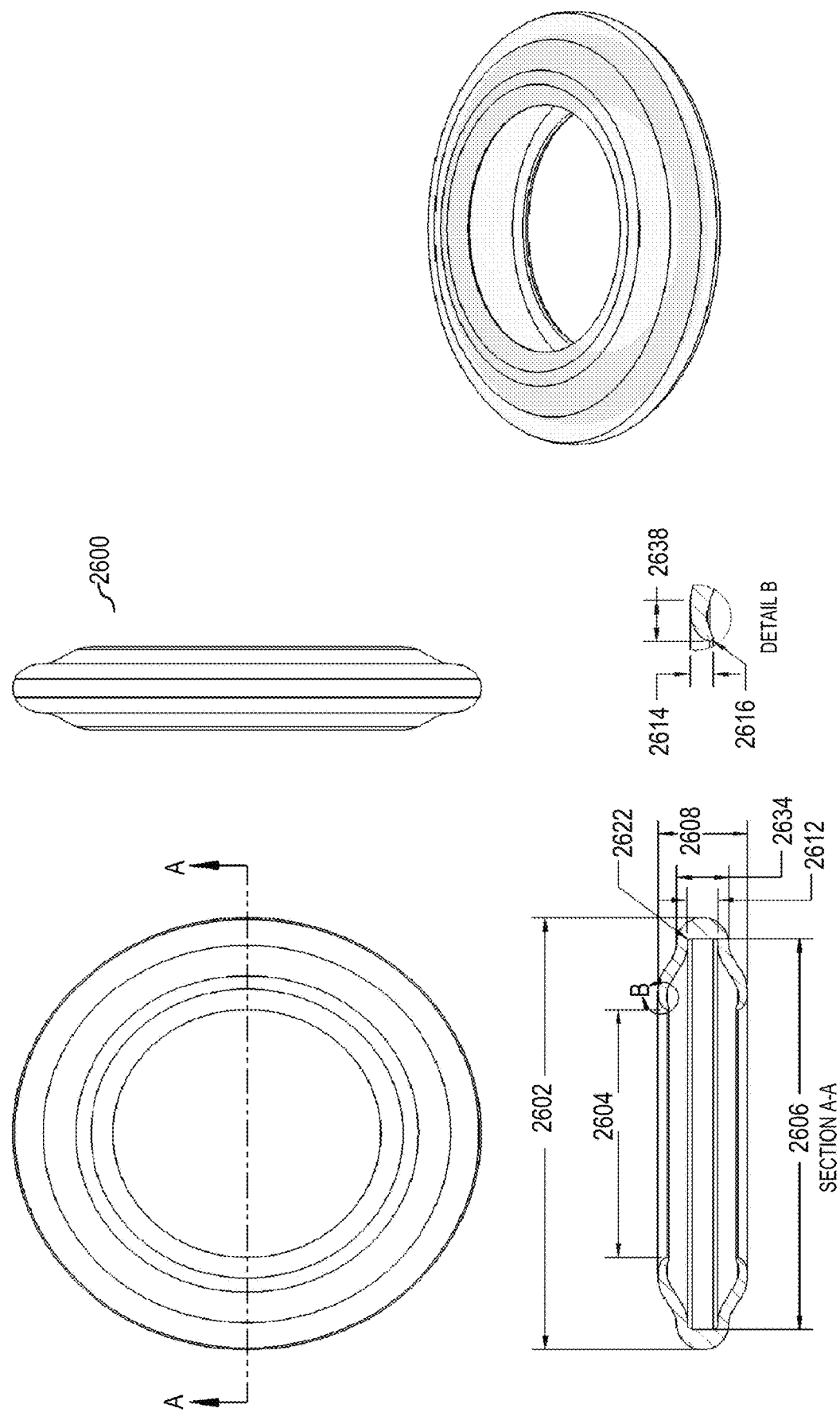
FIG. 26 illustrates another example prosthetic capsular device according to some embodiments herein.

FIG. 26 illustrates another example prosthetic capsular device according to some embodiments herein. In device 2600 of FIG. 26, the sidewall at the anterior portion of the device 2600 and the sidewall at the posterior of the device 2600 may form a slot of the device 2600. In some embodiments, the device 2600 may comprise a rounded middle portion protruding laterally outward from the anterior portion and the posterior portion. In some embodiments, the rounded middle portion may comprise a middle portion interior length 2634, measuring on the interior of the device. In some embodiments, the middle portion interior length 2634 may be about 0.70 mm. Device 2600 may comprise a slot within the device cavity configured to secure an intraocular lens therein.

In some embodiments, a length of a major axis of the device 2600 or a length measured from the outermost end of one sidewall to the outermost end of another sidewall along a major axis of the device 2600 can be about 10.50 mm. In other embodiments, the length of the major axis of the device 2600 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2600 may comprise a diameter 2602 of the device 2600.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2604, which can be a diameter of an anterior opening and/or a posterior opening.

In some embodiments, the taper length 2614 may comprise a distance between the exterior surface of the sidewall at its most anterior/posterior point and the exterior surface at the anterior/posterior opening. In some embodiments, the exterior surface may comprise curved surfaces 2616 at the openings. The curved shape of the sidewalls may contribute to a reduction in post-surgical complications through minimization of contact or the severity of contact between the device 2600 and the iris. The curved shape of the sidewall of the device 2600 near the openings is shown in Detail B.

In some embodiments, the device 2600 may comprise an inner diameter 2606 comprising the distance between the interior surfaces of the sidewalls at the ridge. In some embodiments, the inner diameter 2606 may about 9.50 mm.

In some embodiments, the interior diameter may be between about 5.00 mm and 15.00 mm.

In some embodiments, the device 2600 may comprise a slot thickness 2612 comprising the size of the slot. In some embodiments, the slot thickness 2612 may be about 0.70 mm. In some embodiments, the slot thickness 2612 may between about 0.10 mm and about 2.00 mm. In some embodiments, the slot thickness may be configured to reduce the possibility of lens tilt by an intraocular lens located in the slot.

In some embodiments, a thickness 2608 of the device 2600 may comprise a maximum distance between the anterior side and posterior side of the device 2600. In some embodiments, the thickness 2608 of the device 2600 may be about 2.00 mm. In some embodiments, the thickness 2608 of the device 2600 may be between about 0.5 mm and 4.0 mm. In some embodiments, the thickness 2608 of the device 2600 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

FIG. 27 illustrates another example prosthetic capsular device according to some embodiments herein. In device 2700 of FIG. 27, the sidewall at the anterior portion of the device 2700 and the sidewall at the posterior of the device 2700 may comprise one or more cutouts 2742, opening the anterior portion and the posterior portion of the device 2700 to the interior cavity. In some embodiments, there may be 10 cutouts in the device 2700. However, the number and shape of the cutouts is not limited. In some embodiments, the cutouts 2742 may facilitate folding and expansion of the device or may allow for insertion of differently shaped or sized intraocular lenses.

In some embodiments, the cutouts 2742 may be substantially triangular with a rounded or blunted tip, wherein the tip comprises a radius. In some embodiments, the tip may comprise a radius of about 0.15 mm. In some embodiments, the tip may comprise a radius of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, and/or within a range defined by two of the aforementioned values. In some embodiments, each cutout 2742 may extend around the circular opening in sectors of about 36°, although the angle may depend on the number of cutouts 2742. In some embodiments, the diameter 2704 of the cutouts 2742, measured at the tips of the cutouts, may be about 6.97 mm.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2744, which can be a diameter of an anterior opening and/or a posterior opening.

Figure 28:
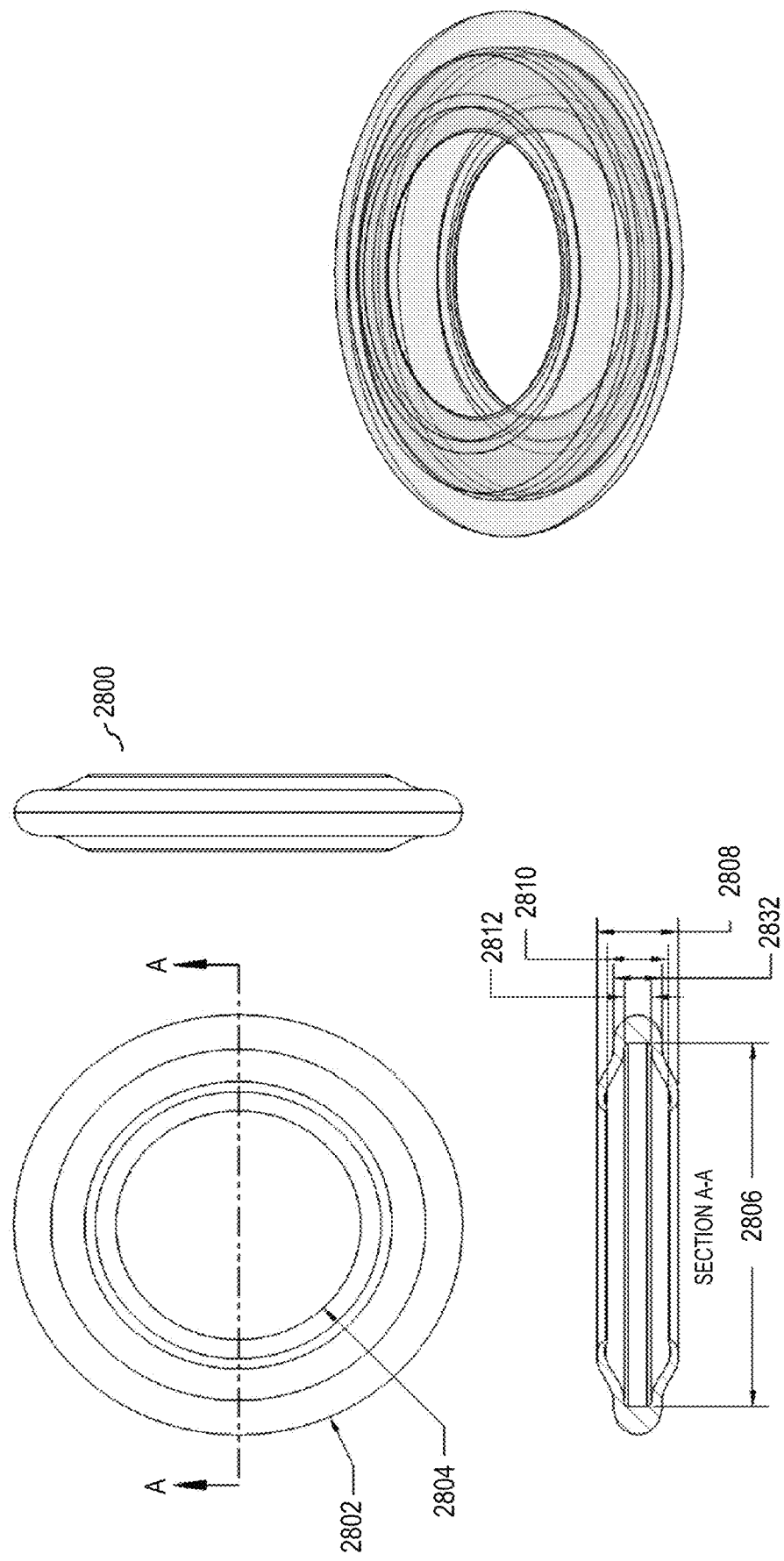
FIG. 28 illustrates another example prosthetic capsular device according to some embodiments herein.

FIG. 28 illustrates another example prosthetic capsular device according to some embodiments herein. In device 2800 of FIG. 28, the sidewall at the anterior portion of the device 2800 and the sidewall at the posterior of the device 2800 may form a slot of the device 2800. In some embodiments, the device 2800 may comprise a rounded middle portion protruding laterally outward from the anterior portion and the posterior portion. In some embodiments, the rounded middle portion may comprise a middle portion length 2832, measuring on the exterior of the device. In some embodiments, the middle portion length 2832 may be about 1.20 mm. Device 2800 may comprise a slot within the device cavity configured to secure an intraocular lens therein.

In some embodiments, a length of a major axis of the device 2800 or a length measured from the outermost end of one sidewall to the outermost end of another sidewall along a major axis of the device 2800 can be about 11.00 mm. In other embodiments, the length of the major axis of the device 2800 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2800 may comprise a diameter 2802 of the device 2800.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2804, which can be a diameter of an anterior opening and/or a posterior opening.

In some embodiments, the device 2800 may comprise an inner diameter 2806 comprising the distance between the interior surfaces of the sidewalls at the ridge. In some embodiments, the inner diameter 2806 may about 9.50 mm. In some embodiments, the interior diameter may be between about 5.00 mm and 15.00 mm.

In some embodiments, the device 2800 may comprise a slot thickness 2812 comprising the size of the slot. In some embodiments, the slot thickness 2812 may be about 0.67 mm. In some embodiments, the slot thickness 2812 may between about 0.10 mm and about 2.00 mm. In some embodiments, the slot thickness may be configured to reduce the possibility of lens tilt by an intraocular lens located in the slot.

In some embodiments, a thickness 2808 of the device 2800 may comprise a maximum distance between the anterior side and posterior side of the device 2800. In some embodiments, the thickness 2808 of the device 2800 may be about 2.00 mm. In some embodiments, the thickness 2808 of the device 2800 may be between about 0.5 mm and 4.0 mm. In some embodiments, the thickness 2808 of the device 2800 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the device 2800 may comprise an inner thickness 2810 comprising a distance between an inner surface of the sidewall at the anterior opening and an inner surface of the sidewall at the posterior opening. In some embodiments, the inner thickness 2810 may be about 1.48 mm.

Figure 29:
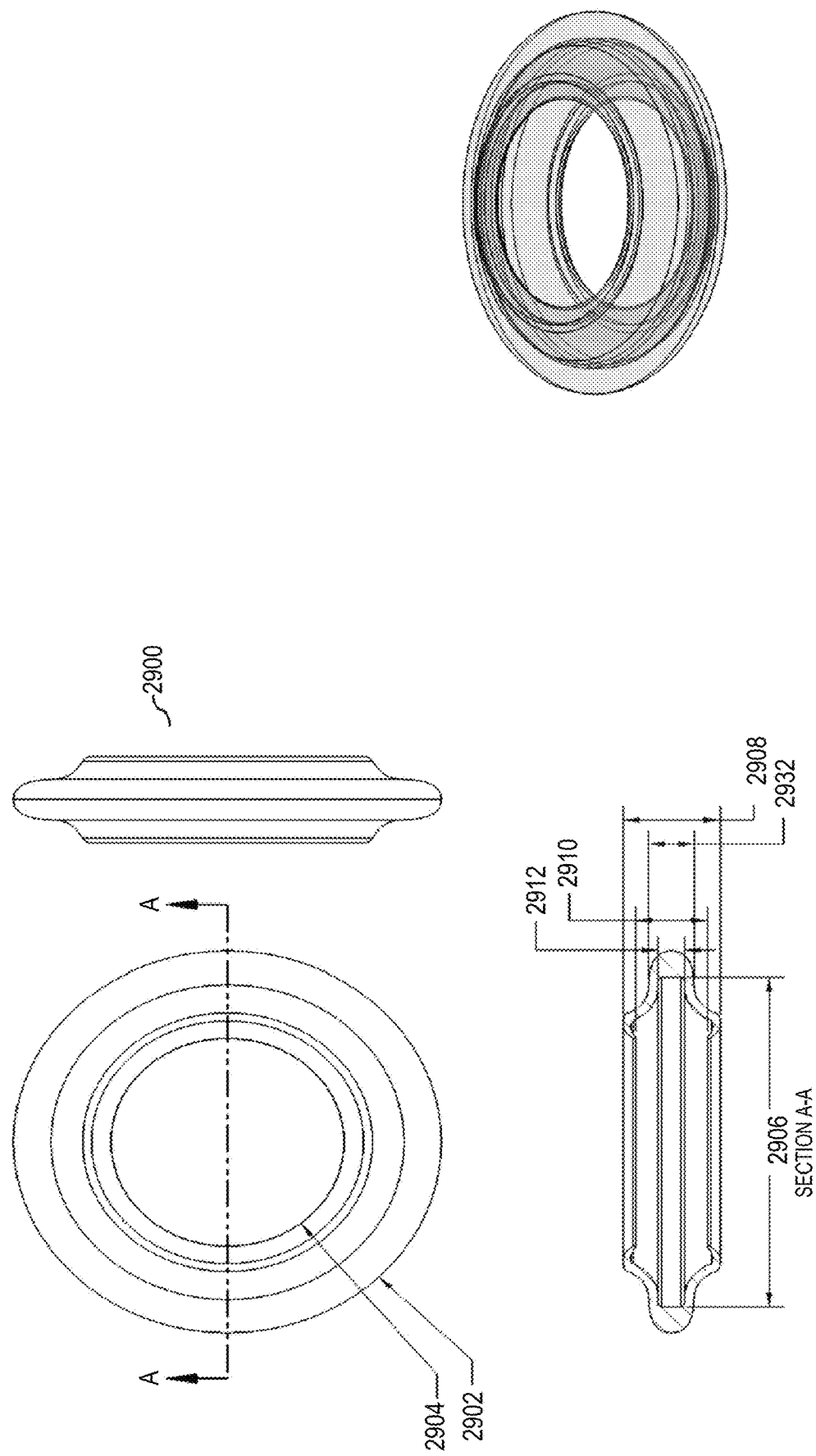
FIG. 29 illustrates another example prosthetic capsular device according to some embodiments herein.

FIG. 29 illustrates another example prosthetic capsular device according to some embodiments herein. In device 2900 of FIG. 29, the sidewall at the anterior portion of the device 2900 and the sidewall at the posterior of the device 2900 may form a slot of the device 2900. In some embodiments, the device 2900 may comprise a rounded middle portion protruding laterally outward from the anterior portion and the posterior portion. In some embodiments, the rounded middle portion may comprise a middle portion length 2932, measuring on the exterior of the device. In some embodiments, the middle portion length 2932 may be about 1.17 mm. Device 2900 may comprise a slot within the device cavity configured to secure an intraocular lens therein.

In some embodiments, a length of a major axis of the device 2900 or a length measured from the outermost end of one sidewall to the outermost end of another sidewall along a major axis of the device 2900 can be about 11.00 mm. In other embodiments, the length of the major axis of the device 2900 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 2900 may comprise a diameter 2902 of the device 2900.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 2904, which can be a diameter of an anterior opening and/or a posterior opening.

In some embodiments, the device 2900 may comprise an inner diameter 2906 comprising the distance between the interior surfaces of the sidewalls at the ridge. In some embodiments, the inner diameter 2906 may about 9.50 mm. In some embodiments, the interior diameter may be between about 5.00 mm and 15.00 mm.

In some embodiments, the device 2900 may comprise a slot thickness 2912 comprising the size of the slot. In some embodiments, the slot thickness 2912 may be about 0.67 mm. In some embodiments, the slot thickness 2912 may between about 0.10 mm and about 2.00 mm. In some embodiments, the slot thickness may be configured to reduce the possibility of lens tilt by an intraocular lens located in the slot.

In some embodiments, a thickness 2908 of the device 2900 may comprise a maximum distance between the anterior side and posterior side of the device 2900. In some embodiments, the thickness 2908 of the device 2900 may be about 2.50 mm. In some embodiments, the thickness 2908 of the device 2900 may be between about 0.5 mm and 4.0 mm. In some embodiments, the thickness 2908 of the device 2900 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

In some embodiments, the device 2900 may comprise an inner thickness 2910 comprising a distance between an inner surface of the sidewall at the anterior opening and an inner surface of the sidewall at the posterior opening. In some embodiments, the inner thickness 2910 may be about 1.85 mm.

Figure 30:
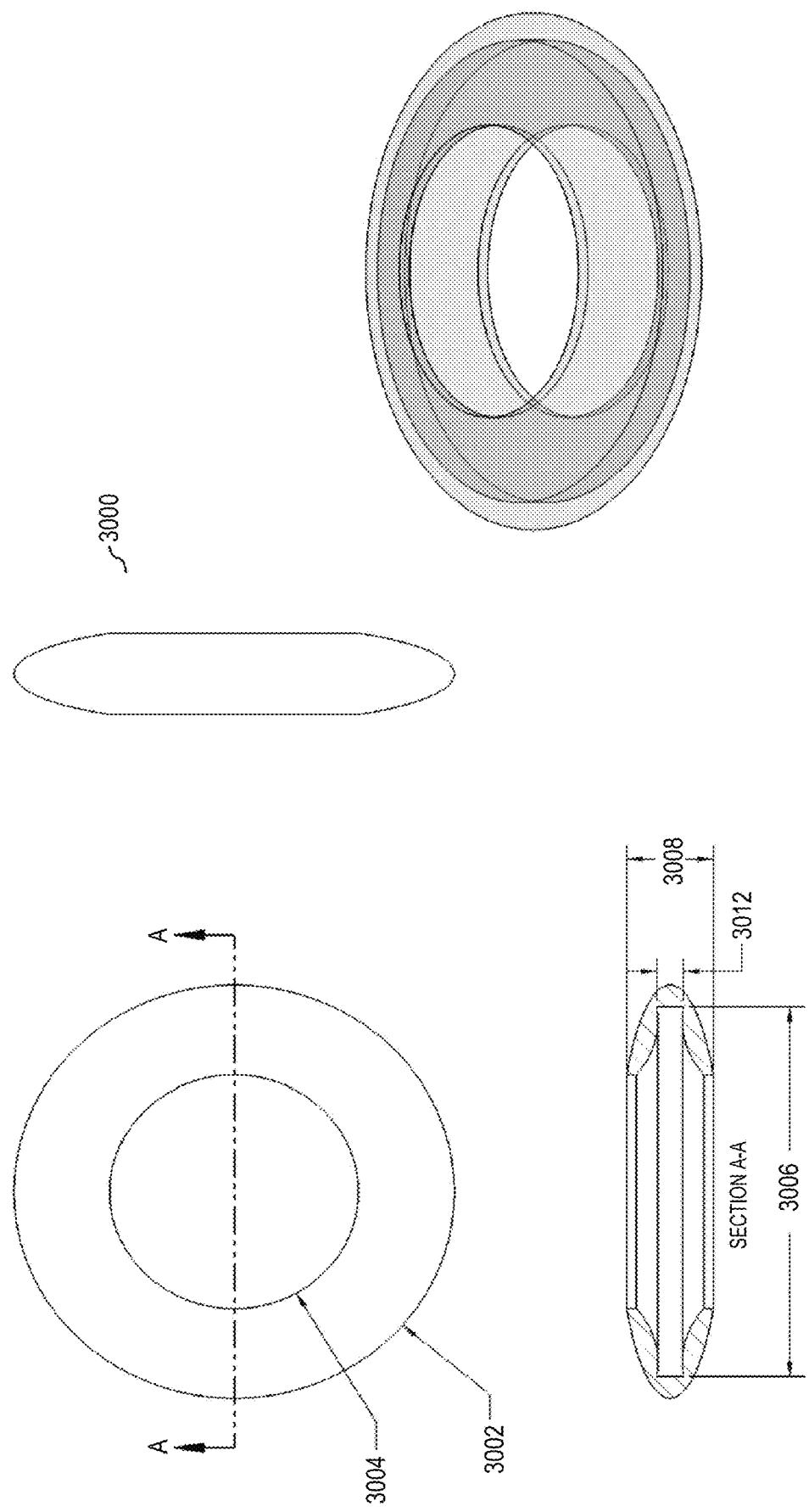
FIG. 30 illustrates another example prosthetic capsular device according to some embodiments herein.

FIG. 30 illustrates another example prosthetic capsular device according to some embodiments herein. In device 3000 of FIG. 30, the sidewall at the anterior portion of the device 3000 and the sidewall at the posterior of the device 3000 may form a slot of the device 3000. In some embodiments, the device 3000 a completely curved exterior surface, such that the device 3000 is disk-shaped.

In some embodiments, a length of a major axis of the device 3000 or a length measured from the outermost end of one sidewall to the outermost end of another sidewall along a major axis of the device 3000 can be about 11.50 mm. In other embodiments, the length of the major axis of the device 3000 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values. In some embodiments, the length of the major axis of the device 3000 may comprise a diameter 3002 of the device 3000.

In certain embodiments, the width of an opening of the cavity formed by each end of the two sidewalls can be about 5.00 mm. In certain embodiments, the width of an opening of the cavity formed by each end of the two sidewalls can be about 6.00 mm. In some embodiments, the width of the opening of the cavity formed by each end of the two sidewalls can be about 7.0 mm. In some embodiments, the width of the opening of the cavity formed by each end of the two sidewalls can be about 3.0 mm, about 3.2 mm, about 3.4 mm, about 3.6 mm, about 3.8 mm, about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values. In some embodiments, the width of the opening of the cavity formed by each end of the two sidewalls may comprise an opening diameter 3004, which can be a diameter of an anterior opening and/or a posterior opening.

In some embodiments, the device 3000 may comprise an inner diameter 3006 comprising the distance between the interior surfaces of the sidewalls at the ridge. In some embodiments, the inner diameter 3006 may about 10.30 mm. In some embodiments, the interior diameter may be between about 5.00 mm and 15.00 mm.

In some embodiments, the device 3000 may comprise a slot thickness 3012 comprising the size of the slot. In some embodiments, the slot thickness 3012 may be about 0.70 mm. In some embodiments, the slot thickness 3012 may between about 0.10 mm and about 2.00 mm. In some embodiments, the slot thickness may be configured to reduce the possibility of lens tilt by an intraocular lens located in the slot.

In some embodiments, a thickness 3008 of the device 3000 may comprise a maximum distance between the anterior side and posterior side of the device 3000. In some embodiments, the thickness 3008 of the device 3000 may be about 2.27 mm. In some embodiments, the thickness 3008 of the device 3000 may be between about 0.5 mm and 4.0 mm. In some embodiments, the thickness 3008 of the device 3000 may about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, or any value between the aforementioned values.

Figure 31:
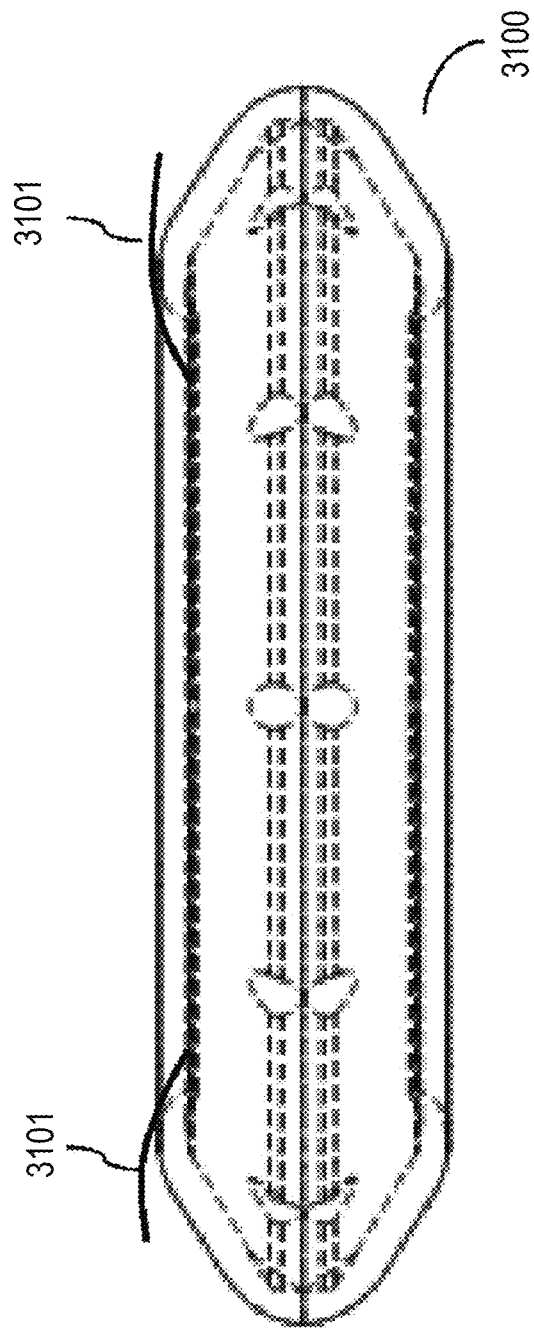
FIG. 31 Illustrates an example diagram of the interaction between a prosthetic capsular device and an iris of the eye.

FIG. 31 illustrates an example of the interaction between the curved section of the sidewall and the iris of the eye. The curved section of the sidewalls may form a concavity in the sidewalls that reduce the amount and/or severity of contact between the device 3100 and posterior of the iris 3101. In some embodiments, the smoother contact between the device 3100 and the posterior of the iris 3101 may reduce or eliminate pigment dispersion and/or inflammation that can be caused using other devices. In some embodiments, at least a portion of an external surface of the sidewalls of the devices herein may be curved, while at least of portion of an interior surface of the sidewalls may be straight. In some embodiments, the device 3100 may correspond to device 100 or any of the prosthetic capsular devices shown in the Figures. For example, the exterior surface of device 3100 may correspond to the exterior surface of device 100.

Figure 32:
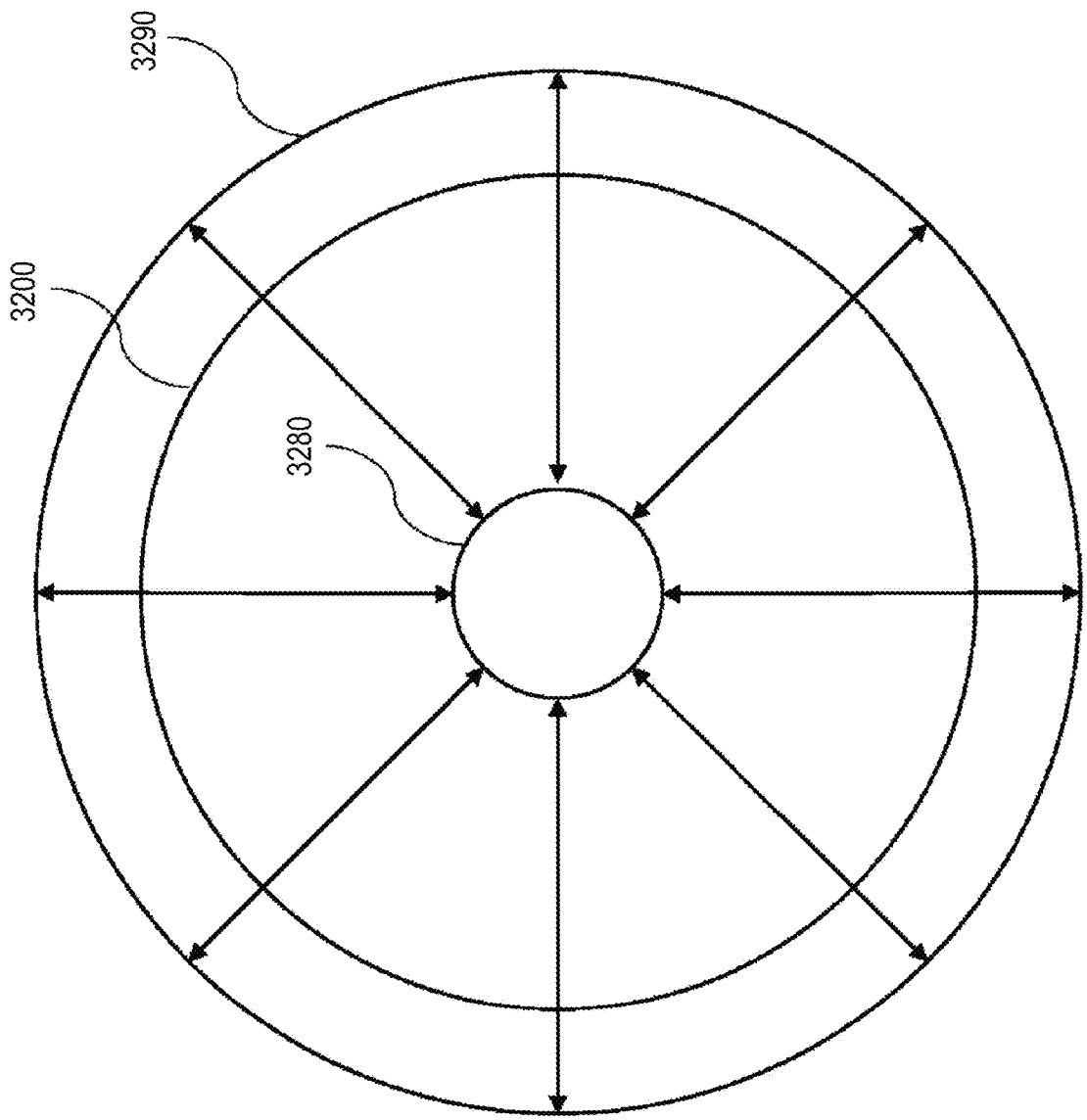
FIG. 32 illustrates an example diagram of a prosthetic capsular device within an eye.

FIG. 32 illustrates an example diagram of a prosthetic capsular device within an eye. The prosthetic capsular device 3200 may comprise any of the devices described herein. The diagram illustrates an eye with a dilated pupil 3290 and with a contracted pupil 3280. As the pupil contracts and dilates when viewing objects, the posterior surface of the iris may contact the device 3200. In some embodiments, the shape, size, and tapered surfaces of the devices described herein may reduce or mitigate the severity of the contact between the iris and the device. As a result, postsurgical complications may be minimized.

Figure 33:
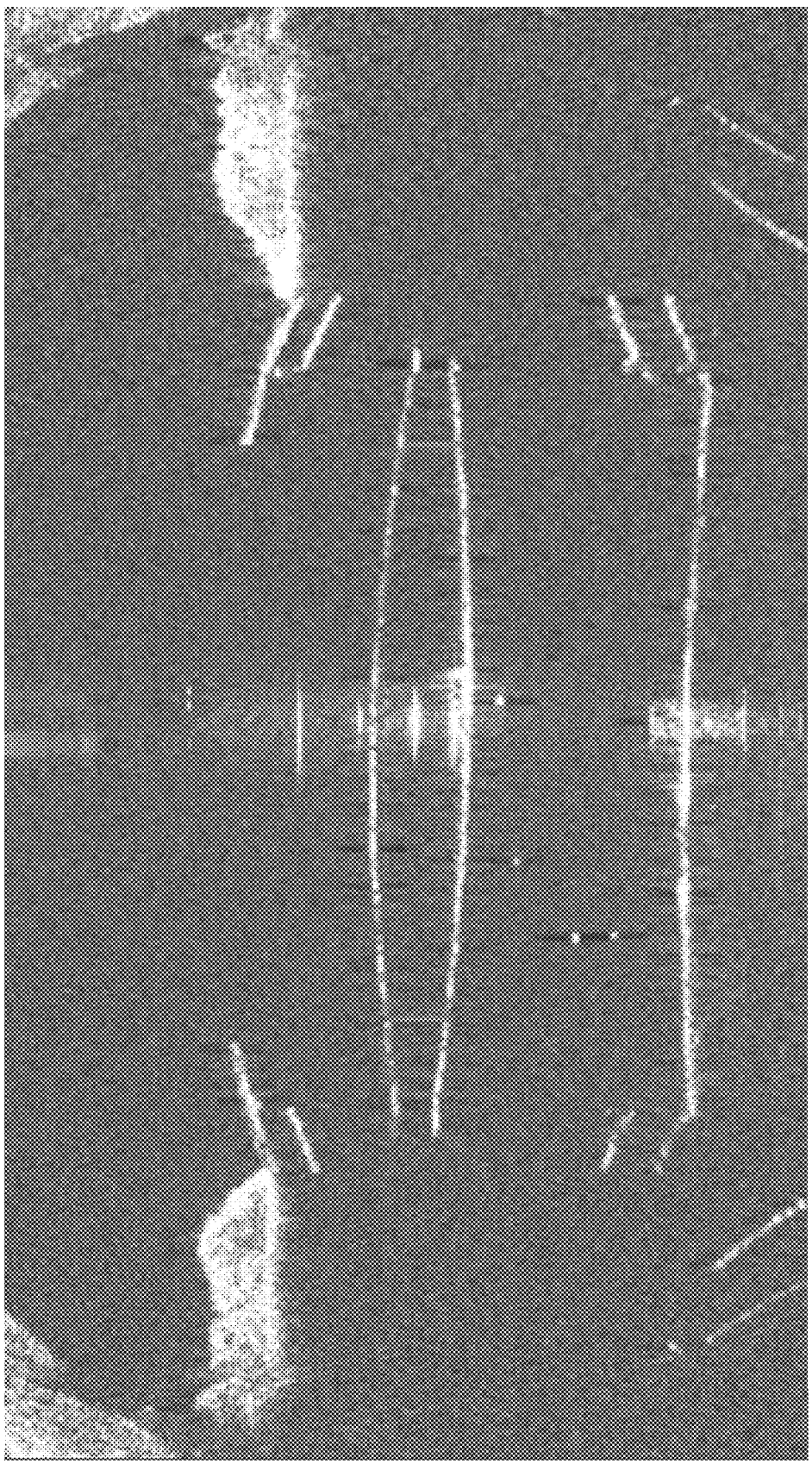
FIG. 33 illustrates an example image of a prosthetic capsular device within an eye according to some embodiments herein.

FIG. 33 illustrates an example image of a prosthetic capsular device within an eye. The prosthetic capsular device may comprise device 100 or any of the other prosthetic capsular devices shown in the Figures.

Figure 34:
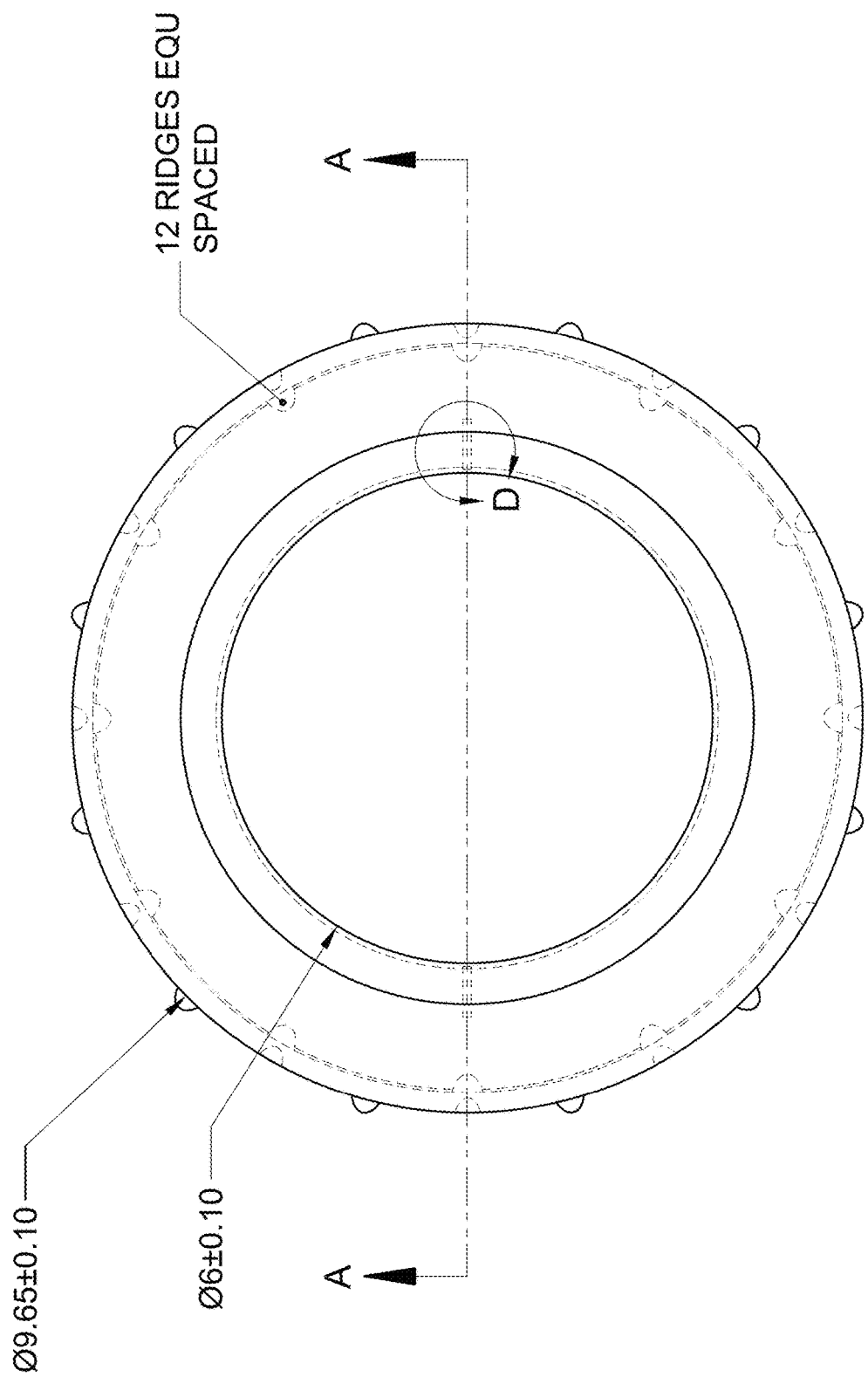
FIG. 34 illustrates another example prosthetic device according to some embodiments herein.

FIG. 34 illustrates another example prosthetic device according to some embodiments herein. The device of FIG. 34 may comprise some or all of the features described with respect to the devices of FIGS. 1-33. In some embodiments, the prosthetic capsular device may comprise one of more tabs, notches, or ribs on an interior surface of the device. In some embodiments, the one of more tabs, notches, or ribs on an interior surface of the device may project inwardly, into the central cavity of the device. In some embodiments, the one or more tabs, notches, or ribs on an interior surface of the device may be configured to couple, contact, join, or otherwise interact with an IOL or haptics of an IOL. In some embodiments, the one or more tabs, notches, or ribs on an interior surface of the device may prevent rotation or translation of an IOL within the device. Preventing rotation of an IOL within the device may be particularly important in cases in which a toric IOL is used, as the rotational position of the lens within the eye is significant to the functionality of the toric lens. The size, shape, location, and orientation of the one or more tabs, notches, or ribs on the interior surface of the device is not limited. Preferably, the one or more tabs, notches, or ribs on the interior surface of the device may be located such that they may couple, contact, join, or otherwise interact with an IOL or haptics of an IOL.

In some embodiments, in addition to the one or more tabs, notches, or ribs on an interior surface of the device, the prosthetic capsular device may comprise one or more tabs, notches, or ribs on an exterior surface of the device, protruding radially outward from the exterior surface. In some embodiments, the one or more tabs, notches, or ribs on an exterior surface of the device may contact or engage a surface of the natural capsular bag. In some embodiments, this contact of the one or more tabs, notches, or ribs with the natural capsular bag may prevent or eliminate rotation of the prosthetic capsular device within the eye. Again, preventing rotation may be particularly important in the case in which a toric IOL is inserted within the prosthetic capsular device. The size, shape, location and orientation of the one or more tabs, notches, or ribs on the exterior surface of the device is not limited. However, in some embodiments, the one or more tabs, notches, or ribs on the exterior surface of the device may be located at a radially outward location, such as along a midpoint of the device along the longitudinal axis, such that the one or more tabs, notches, or ribs may contact the natural capsular bag.

Figure 35:
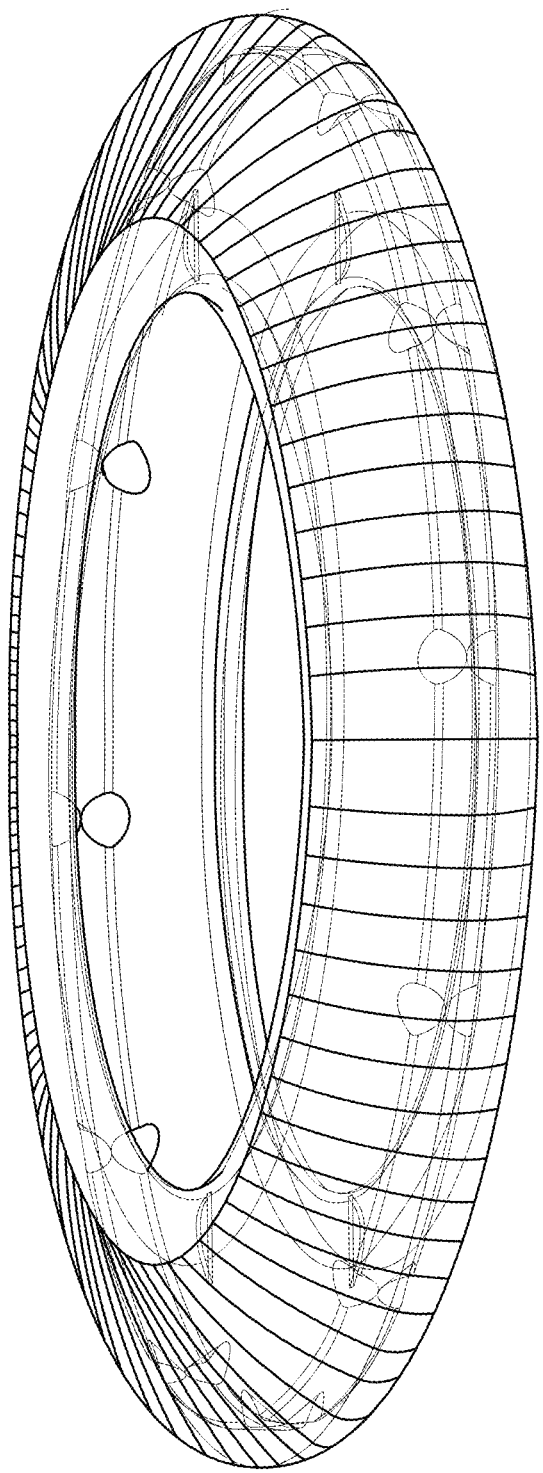
FIG. 35 illustrates another example prosthetic device according to some embodiments herein.

FIG. 35 illustrates another example prosthetic device according to some embodiments herein. In some embodiments, in addition to, or as an alternative to, the one or more tabs, notches, or ribs on the exterior surface of the device, the prosthetic capsular device may comprise one or more ridges extending along at least a portion of the exterior surface of the device. For example, as illustrated in FIG. 35, the one or more ridges may extend along the entirety of the device from an anterior opening to a posterior opening. However, in some embodiments, the ridges may extend only along a portion of the device in the longitudinal direction. Furthermore, although the one or more ridges are illustrated as being present around the entirety of the circumference of the exterior sidewall of the device, the one or more ridges may be present around only a portion of the circumference. As with the one or more tabs, notches, or ribs on the exterior surface of the device, the one or more ridges may contact a surface of the natural capsular bag to prevent rotation and/or translation of the prosthetic capsular device within the eye. In some embodiments, in addition to, or as an alternative to, the one or more tabs, notches, ribs, or ridges on the exterior surface of the device, the exterior surface of the device may comprises one or more textured surfaces. In some embodiments, a textured surface may provide enhanced grip or friction with the natural capsular bag, which may prevent or reduce translational or rotational movement of the device within the eye. In some embodiments, the textured surface may comprise an adhesive, nanostructures or micro-structures formed on the exterior surface, a separate material formed on the exterior surface, or may be formed using other methods known in the art.

Figure 36:
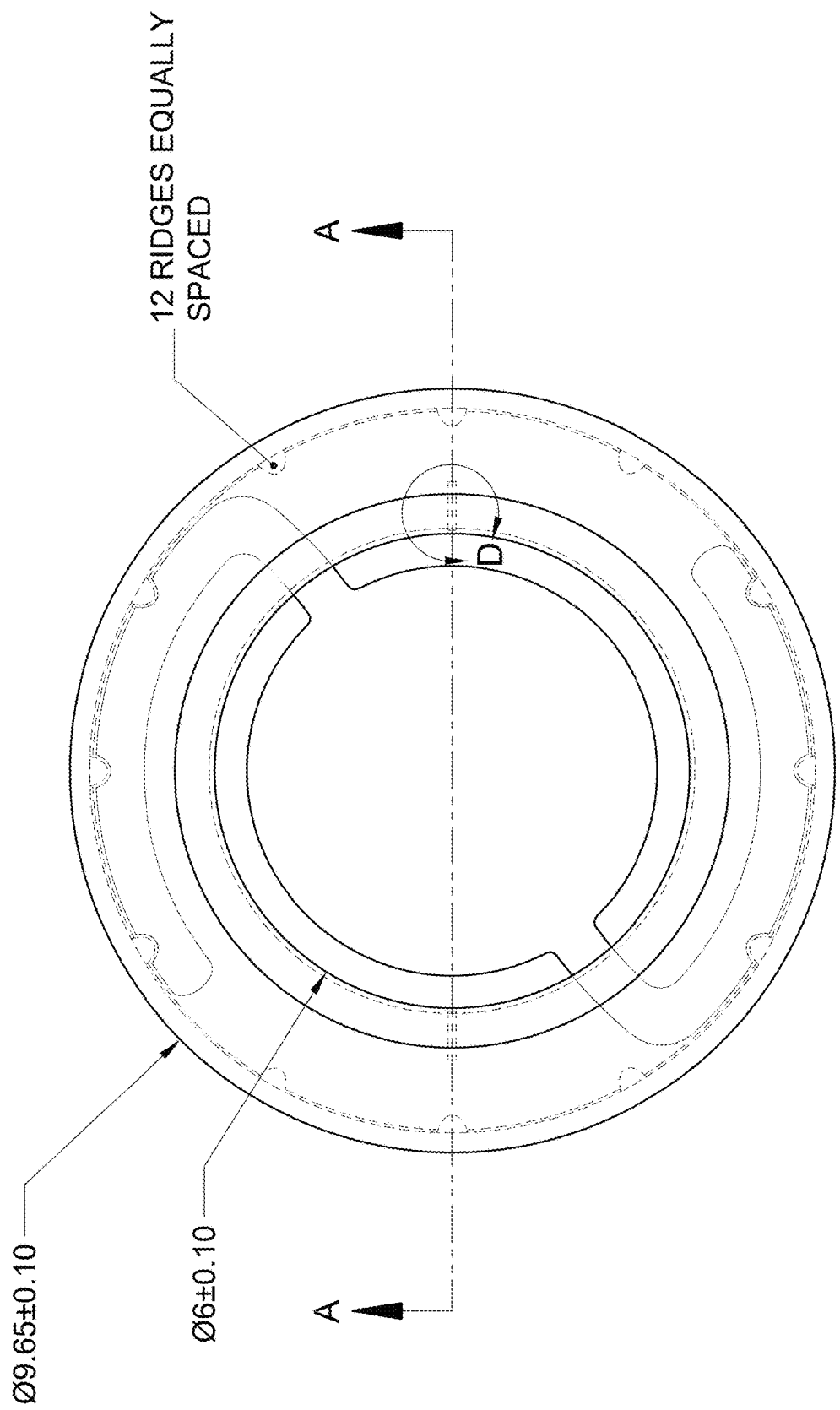
FIG. 36 illustrates another example prosthetic device and an example intraocular lens therein according to some embodiments herein.
Figure 37:
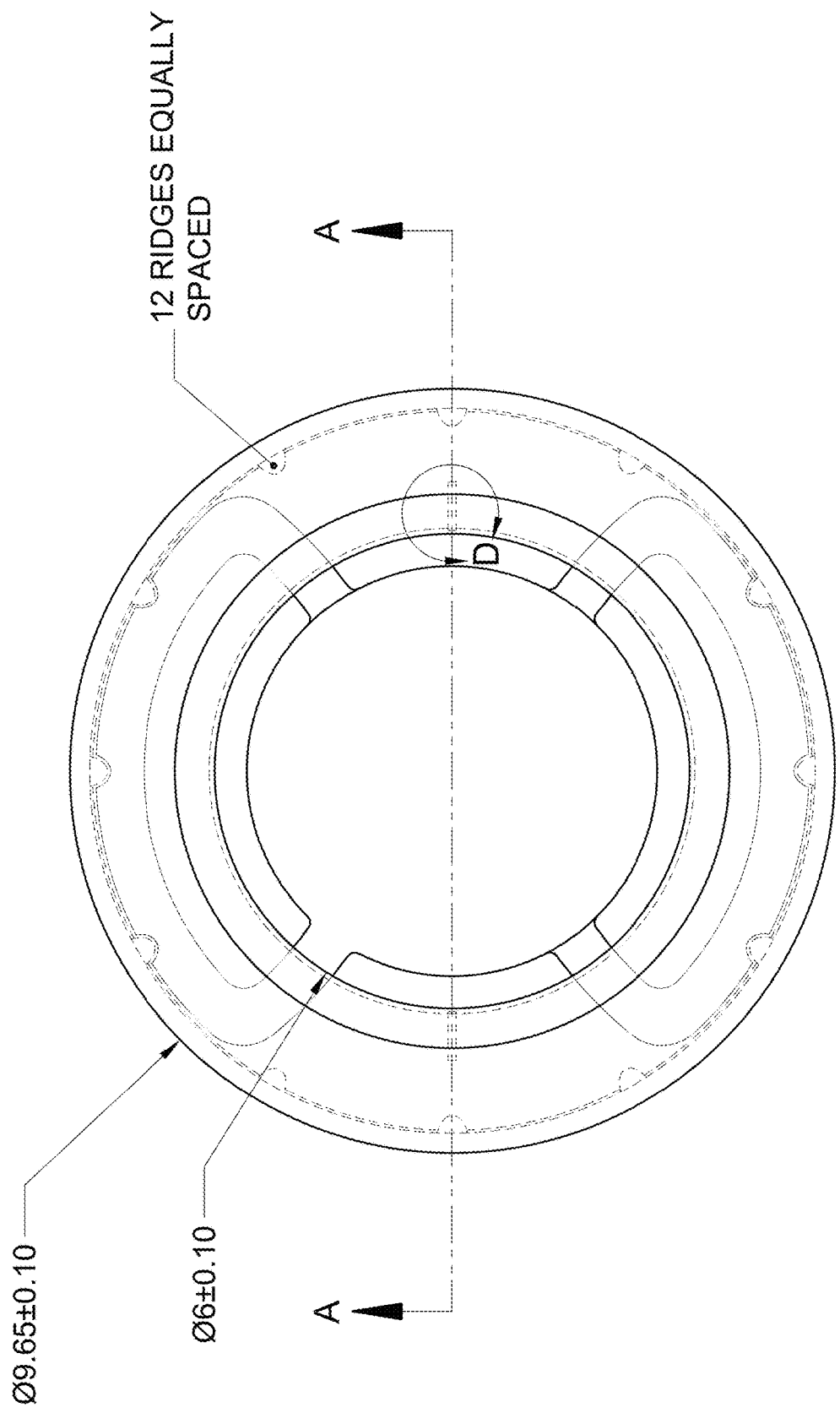
FIG. 37 illustrates another example prosthetic device and an example intraocular lens therein according to some embodiments herein.
Figure 38:
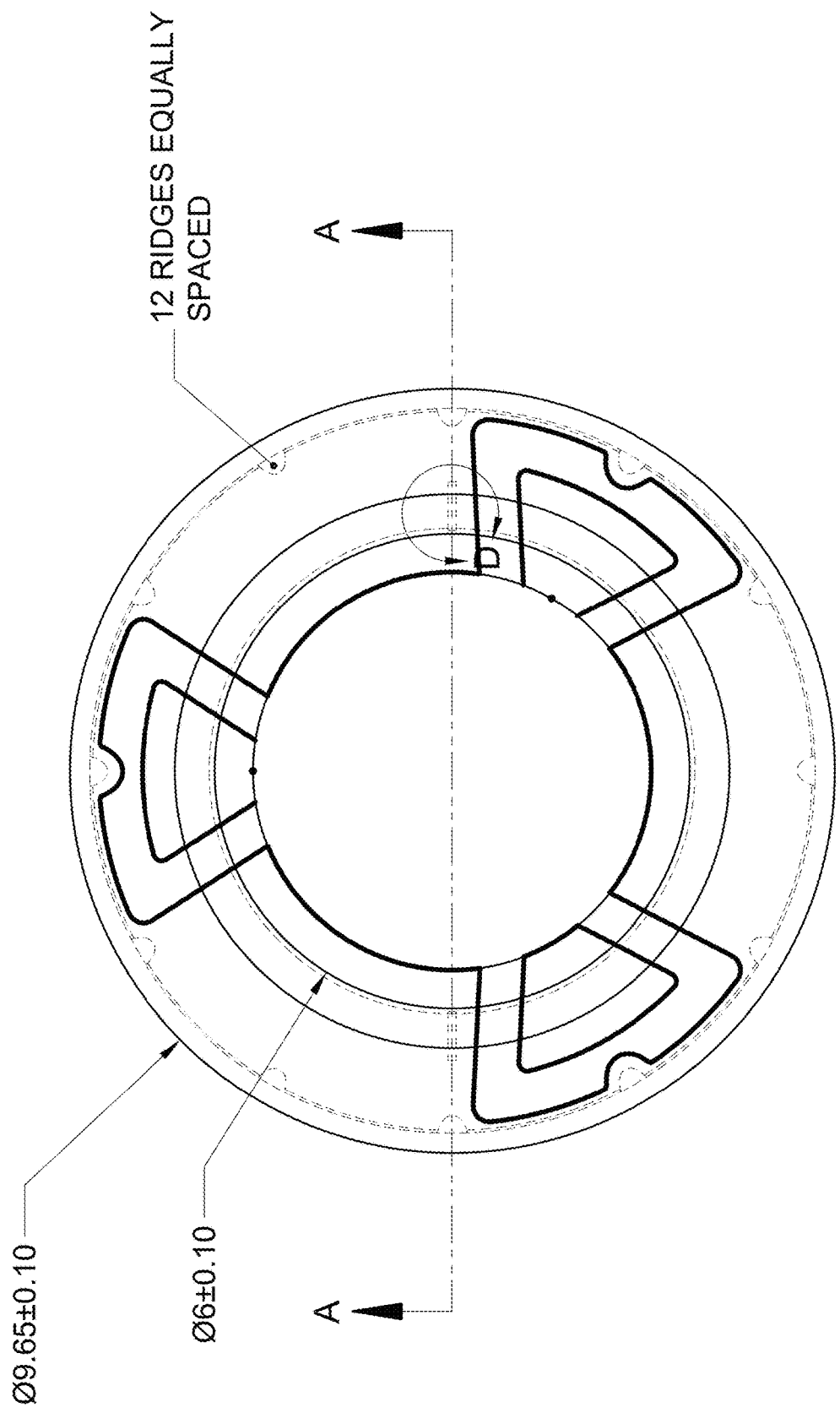
FIG. 38 illustrates another example prosthetic device and an example intraocular lens therein according to some embodiments herein.
Figure 39:
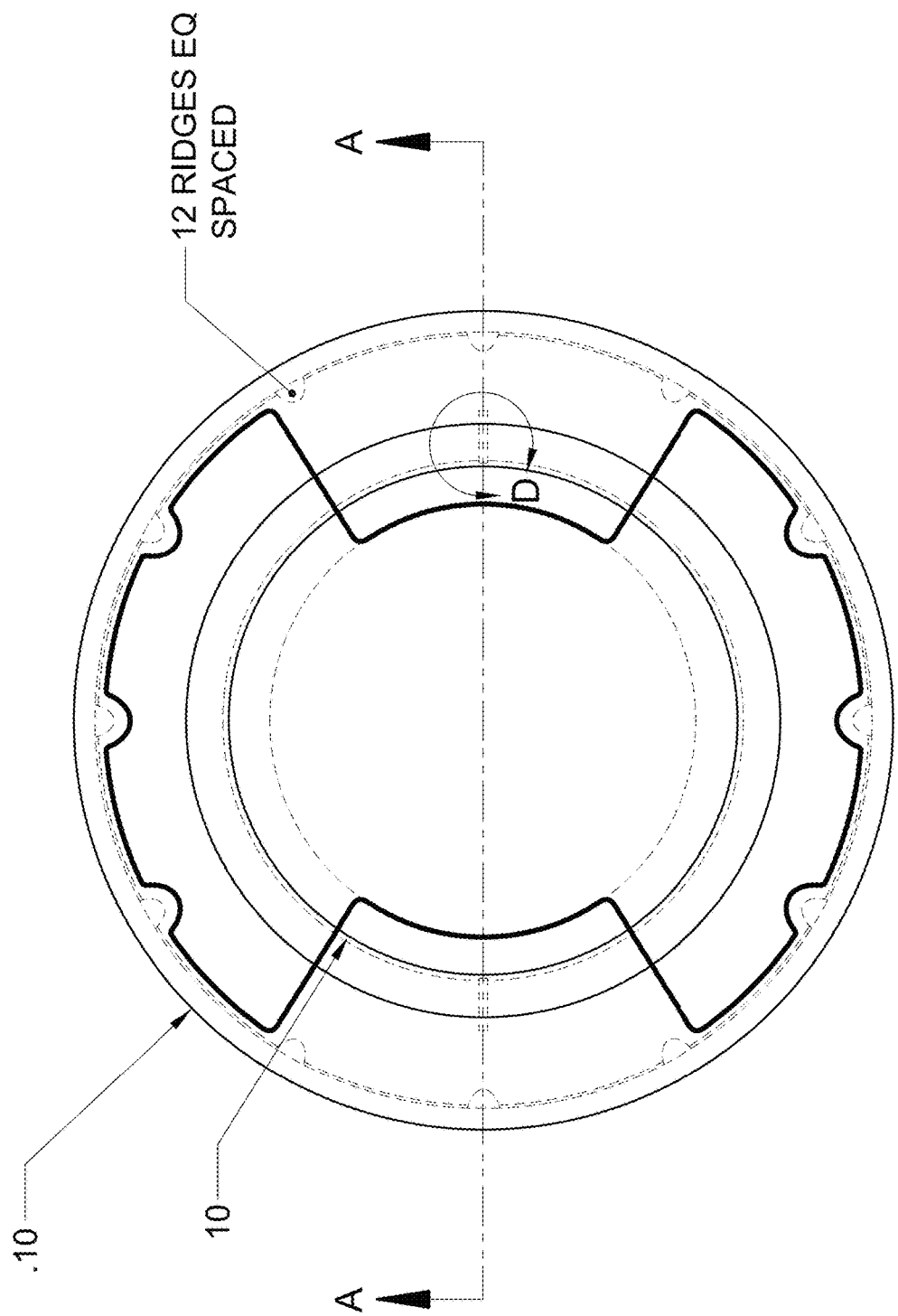
FIG. 39 illustrates another example prosthetic device and an example intraocular lens therein according to some embodiments herein.
Figure 40:
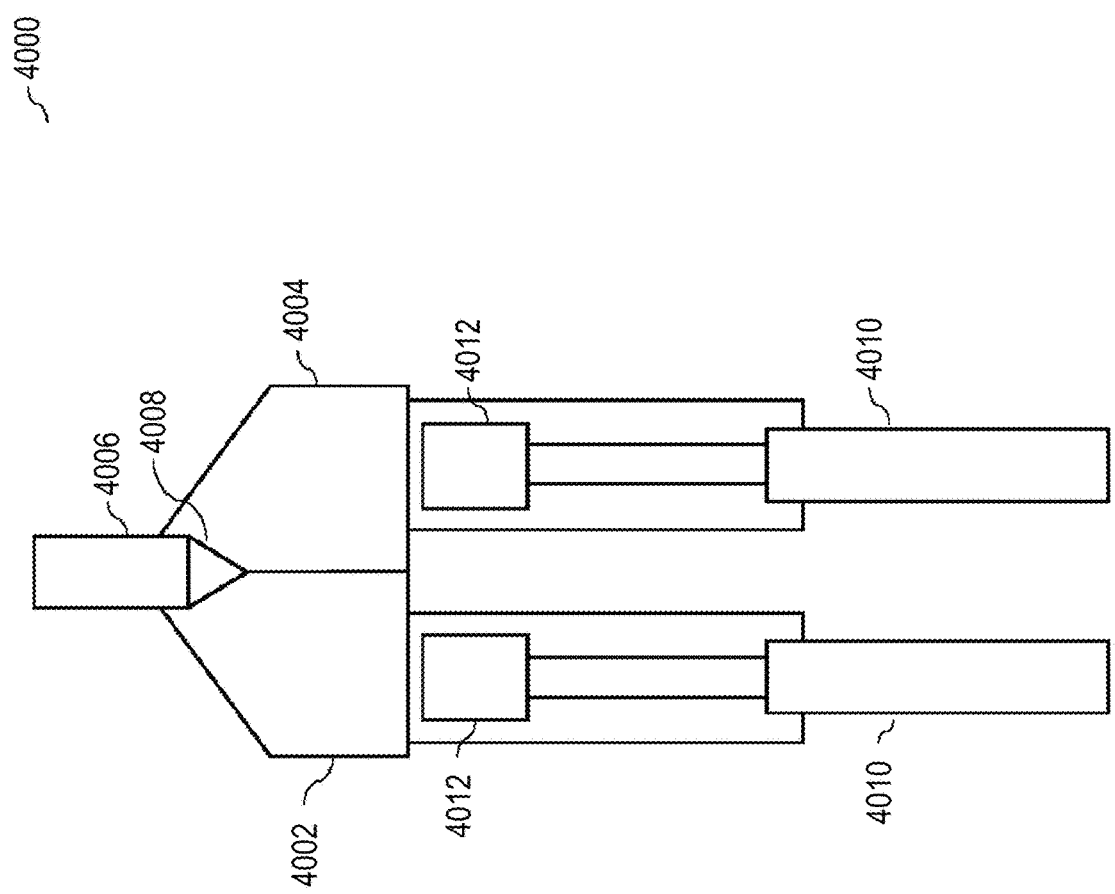
FIG. 40 illustrates an example injector cartridge for use in a method of inserting a prosthetic intraocular device and/or an intraocular lens according to some embodiments herein.

FIG. 36 illustrates another example prosthetic device and an example intraocular lens therein according to some embodiments herein. In particular, FIG. 36 illustrates a prosthetic implant device with an IOL implanted therein, wherein haptics of the IOL lock together with one or more tabs, notches, or ribs on an interior surface of the device within the cavity of the capsule. In some embodiments, one or more notches in the haptic or haptics of the IOL may couple, contact, join, or otherwise interact with the one or more tabs, notches, or ribs on an interior surface of the device. The shape, size, location, and orientation of IOLs and haptics that may be coupled to the one or more tabs, notches, or ribs on an interior surface of the device is not particularly limited. For the sake of example, additional IOLs and haptic shapes are illustrated in FIGS. 37-39. In some embodiments, disclosed herein are one or more "lock and key" kit configurations comprising a prosthetic capsular device and an IOL that couples to the one or more tabs, notches, or ribs on an interior surface of the device. FIG. 40 illustrates an example injector cartridge for use in a method of inserting a prosthetic intraocular device and/or an intraocular lens according to some embodiments herein.

Thus, some embodiments herein are directed to a kit for use in an ophthalmic surgical procedure, the kit comprising: a prosthetic implant device for insertion into a natural capsular bag of an eye after removal of a cataract, and an IOL. In some embodiments, the prosthetic implant device may comprise one or more tabs, notches, or ribs on an interior surface of the device, which are configured to couple, contact, join, or otherwise interact with one or more notches of the IOL or of haptics attached to the IOL.

FIG. 40 illustrates an example injector cartridge 4000 for use in a method of inserting a prosthetic intraocular device and/or an intraocular lens according to some embodiments herein. In some embodiments, during ocular surgical procedures, injector cartridges may be used to inject devices and/or IOLs into the eye. Existing injectors comprise single-use or reusable cartridges that facilitate insertion of an ophthalmic prosthetic device or IOL through a corneal incision of an eye. However, existing injectors have several drawbacks, including an inability to insert a prosthetic capsular device followed by an IOL, without removing the injector from the corneal insertion. For example, using existing injectors, a prosthetic capsular device may be inserted into the eye after removal of a cataract. After this insertion, the injector must be removed from the corneal incision to reset the injector, the IOL must be inserted into the injector, and the injector must be reloaded and replaced into the incision. This procedure is time-consuming, inefficient, and may introduce additional risk of surgical complications, specifically the stretching of the corneal incision, in a patient's eye.

The injector cartridge 4000 of FIG. 40 may be configured to insert both a prosthetic capsular device and an IOL into an eye without removal of the device from a corneal incision. In some embodiments, a single injector cartridge and push rod system is provided that allows both the prosthetic capsular device and the IOL to be implanted in one insertion. The left side chamber 4002 may contain the capsule, and the right-side chamber 4004 may contain the IOL. For example, as illustrated, the injector may comprise two or more loading chambers and/or channels, each of which funnels into a single distal injection chamber 4006. In some embodiments, the injector may comprise a "double-barrel" with two loading chambers, one for a prosthetic capsular device and one for an IOL, which will further simplify and expedite implantation. In some embodiments, one or more gates 4008 are provided, which prevent the prosthetic capsular device or IOL from being pressed backward into the opposing loading chamber. In some embodiments, push rods, such as screw push rods 4010, may be used to selectively load the prosthetic capsular device or IOL into the single distal injection chamber. In some embodiments, a foam-tip sponge 4012 trails the prosthetic capsular device and IOL within the injector to ensure that the prosthetic capsular device and IOL properly enter the eye.

In some embodiments, a surgical method is provided for implanting an ophthalmic prosthetic device and/or an IOL into an eye, the method comprising: inserting, using an injection system, the ophthalmic prosthetic device and IOL, through a corneal incision of an eye. In some embodiments, the method comprises using a single injector cartridge and push rod system that allows both the prosthetic capsular device and the IOL to be implanted in one insertion. In some embodiments, the method comprises using an injector, which comprises a "double-barrel" configuration with two loading chambers, one for a prosthetic capsular device and one for an IOL.

Figure 41:
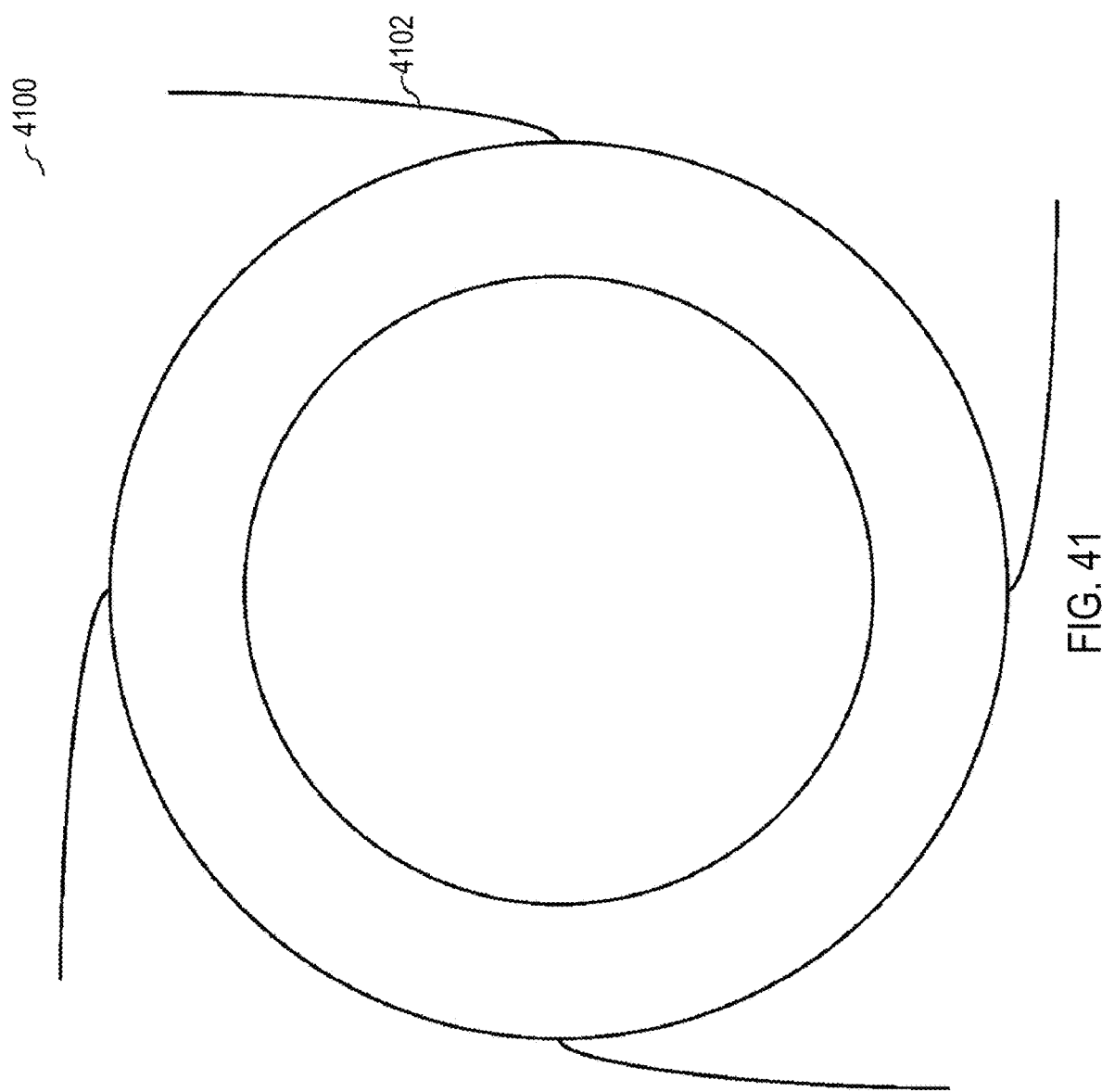
FIG. 41 illustrates another example prosthetic device according to some embodiments herein.

FIG. 41 illustrate another example prosthetic device according to some embodiments herein. In some embodiments, the prosthetic device 4100 may comprise one or more haptics 4102 extending from the exterior sidewall of the device 4100. In some embodiments, the one or more haptics 4102 facilitate fixation of the device on the sclera and can be implanted in a patient with trauma or surgical complications that caused loss of natural capsular support. In some embodiments, the haptics 4102 may prevent rotation of the prosthetic capsular device to ensure centration of the device within the capsular bag, especially for asymmetric natural capsular bags.

In some embodiments, the prosthetic devices described herein may support any IOLs known to those skilled in the art, wherein the IOL may be coupled or inserted into the device within the eye. Existing devices only allow specific compatible IOLs to be fixated to the sclera of the eye. However, using the prosthetic capsular device of FIG. 41, any IOL could be coupled or inserted into the device, which fixates to the sclera and serves as a platform for the IOL. In some embodiments, the haptics and the prosthetic capsular device may provide scleral fixation, creating an artificial replacement lens capsule, in which various IOLs may be coupled or inserted.

In addition, the prosthetic capsular devices described herein may be tinted to prevent positive dysphotopsias, as well as cover iris defects from trauma or laser peripheral iridotomies for angle closure glaucoma.

ADDITIONAL EMBODIMENTS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and sub-combinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein but are to be accorded the widest scope consistent with this disclosure, the principles and the novel features disclosed herein.

What is claimed is:

1. A prosthetic capsular device configured to be inserted in a natural capsular bag of an eye, the prosthetic capsular device comprising:
  a housing structure comprising:
    an anterior portion comprising:
      an anterior circular opening;
      an anterior rim surrounding the anterior circular opening and defining a perimeter of the anterior circular opening, the anterior rim comprising a first curved portion originating at the perimeter of the anterior circular opening and extending laterally outward and anteriorly from the perimeter of the anterior circular opening; and
      an anterior sidewall connected to the anterior rim and extending laterally outward and posteriorly from the anterior rim, the anterior sidewall comprising a first exterior curved surface and a first interior surface comprising a first straight portion and a second straight portion, wherein the first straight portion extends from the anterior rim to a first transition point of the first interior surface, and wherein the second straight portion extends from the first transition point of the first interior surface to a longitudinal center plane of the housing structure, and wherein the first straight portion is formed at an obtuse angle relative to the second straight portion;
    a posterior portion comprising:
      a posterior circular opening;
      a posterior rim surrounding the posterior circular opening and defining a perimeter of the posterior circular opening, the posterior rim comprising a second curved portion originating at the perimeter of the posterior opening and extending laterally outward and posteriorly from the perimeter of the posterior circular opening; and
      a posterior sidewall connected to the posterior rim and extending laterally outward and anteriorly from the posterior rim, the posterior sidewall comprising a second exterior curved surface and a second interior surface comprising a third straight portion and a fourth straight portion, wherein the third straight portion extends from the posterior rim to a first transition point of the second interior surface, and wherein the fourth straight portion extends from the first transition point of the second interior surface to the longitudinal center plane of the housing structure, and wherein the third straight portion is formed at an obtuse angle relative to the fourth straight portion;
    an interior cavity formed between the anterior circular opening and the posterior circular opening, the interior cavity configured to house an intraocular lens; and
    a groove formed by one or more ribs, the one or more ribs formed along an outermost circumference of the interior cavity at the longitudinal center plane of the housing structure, wherein each rib of the one or more ribs comprises a top surface formed at an obtuse angle relative to a bottom surface, and wherein the groove is configured to hold the intraocular lens in place within the interior cavity of the housing structure.

2. The prosthetic capsular device of claim 1, wherein the first exterior curved surface and the second exterior curved surface are continuous surfaces with substantially no openings.

3. The prosthetic capsular device of claim 1, wherein the first exterior curved surface and the second exterior curved surface connect at the longitudinal center plane of the housing structure.

4. The prosthetic capsular device of claim 1, wherein the housing structure is symmetrical, such that the anterior portion and the posterior portion are mirror images.

5. The prosthetic capsular device of claim 1, wherein the interior cavity is configured to house the intraocular lens of at least the following types: spherical, aspheric, wavefront, convex, concave, extended depth of focus, pinhole or small aperture, multifocal, toric, accommodative, ultraviolet (UV) filtering, diffractive chromatic aberration reducing, light adjustable, positive diopter, and negative diopter.

6. The prosthetic capsular device of claim 1, wherein the prosthetic capsular device is made of silicone or silicone polymer.

7. The prosthetic capsular device of claim 1, wherein the prosthetic capsular device is manufactured by compression molding, three-dimensional laser cutting, two photon lithography, additive manufacturing, or a combination of the above.

8. The prosthetic capsular device of claim 1, wherein the prosthetic capsular device comprises a flexible or elastic material, such that the prosthetic capsular device is foldable and self-expandable.

9. The prosthetic capsular device of claim 1, wherein a thickness of the anterior sidewall and the posterior sidewall is between about 0.1 mm and 1.0 mm.

10. The prosthetic capsular device of claim 1, wherein the rib angle is about 100°.

11. The prosthetic capsular device of claim 1, wherein the groove is formed by 12 ribs.

12. The prosthetic capsular device of claim 1, wherein the first straight portion and the third straight portion are formed at a sidewall angle.

13. The prosthetic capsular device of claim 12, wherein the sidewall angle is about 34° or about 57°.

14. The prosthetic capsular device of claim 1, wherein the interior cavity comprises a volume for maintaining the shape and size of the natural capsular bag.

15. The prosthetic capsular device of claim 1, further comprising one or more notches located on an exterior surface of the housing structure, protruding radially outward from the exterior surface.

16. The prosthetic capsular device of claim 15, wherein the one or more notches contact or engage a surface of the natural capsular bag.

17. The prosthetic capsular device of claim 15, wherein the one or more notches are located along the longitudinal center plane of the housing structure.

18. The prosthetic capsular device of claim 1, further comprising one or more ridges extending longitudinally from the anterior circular opening to the posterior circular opening.

19. The prosthetic capsular device of claim 18, wherein the one or more ridges are located intermittently around a circumference of the exterior of the device.

20. The prosthetic capsular device of claim 1, wherein an exterior surface of the housing comprises a textured surface, the textured surface comprising an adhesive, nanostructures, or micro-structures formed on the exterior surface.

* * * * *

UNITED STATES PATENT AND TRADEMARK OFFICE
CERTIFICATE OF CORRECTION

| | |
|---|---|
| PATENT NO. | : 11,364,107 B2 |
| APPLICATION NO. | : 17/499692 |
| DATED | : June 21, 2022 |
| INVENTOR(S) | : Wortz et al. |

It is certified that error appears in the above-identified patent and that said Letters Patent is hereby corrected as shown below:

On the Title Page

Column 2 (item (56) Other Publications), Line 1, delete ""Postive" and insert -- "Positive --.

Page 3, Column 1 (item (56) U.S. Patent Documents), Line 75, delete "2002/0128719" and insert -- 2002/0128710 --.

In the Drawings

Sheet 34 of 41 (FIG. 34), Line 2, delete "EQU" and insert -- EQUALLY --.

Sheet 39 of 41 (FIG. 39), Line 1, delete ".10" and insert -- Ø9.65±0.10 --.

Sheet 39 of 41 (FIG. 39), Line 2, delete "EQ" and insert -- EQUALLY --.

Sheet 39 of 41 (FIG. 39), Line 3, delete "10" and insert -- Ø6±0.10 --.

In the Specification

Column 11, Line 16, delete "ribs." and insert -- ribs, --.

Signed and Sealed this
Twenty-fifth Day of October, 2022

Katherine Kelly Vidal
*Director of the United States Patent and Trademark Office*